United States Patent [19]

Fenn

[11] Patent Number: 5,251,645
[45] Date of Patent: Oct. 12, 1993

[54] ADAPTIVE NULLING HYPERTHERMIA ARRAY

[75] Inventor: Alan J. Fenn, Wayland, Mass.

[73] Assignee: Massachusetts Institute of Technology, Cambridge, Mass.

[21] Appl. No.: 722,612

[22] Filed: Jun. 26, 1991

[51] Int. Cl.⁵ .............................................. A61N 5/00
[52] U.S. Cl. .................................. 607/154; 128/653.1
[58] Field of Search ...................... 128/804, 399, 653.1

[56] References Cited

U.S. PATENT DOCUMENTS

| | | | |
|---|---|---|---|
| 4,403,618 | 9/1983 | Turner et al. | 128/804 |
| 4,448,198 | 5/1984 | Turner | 128/422 |
| 4,462,412 | 7/1984 | Turner | 128/804 |
| 4,586,516 | 5/1986 | Turner | 128/804 |
| 4,589,423 | 5/1986 | Turner | 128/804 |
| 4,632,127 | 12/1986 | Sterzer | 128/804 |
| 4,638,813 | 1/1987 | Turner | 128/804 |
| 4,669,475 | 6/1987 | Turner | 128/399 |
| 4,672,980 | 6/1987 | Turner | 128/804 |
| 4,798,215 | 1/1989 | Turner | 128/804 |
| 4,860,752 | 8/1989 | Turner | 128/422 |
| 4,934,365 | 6/1990 | Morgenthaler | 128/399 |
| 4,951,688 | 8/1990 | Keren | 128/804 |
| 4,974,587 | 12/1990 | Turner et al. | 128/399 |
| 5,097,844 | 3/1992 | Turner | 128/804 |
| 5,101,836 | 4/1992 | Lee | 128/804 |

FOREIGN PATENT DOCUMENTS

| | | |
|---|---|---|
| 0167670A1 | 12/1984 | European Pat. Off. . |
| 0256524 | 8/1987 | European Pat. Off. . |
| WO80/01461 | 7/1980 | PCT Int'l Appl. . |
| 624409 | 9/1943 | United Kingdom . |
| 3831016A1 | 3/1990 | United Kingdom . |

OTHER PUBLICATIONS

Johnson et al. An Experimental Adaptive Nulling Receiver Utilizing the Sample Matrix Inversion Algorithm with Channel Equalization (1991) *IEEE*, vol. 39, No. 5, pp. 798-808.

Zhang, Y., et al., "Heating Patterns Generated by Phase Modulation of a Hexagonal Array of Interstitial Antennas", *IEEE Transactions on Biomedical Engineering*, 38(1): 92-97 (1991).

Boag, A., et al., "Optimal Excitation of Multiapplicator Systems for Deep Regional Hyperthermia", *IEEE Transactions on Biomedical Engineering*, 37(10): 987-995, (1990).

(List continued on next page.)

*Primary Examiner*—Lee S. Cohen
*Attorney, Agent, or Firm*—Testa, Hurwitz & Thibeault

[57] ABSTRACT

A hyperthermia array uses adaptive nulling with non-invasive auxiliary probes to reduce the electric field intensity at selected positions in the target body while maintaining a desired focus at a tumor thereby avoiding or reducing the occurrences of "hot spots" during ultrasonic or R.F. hyperthermia treatment. A hyperthermia applicator has an annular phased array of electric field radiators coupled to a source of electric radiation through a controllable transmit weighting network to control the phase and amplitude of the electric field radiation transmitted. The transmit weighting networks respond to feedback signals from a controller coupled to electric field probes which receive the electric field radiation from the radiators. The controller adjusts the feedback signals in response to the received electric field radiation so that the electric field radiation is minimized at the electric field probes. A secondary electric field probe is placed at the focus of the array and the controller adjusts the feedback signals to maximize the electric field radiation at the secondary probe. A matrix inversion algorithm or a gradient search algorithm is used to adjust the feedback signals controlling the transmit weighting networks in response to the electric field energy received by the electric field probes.

30 Claims, 37 Drawing Sheets

OTHER PUBLICATIONS

Sathiaseelan, V., "Potential for patient-specific optimization of deep heating patterns through manipulation of amplitude and phase", *Strahlenther Onkol*, 165(10): 743–745, (1989).

Loane, Joseph T. III, "Gain Optimization of a Near-Field Focusing Array for Hyperthermia Applications", *IEEE Transactions on Microwave Theory and Techniques*, 37(10): 1629–1635, (1989).

Roemer, R. B., et al., "Feedback Control and Optimization of Hyperthermia Heating Patterns: Present Status and Future Needs", *IEEE Eighth Annual Conference of the Engineering in Medicine and Biology Society*, 1496–1499, (1986).

Babbs, C. F., et al., "A Predictive-Adaptive, Multipoint Feedback Controller for Local Heat Therapy of Solid Tumors", *IEEE Transactions on Microwave Theory and Techniques*, MTT-34(5): 604–611, (1986).

Knudsen, Morten, et al., "Optimal Temperature Control with Phased Array Hyperthermia System", *IEEE Transactions on Microwave Theory and Techniques*, MTT-34(5): 597–603, (1986).

Morita, Nagayoshi, et al., "An Optimal Excitation Method in Multi-Applicator Systems for Forming a Hot Zone Inside the Human body", *IEEE Transactions on Microwave Theory and Techniques*, MTT-34(5): 532–538, (1986).

De Wagter, Carlos, "Optimization of Simulated Two-Dimensional Temperature Distributions Induced by Multiple Electromagnetic Applicators", *IEEE Transactions on Microwave Theory and Techniques*, MTT34(5): 589–596, (1986).

Sathiaseelan, V., et al., "Theoretical Analysis and Clinical Demonstration of the Effect of Power Pattern Control Using the Annular Phased-Array Hyperthermia System", *IEEE Transactions on Microwave Theory and Techniques*, MTT34(5): 514–519, (1986).

R = RESISTOR
C = CAPACITOR
P = POWER $R = \dfrac{1}{k\Delta\ell}$ [°C / W], k = THERMAL CONDUCTIVITY $C = \rho C_p (\Delta\ell)^3$ [J/°C], $\rho$ = DENSITY, $C_P$ = SPECIFIC HEAT $P = SAR\ \rho\ (\Delta\ell)^3$ [W], $SAR = \dfrac{\sigma}{2\rho}|E|^2$ (Specific Absorption Rate)

$\sigma$ = ELECTRICAL CONDUCTIVITY $|E|$ = MAGNITUDE OF ELECTRIC FIELD

| PARAMETER | PHANTOM MUSCLE TISSUE | DISTILLED WATER |
|---|---|---|
| DIELECTRIC CONSTANT @ 100 MHz | 73.5 | 80.0 |
| ELECTRICAL CONDUCTIVITY @ 100 MHz | 0.5 S/m | 0.0001 S/m |
| DENSITY | 970.0 kg/m$^3$ | 1000.0 kg/m$^3$ |
| SPECIFIC HEAT | 3516.0 J/kg °C | 4200.0 J/kg °C |
| THERMAL CONDUCTIVITY | 0.544 W/m °C | 0.6019 W/m °C |

Table 1

Fig. 16(b)

ADAPTIVE NULLING HYPERTHERMIA ARRAY

GOVERNMENT SUPPORT

The invention described herein was supported in whole or in part by Contract No. F19628-90-C-0002 from the United States Air Force.

BACKGROUND OF THE INVENTION

The successful treatment of deep-seated malignant tumors within a patient is often a difficult task. The objective of the treatment is to reduce in size or completely remove the tumor mass by one or more modalities available at the treatment facility. Common treatment modalities are surgery, chemotherapy, and x-ray therapy. One treatment modality used alone or in conjunction with one of the above modalities is "tissue heating", or hyperthermia. Hyperthermia can be considered as a form of high fever localized within the body. A controlled thermal dose distribution is required for hyperthermia to have a therapeutic value. Typical localized-hyperthermia temperatures required for therapeutic treatment of cancer are in the 43°–45° C. range. Normal tissue should be kept at temperatures below 43° C. during the treatment. Typically, hyperthermia is induced in the body by radio-frequency (RF) waves, acoustic (ultrasound) waves, or a combination of both. One of the most difficult aspects of implementing hyperthermia, with either RF or ultrasound waves, is producing sufficient heating at depth. Multiple-applicator RF hyperthermia arrays are commonly used to provide a focused near-field main beam at the tumor position. Ideally, a focal region should be concentrated at the tumor site with minimal energy delivered to surrounding normal tissue.

In RF hyperthermia systems, the hyperthermia antenna beamwidth is proportional to the RF wavelength in the body. A small focal region suggests that the RF wavelength be as small as possible. However, due to propagation losses in tissue, the RF depth of penetration decreases with increasing transmit frequency. One of the major side-effects in heating a deep-seated tumor with a hyperthermia antenna is the formation of undesired "hot spots" in surrounding tissue. This additional undesired heating often produces pain, burns, and blistering in the patient, which requires terminating the treatment immediately. The patient does not receive anesthetics during the hyperthermia treatment in order to provide direct verbal feedback of any pain. Thus, techniques for reducing hot spots while maximizing energy delivered to the tumor site are desired in hyperthermia treatment.

RF hyperthermia systems with electric field transmitting arrays, i.e., antenna arrays, in the frequency band of 60-2000 MHz have been used to localize heating of malignant tumors within a target body. Phase control alone of the transmitting antennas of such an array has been used to synthesize therapeutic RF radiation patterns within a target body. Theoretical studies of adaptive control of individual antenna phase and power (transmit weights) has been used to maximize the tumor temperature (or RF power delivered to the tumor) while minimizing the surrounding tissue temperature (or RF power delivered to the surrounding tissue). Invasive temperature measuring techniques have been used to optimize the radiation pattern within a target body.

One commercially available hyperthermia annular phased-array antenna system is the Model BSD-2000, SIGMA-60 applicator, available from BSD Medical Corporation, Salt Lake City, Utah. This phased-array system fully surrounds the patient, placing the patient at the center of an annular array of dipole transmit antennas. By fully surrounding the patient with an annular phased-array, it is possible to obtain constructive interference (or signal enhancement) deep within the target volume. This hyperthermia system uses a 60 cm array diameter with eight uniformly spaced dipole elements operating over the frequency band 60-120 MHz. The eight dipoles are fed as four active pairs of elements. There are four high-power amplifiers which drive the dipole pairs with up to 500 W average power per channel. Each of the four active channels has an electronically controlled variable-phase shifter for focusing the array. Temperature and electric-field probe sensors (both invasive and non-invasive) are used to monitor the treatment. A cool-water (5°-40° C.) bolus between the patient and the phased-array is used to prevent excess heating of the skin surface. The water bolus is filled with circulating distilled water, which has a very low propagation loss.

SUMMARY OF THE INVENTION

In accordance with the invention, adaptive nulling with non-invasive auxiliary probes is used to reduce the field intensity at selected positions in the target body while maintaining a desired focus at a tumor thereby avoiding or reducing the occurrences of "hot spots" during ultrasonic or R.F. hyperthermia treatment.

In general, in one aspect, the invention features a hyperthermia applicator having electric field radiators each coupled to a source of electric radiation through a controllable transmit weighting network to control the phase and amplitude of the electric field radiation transmitted by each radiator. The transmit weighting networks respond to feedback signals from a controller coupled to electric field probes which receive the electric field radiation from the radiators. The controller adjusts the feedback signals in response to the received electric field radiation so that the electric field radiation is minimized at the electric field probes.

Preferred embodiments include a phased-array of electric field radiators, and an annular array of electric field radiators for surrounding the target. The electric field probes include probes placed non-invasively around the perimeter of the target where the electric field energy is to be minimized. In one embodiment, the target is modeled as an ellipse and the electric field probes are placed at the front, back, and on both sides of the ellipse.

In another aspect, the invention also features a secondary electric field probe, and the controller adjusts the feedback signals in response to the electric field radiation received by the secondary electric field probe so that the electric field radiation is maximized at the secondary probe. Embodiments include placing the secondary probe at the desired focus of the electric field radiation.

In yet another aspect, the invention features the controller performing either a matrix inversion algorithm or a gradient search algorithm to adjust the feedback signals controlling the transmit weighting networks in response to the electric field energy received by the electric field probes.

Thus, the present invention offers the advantages of allowing effective hyperthermia treatment to be applied to deep seated tumors within the body while reducing or eliminating hot-spot formation on the surface of the body which interferes with the treatment. Another advantage is that hot spots are eliminated quickly by sensing and adjusting the E-field radiation in the vicinity of the expected hot spot rather than by measuring the temperature rise of the of after heating has already occurred. Still another advantage is that the E-field sensing probes may be located on the surface of the target rather than having to be invasively placed within the target body.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout different views. The drawings are not necessarily to scale, emphasis instead being placed upon illustrating the principles of the invention.

FIG. 16(b) is a table of values used in the simulation model of FIG. 16(a).

DETAILED DESCRIPTION OF THE PREFERRED EMBODIMENT

Apparatus

Figure 1:
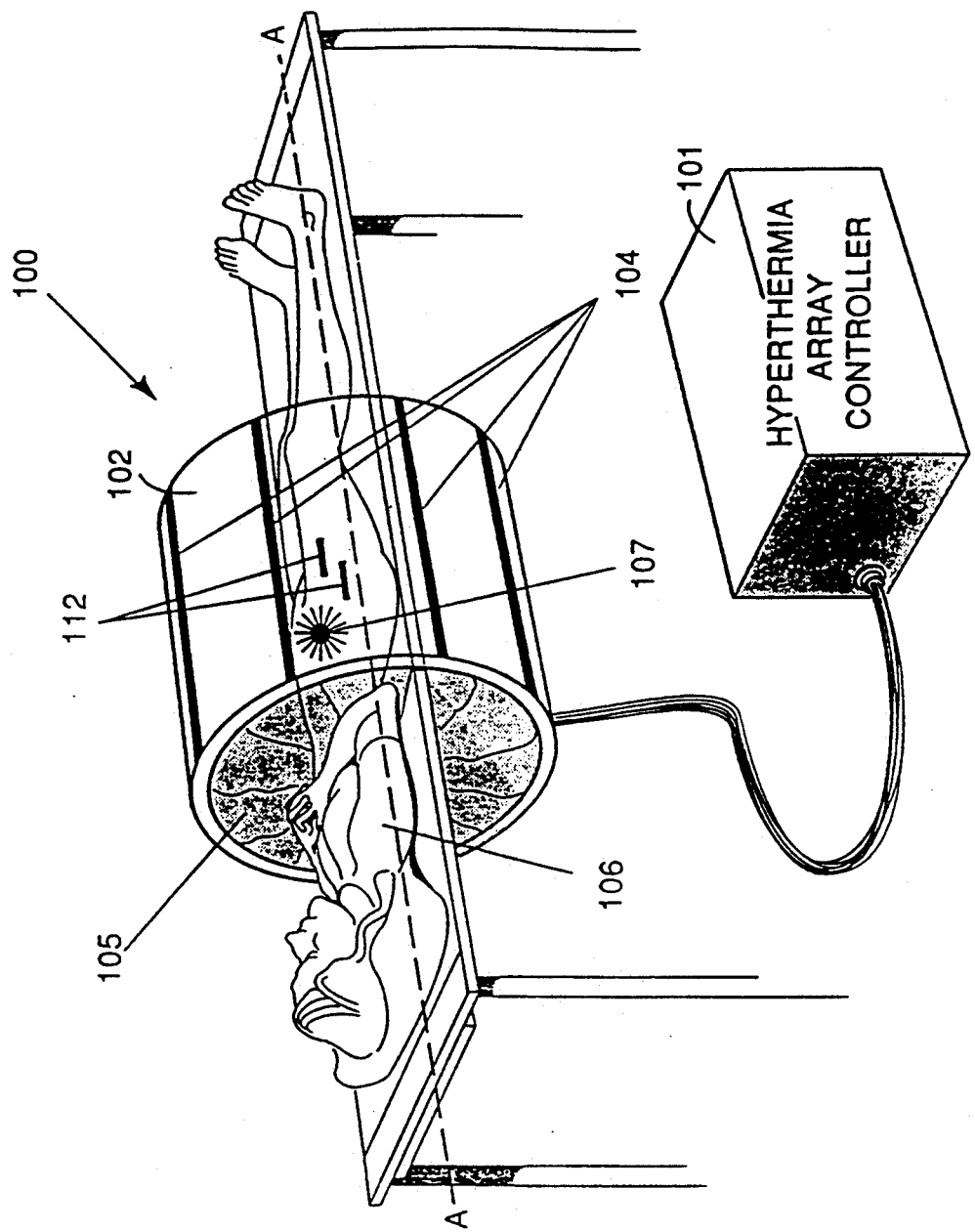
FIG. 1 is a perspective view of an RF annular array hyperthermia system featuring the adaptive nulling of this invention.

Referring to FIG. 1, there is shown a hyperthermia annular phased-array system 100 having improved "hot spot" characteristics through utilizing the focused near-field adaptive nulling apparatus of this invention. An annular hyperthermia phased-array transmit antenna 102, energized by a hyperthermia array controller 101, has a plurality of dipole transmit antenna elements 104 is placed around a patient to be treated, or target body 106, so that the dipole antenna elements are uniformly disposed around the patient. Each dipole antenna element is oriented parallel to the other dipole antennas and parallel to a longitudinal axis A passing through the center of the cylinder. The patient is positioned within the hyperthermia phased-array such that the deep-seated tumor to be treated 107 is at the approximate center, or focus, of the array. A water-bolus 105 is maintained between the patient and the array to control the temperature of the patient's skin.

Phased-array 102 therapeutically illuminates the target body 106 by focusing electric field energy radiated by dipole antenna elements 104 on tumor 107 deep within the body. An example of a deep-seated tumor is cancer of the prostate. The tumor volume often has a decreased blood flow which aids in heating the tumor, compared to normal tissue for which heat is carried away by normal blood flow. In practice, undesired high-temperature regions away from the focus can also occur on the skin and inside the volume of the target body. For example, scar tissue, which has a decreased blood flow rate, will tend to heat up more rapidly than normal tissue having normal blood flow. In the adaptive hyperthermia array of this invention, electric-field nulls are used to reduce the power delivered to potential hot spots. Computer simulations, presented herein, show that non-invasive field probes, or sensors, 112 placed on the surface of the target can be used to eliminate hot spots interior to the target tissue. With the adaptive hyperthermia phased-array described herein, RF energy nulls are adaptively formed to reduce the electric field energy delivered to these potential hot spots. As shown, the energy nulls achieved by the adaptive nulling apparatus of this invention are both invasive to the target, i.e., extend into the target body, and non-invasive to the target, i.e., on the surface of the target.

Figure 2:
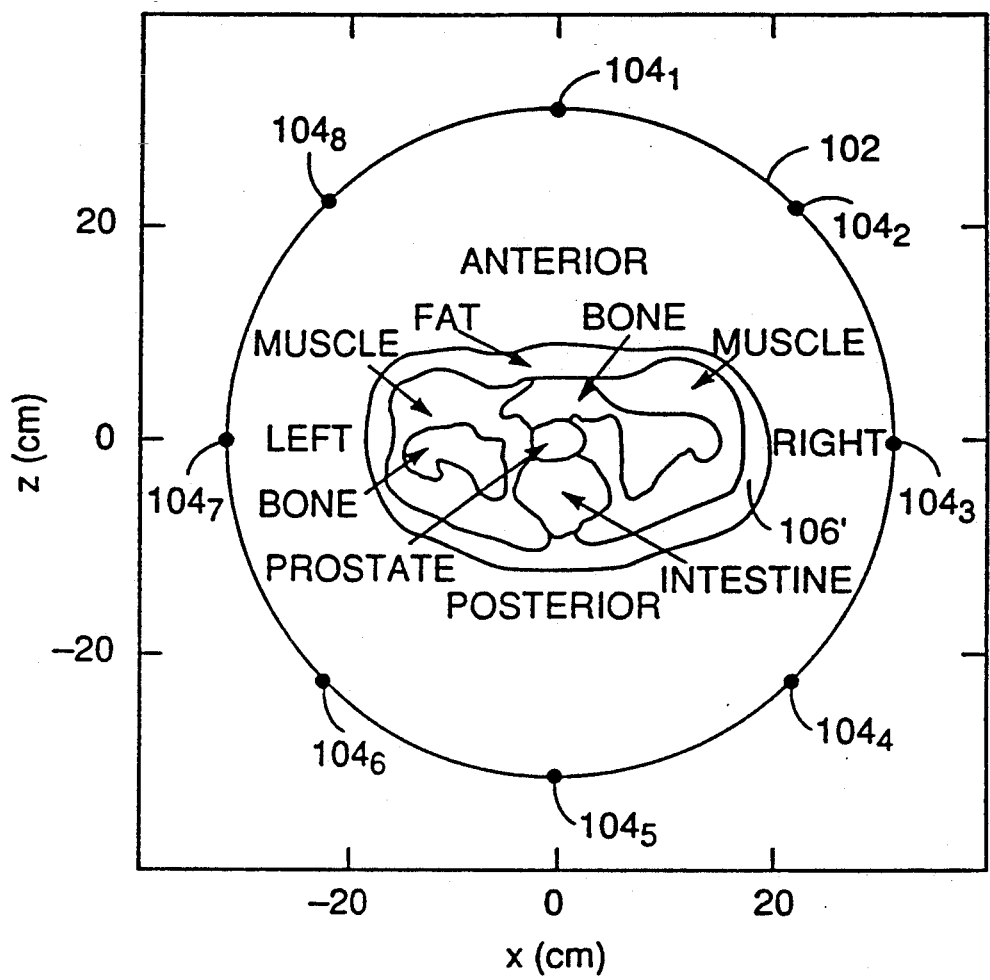
FIG. 2 is a cross-sectional representation of the annular array of FIG. 1.

Referring to FIG. 2, there is shown a schematic cross-sectional representation of an embodiment of an eight-element hyperthermia phased-array 102 of FIG. 1. Phased-array 102 has transmit antennas 104; through 104$_8$, arranged symmetrically surrounding a human body target 106' at the prostate level.

Figure 3:
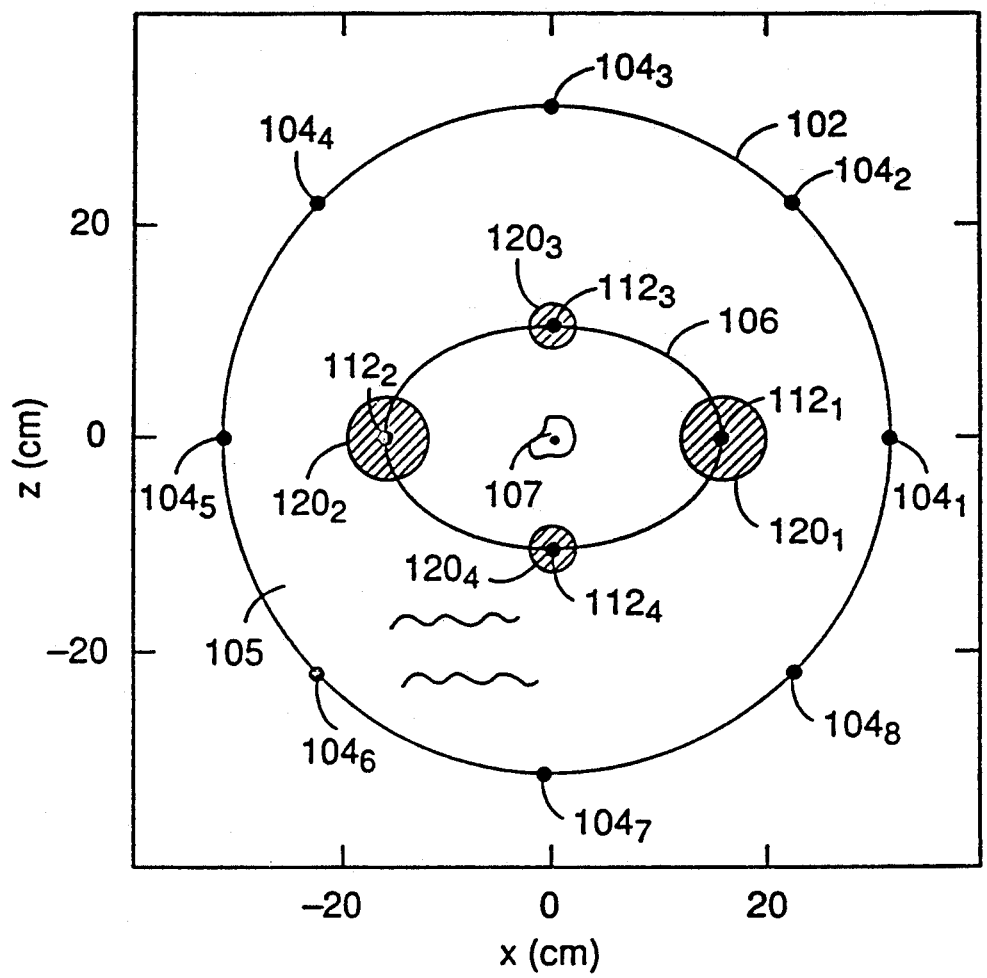
FIG. 3 is an analytical model of the cross-sectional representation of FIG. 2.

An analytical model of the embodiment of FIG. 2 is shown in FIG. 3. Here, an elliptical phantom target 106 is used to model the prostate-level cross section of the human body 106'. The center 107 of the elliptical phantom models the location of the prostate tumor to receive hyperthermia treatment, i.e., the focus of RF energy for the phased array 102. Water bolus 105 is assumed to surround the target body 106, and is treated as a homogeneous medium for analysis purposes.

Four auxiliary RF E-field probes, or sensors, $112_1$ through $112_4$, i.e., receiving antennas, are placed around the perimeter of the target to model non-invasive probes placed on the skin of the human body target. Each auxiliary probe $112_1$ through $112_4$ has a corresponding null zone $120_1$ through $120_4$, respectively, centered at each auxiliary probe and extending into the elliptical target region 106. Each null zone indicates an area in which undesired "hot spots" are reduced or eliminated. The width of each null zone is directly related to the depth of each null. The depth of each null (sometimes referred to as the amount of cancellation) is directly related to the signal-to-noise ratio at the probe position ($SNR_P$). A low $SNR_P$ indicates a large amount of nulling (strong null), and a high $SNR_P$ indicates a small amount of nulling (weak null). The resolution, or minimum spacing, between the focus 107 and any null position is normally equal to the half-power beamwidth of the transmit antenna. Resolution may be enhanced somewhat by using weak nulls whenever the separation between the null and focus is closer than the half-power beamwidth.

Figure 4:
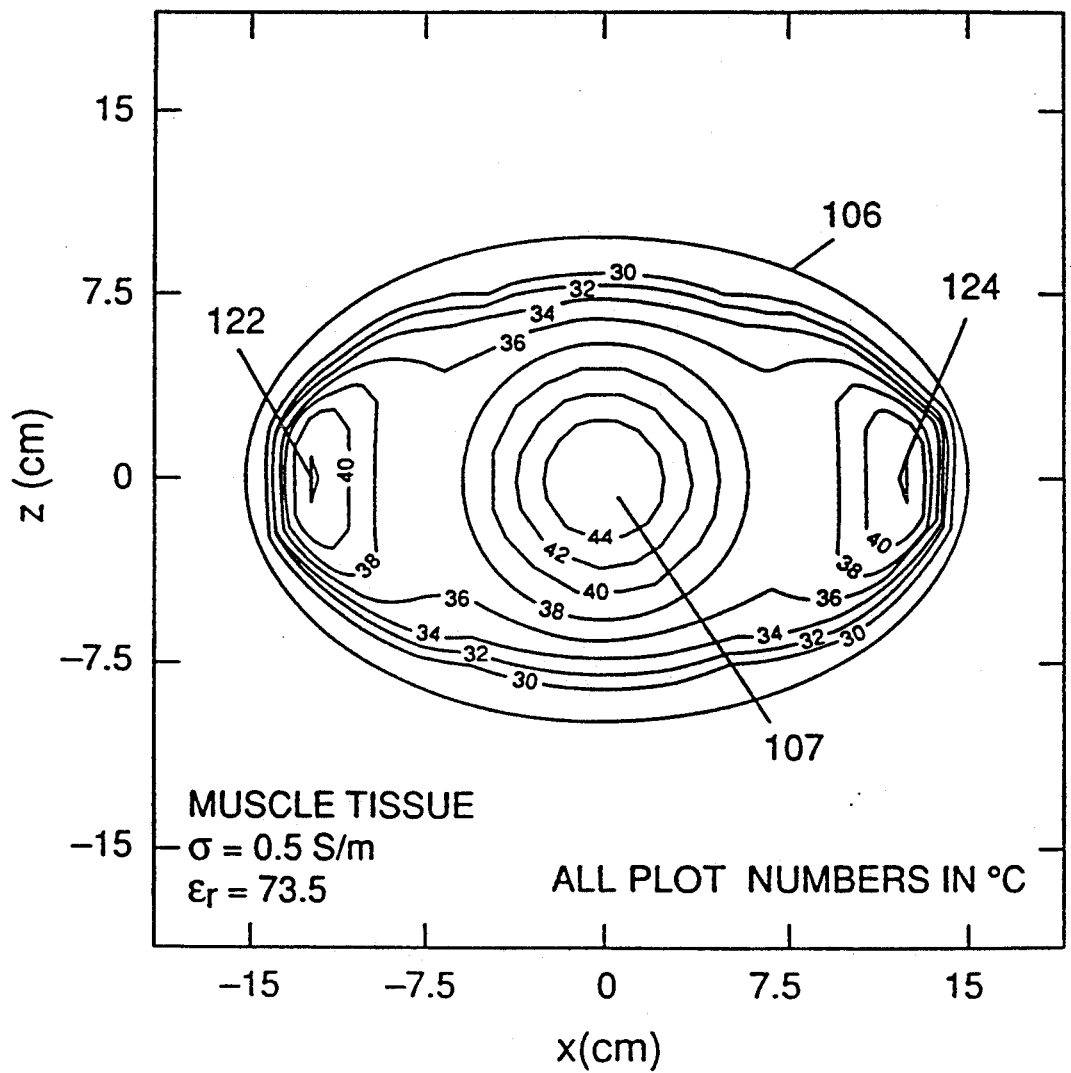
FIG. 4 is a simulated thermal profile of the analytical model of FIG. 3 without the adaptive nulling of this invention.

Referring to FIG. 4, there is shown the results of a simulation of the thermal distribution inside the target body 106 for the hyperthermia ring array 102 of the analytical model of FIG. 3, without adaptive nulling, transmitting into the target body. For simulation purposes, target body 106 is assumed to be a homogeneous elliptical region, and the RF energy from the array is focused at the center of the ellipse 107, simulating the tumor site. No adaptive nulling is used. The contour lines of the thermal distribution represent isotherms having the indicated temperature in degrees Celcius (°C.), and are spaced at 2° C. intervals. The simulation shows that the focus is expected to have a temperature of approximately 46° C., while two undesired "hot spots" 122 and 124 to the left and right of the focus, respectively, are expected to have temperatures of approximately 42° C.

Figure 5:
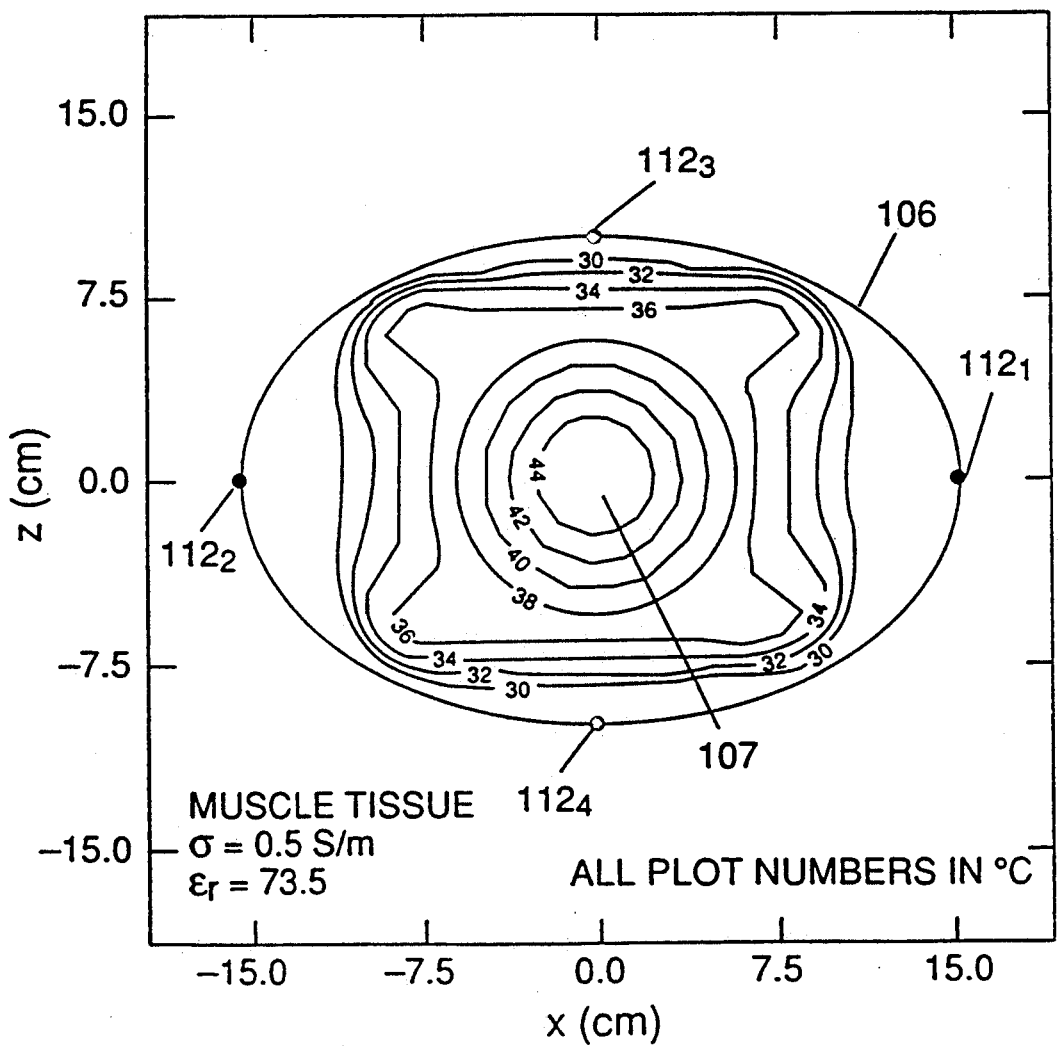
FIG. 5 is a simulated thermal profile of the analytical model of FIG. 3 with the adaptive nulling of this invention.

FIG. 5 shows a simulated thermal distribution for the model of FIG. 3 where the adaptive nulling methods of this invention is applied. Comparison of FIG. 5 with FIG. 4 show that the "hot spots" 122 and 124 are essentially eliminated, no new "hot spots" have been produced Within the target body, and the peak temperature induced at the focus is still approximately 46° C.

Figure 6:
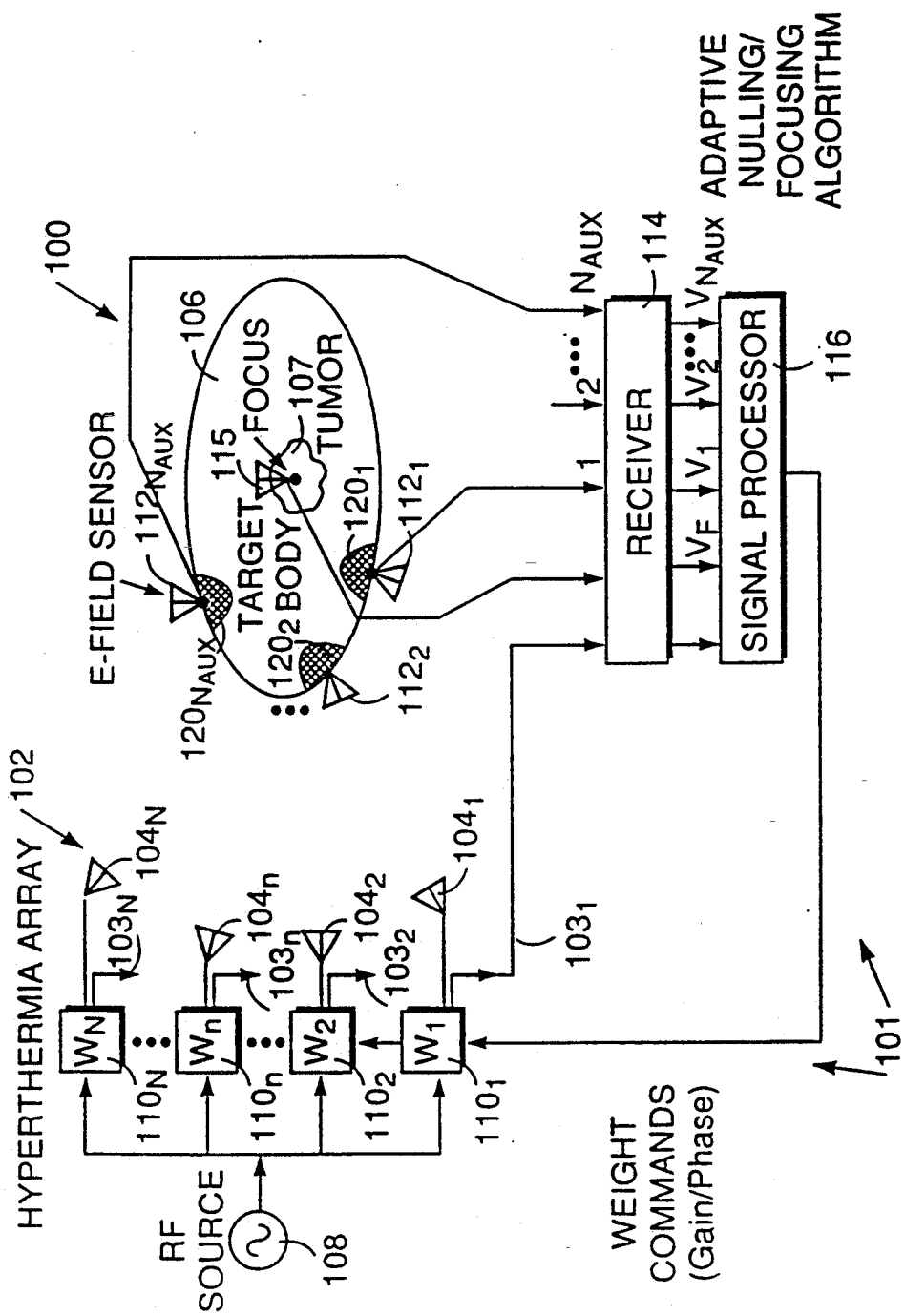
FIG. 6 is a schematic diagram of the adaptive hyperthermia array and array controller of FIG. 1.

Referring to FIG. 6, a generalized schematic of the non-invasive adaptive-nulling hyperthermia system of FIG. 3 includes hyperthermia transmitting antenna array 102 having a plurality of transmitting antenna elements $104_n$, where n=1, ..., N, surrounding target body 106 for focusing RF energy at focus 107 within the target body. Antenna array 102 is energized by an RF energy source 108 which is distributed to and drives each transmit antenna element $104_n$ through a corresponding transmit antenna weighting function $110_n$, each having a corresponding weight $w_n$. Each weighting function $w_n$ may affect the gain and phase of the RF energy fed to its corresponding antenna $104_n$ in the array, i.e., $w_n$ represents a complex weighting function. Each weighting function $110_n$ may be implemented by a voltage controlled RF amplifier and a voltage controlled RF phase shifter. An amplitude control voltage representing the amplitude component of transmit weight $w_n$ is fed to the voltage controlled amplifier, and a phase control voltage representing the phase of transmit weight $w_n$ is fed to the voltage controlled phase shifter.

Target body 106 has a plurality of E-field auxiliary probes $112_m$, where m=1, ..., $N_{aux}$, i.e., receiving antennas, positioned at various locations on the surface of the body for sampling the E-field at each particular location. Another receiving probe 115 may be placed at the desired focus 107 of the array.

Receiving probes $112_m$ and 115 each drive an input to an RF receiver 114. The transmit amplitude and phase weights of each weighting function $w_n$ are fed to the receiver 114 through lines $103_n$ and are used to find the transmit level of each transmit element $104n$. The outputs of receiver 114 represent the auxiliary probe-received complex voltages $v_1, v_2, ..., v_{Naux}$, the focus probe-received complex voltage $v_f$, and the transmit level of the phased array. The receiver outputs drive the inputs of a signal processor 116, which applies a nulling algorithm to adjust the weighting functions $w_n$ and thereby null, or minimize, the RF signal received by each receiving probe $112_m$, i.e., minimize the $SNR_P$ at each probe.

To generate the desired field distribution in a clinical adaptive hyperthermia system, the receiving probes are positioned as close as possible to the focus (tumor site) and to where high temperatures are to be avoided (such as near the spinal cord and scar tissue). For an annular array configuration the receiving probes can be located non-invasively on the surface (skin) of the target. Initially, the hyperthermia array is focused to produce the required field intensity at the tumor. An invasive probe may be used to achieve the optimum focus at depth. To avoid undesired hot spots, it is necessary to minimize the power received at the desired null positions and to constrain the array transmit weights $w_n$ to deliver a required amount of transmitted or focal region power.

Signal processor 116 performs either a sample matrix inversion (SMI) algorithm or a gradient search algorithm on the signals output from receiver 114 and updates the adaptive array weights $w_n$ (with gain g and phase $\phi$) to rapidly (within seconds) form the nulls at the auxiliary probes before a significant amount of target heating takes place. With this adaptive system, it is possible to avoid unintentional hot spots in the proximity of the auxiliary probes and maintain a therapeutic thermal dose distribution at the focus (tumor).

Signal processor 116 may also perform a maximizing algorithm to maximize energy at the focus 107. The focus probe 115 is invasively placed at the desired focus 107, and used to generate a maximum signal, or signal-to-noise ratio ($SNR_F$), at the tumor site. RF receiver 114 makes an amplitude and phase measurement on the output signal from invasive probe 115 for each transmit antenna element $104_n$ radiating one at a time. Signal processor 116 processes these measurements and feeds back weight command signals to the transmit weighting functions $110_n$ to calibrate or phase align the transmit channels to thereby maximize the $SNR_F$, or RF power, at the invasive focal point probe. If receiver 114 makes amplitude-only measurements from invasive focus probe 115, then a gradient search technique may be applied by the signal processor with all elements transmitting simultaneously to maximize the $SNR_F$ at the invasive focal point probe.

Theoretical Formulation of Nulling Algorithms

Figure 7:
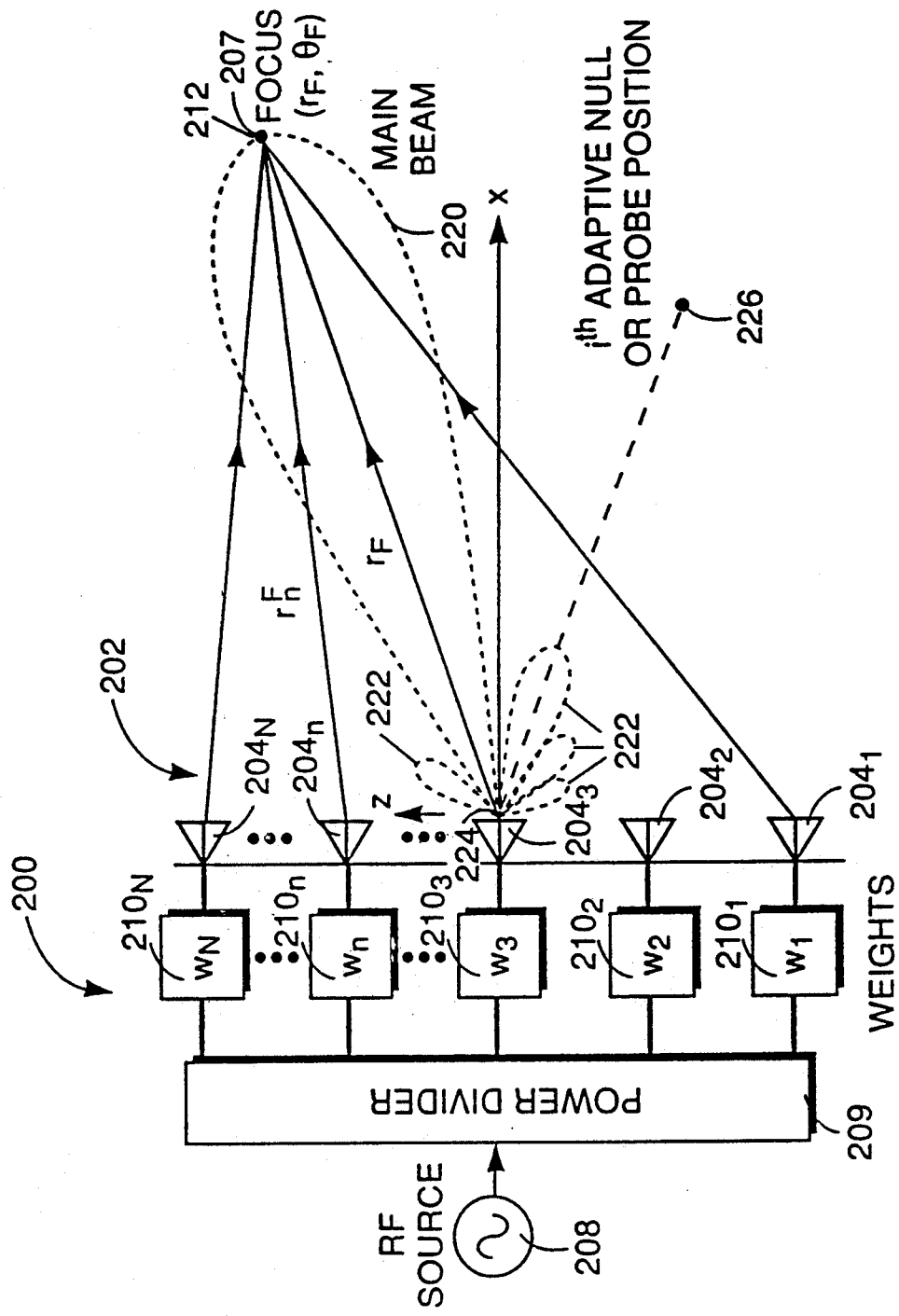
FIG. 7 is a schematic diagram of an analytical model of an adaptive array for simulating the hyperthermia array of FIG. 1.

FIG. 7 shows an analytical model of a hyperthermia phased-array antenna system 200, paralleling the generalized hyperthermia phased-array antenna system 100 of FIG. 6, illustrating the principles of the near-field adaptive nulling technique of this invention. The phased-array antenna system 200 includes a hyperthermia transmitting antenna array 202 having a plurality of transmitting antennas $204_n$, where n=1, . . . ,N for focusing RF energy at a desired focus 207 in the near field of the antenna. Antenna array 202 is energized by an RF energy source 208 which drives a power divider 209. Power divider 209 has one output for driving each antenna $204_n$ a corresponding transmit weighting function $210_n$, each having a corresponding transmit weight $w_n$. It is assumed here that each weighting function $w_n$ may affect the phase of the RF energy fed to its corresponding antenna $204_n$ in the array. A calibration E-field probe 212, or focus probe antenna, is positioned at focus 207 for sampling the E-field at that location.

It is assumed that the hyperthermia phased-array antenna 200 is focused (as it normally is) in the near field and that a main beam 220 and possibly sidelobes 222 are formed in the target. In general, phase and amplitude focusing is possible. It is assumed that phase focusing alone is used to produce the desired quiescent main beam, i.e., weighting functions $w_n$ affects only the phase of the RF signal driving each antenna. The signal received by the calibration probe can be maximized by adjusting the phase weighting functions $w_n$ so that the observed transmit antenna element-to-element phase variation is removed, i.e., all transmit antennas appear to be in-phase when observed from the focus.

One way to achieve phase coherence at the focus in a numerical simulation is to choose a reference path length as the distance from the focus to the phase center 224 of the array. This distance is denoted $r_F$ and the distance from the focus to the nth array transmit antenna element is denoted $r_n^F$. The voltage received at the calibration probe 212 (located at focus 207) due to the nth array element may be computed using the "method of moments", as described below. To maximize the received voltage at the calibration probe output, it is necessary to apply the phase conjugate of the signal observed at the calibration probe, due to each array transmit antenna element, to the corresponding element at the transmit array. The resulting near-field radiation pattern will have a main beam and sidelobes. The main beam will be pointed at the array focal point, and sidelobes will exist at angles away from the main beam. Auxiliary probes can then be placed at the desired null positions in the quiescent sidelobe region. These sidelobes occur where tissue hot spots are likely to occur, and they are nulled by one of the adaptive nulling algorithms described below.

Adaptive Transmit Array Formulation

Considering again the hyperthermia array and probe geometry shown in FIG. 7, the hyperthermia transmit antenna array 202 typically contains N identical transmit antenna elements 204. The number of adaptive channels is denoted M, and for a fully adaptive array M=N. The ideal transmit weights $w_n$ (a complex voltage gain vector) are assumed in the computer simulation, with $w=(w_1,w_2, \ldots ,w_N)^T$ denoting the adaptive channel weight vector as shown in FIG. 6. (Superscript T means transpose). To generate adaptive nulls, the transmit weights (phase and gain) are controlled by either the Sample Matrix Inversion (SMI) algorithm or a gradient search algorithm. The SMI algorithm has the flexibility to operate in either open- or closed-loop feedback modes; the gradient search algorithm operate only in a feedback mode.

Sample Matrix Inversion (SMI) Algorithm

For the SMI algorithm, the fundamental quantities required to fully characterize the incident field for adaptive nulling purposes are the adaptive channel cross correlations. To implement this algorithm it is necessary to know the complex received voltage at each of the auxiliary probes. For example, the moment-method formulation (described below) allows computation of complex-received voltage at each of the auxiliary probes.

Figure 8:
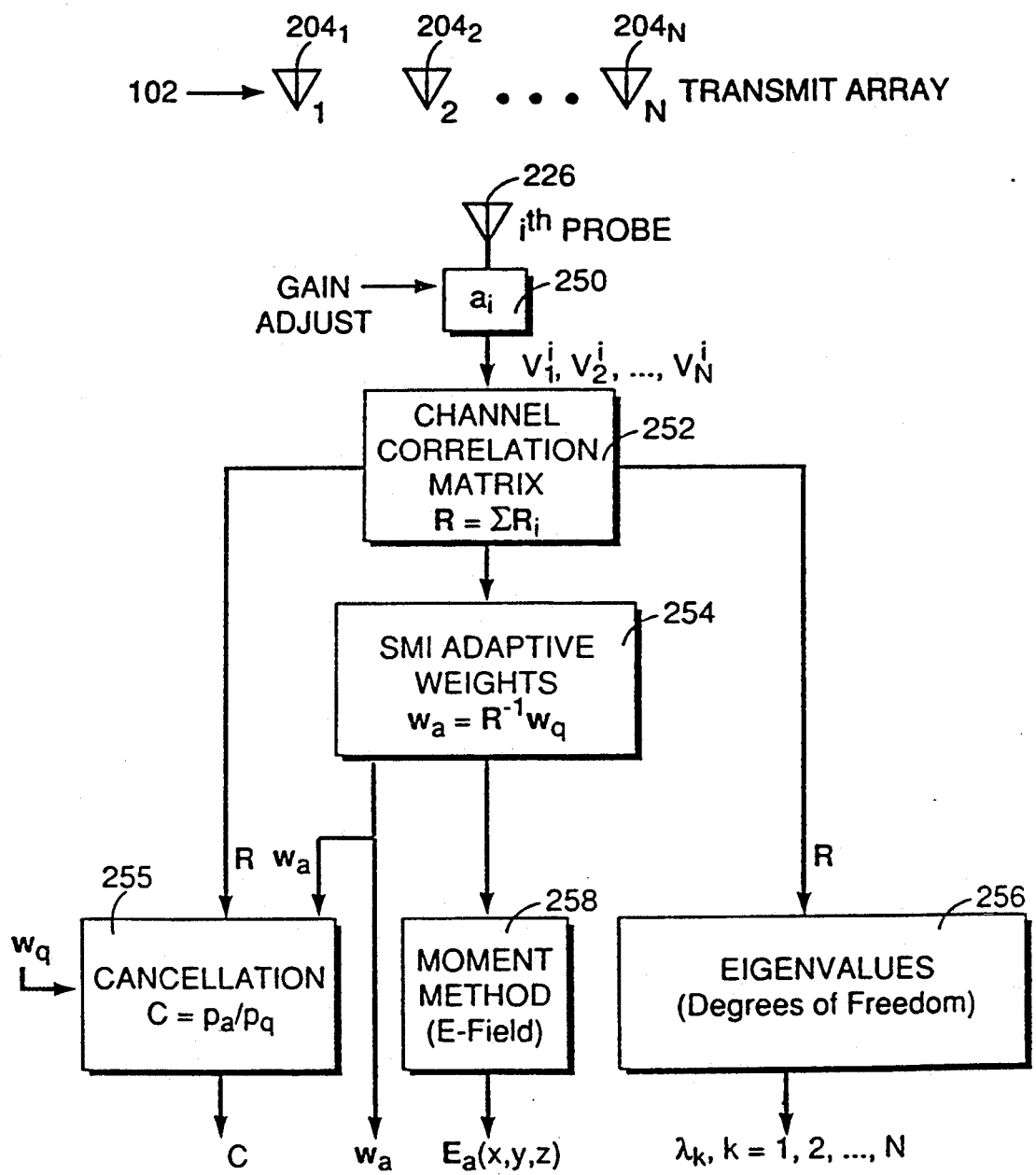
FIG. 8 is a block diagram detailing the sample matrix inversion algorithm derived from the adaptive hyperthermia array model of FIG. 7.

FIG. 8 is a block diagram showing the SMI algorithm applied to the adaptive hyperthermia phased-array of FIG. 7, and the derivation of performance measures to quantify computer simulation results. Four performance measures are used to quantify the computer simulations: electric-field distribution E(x,y,z), channel correlation matrix eigenvalues $\lambda_k$, k=1, . . . ,N, adaptive transmit weights $w_a$, and interference cancellation C. The calculation of these performance measures is described in detail below.

Assuming a spherical wavefront is incident at an ith probe antenna 226 due to each of the N array transmit antenna elements $204_n$ (radiating one at a time with a unity-amplitude reference signal), the result is a set of probe-received complex voltages denoted $v_1^i, v_2^i, \ldots ,v_N^i$ after a gain adjustment 250. The cross correlation $R_{mn}^i$ of the received voltages due to the mth and nth transmit antenna (adaptive transmit channel) at the ith probe is given by $$R_{mn}^i = E(v_m v_n^*), \qquad (1)$$

where * means complex conjugate and E(*) means mathematical expectation. (Note: for convenience, in Equation (1) the superscript i in $v_m$ and in $v_n$ has been omitted.) Because $v_m$ and $v_n$ represent voltages of the same waveform but at different times, $R_{mn}^i$ is also referred to as an autocorrelation function.

In the frequency domain, assuming the transmit waveform has a band-limited white noise power spectral density (as commonly assumed in radar system analysis), Equation (1) can be expressed as the frequency average $$R_{mn}^i = \frac{1}{B} \int_{f_1}^{f_2} v_m(f) v_n^*(f) df, \tag{2}$$

where $B = f_2 - f_1$ is the nulling bandwidth, or bandwidth of frequencies applied by the hyperthermia treatment, and f is the transmit frequency of the hyperthermia array. It should be noted that $v_m(f)$ takes into account the transmit wavefront shape, which is spherical for the hyperthermia application. For the special case of a continuous wave (CW) transmit waveform, as normally used in hyperthermia, the cross correlation reduces to $$R_{mn}^i = v_m(f_o) v_n^*(f_o) \tag{3}$$

where $f_o$ is the transmit frequency of the hyperthermia array.

Next, the channel correlation matrix, or interference covariance matrix, denoted R is determined 252. (Note: in hyperthermia, interference is used to refer to the signals received at the auxiliary probes. The undesired "hot spots" can be thought of as interfering with the therapy.) If there are $N_{aux}$ independent desired null positions or auxiliary probes, the $N_{aux}$-probe channel correlation matrix is the sum of the channel correlation matrices observed at the individual probes. That is, $$R = \sum_{i=1}^{N_{aux}} R_i + I, \tag{4}$$

where $R_i$ is the sample channel correlation matrix observed at the ith probe and I is the identity matrix used to represent the thermal noise level of the receiver for simulation purposes.

Prior to generating an adaptive null, the adaptive channel weight vector, w, is chosen to synthesize a desired quiescent radiation pattern. When nulling is desired, the optimum set of transmit weights to form an adaptive null (or nulls), denoted $w_a$, is computed 254 by $$w_a = R^{-1} w_q, \tag{5}$$

where $^{-1}$ means inverse and $w_q$ is the quiescent weight vector. During array calibration, the normalized quiescent transmit weight vector, with transmit element $204_1$ radiating, is chosen to be $w_q = (1,0,0, \ldots ,0)^T$, i.e., the transmit channel weight of element $204_1$ is unity and the remaining transmit channel weights are zero. Similar weight settings are used to calibrate the remaining transmit elements. For a fully adaptive annular array focused at the origin in homogeneous tissue, the normalized quiescent weight vector is simply $w_4 = (1,1,1, \ldots ,1)^T$. Commonly, the weight vector is constrained to deliver a required amount of power to the hyperthermia array or to the tumor. For simplicity in the computer simulation used to analyze the hyperthermia array, the weights are constrained such that $$\sum_{n=1}^{N} |w_n|^2 = 1, \tag{6}$$

where $w_n$ is the transmit weight for the nth element. It should be noted that in the computer simulations, the electric field due to the normalized weight vector is scaled appropriately to deliver the required amount of power to the tissue so that a desired focal-region temperature level is achieved after t minutes. The summation of power received at the probes is given by $$p = w^+ R w, \tag{7}$$

where + means complex conjugate transpose. The signal-plus-noise-to-noise ratio for the auxiliary probe array, denoted $SNR_P$, is computed as the ratio of the auxiliary probe array output power (defined in Equation (7)) with the transmit signal present, to the probe array output power with only receiver noise present, that is, $$INR = \frac{w^+ R w}{w^+ w}. \tag{8}$$

Next, the adaptive array cancellation ratio, denoted C, is determined 255. C is defined here as the ratio of the summation of probe-received power after adaptation to the summation of probe-received power before adaptation (quiescent); that is, $$C = \frac{p_a}{p_q}. \tag{9}$$

Substituting Equation (7) into Equation (9) yields $$C = \frac{w_a^+ R w_a}{w_q^+ R w_q}. \tag{10}$$

Next, the channel correlation matrix defined by the elements in Equations (2) or (3) is Hermitian (that is, $R = R$ ), which, by the spectral theorem, can be decomposed 256 in eigenspace as $$R = \sum_{k=1}^{M} \lambda_k e_k e_k^+. \tag{11}$$

where $\lambda_k$, $k = 1, 2, \ldots M$ are the eigenvalues of R, and $e_k$, $k = 1, 2, \ldots, M$ are the associated eigenvectors of R. The channel correlation matrix eigenvalues $(\lambda_1, \lambda_2, \ldots ,\lambda_M)$ are a convenient quantitative measure of the use of the adaptive array degrees of freedom. The amplitude spread between the largest and smallest eigenvalues is a quantitative measure of the dynamic range of the interference (hot spot) signals.

Figure 9:
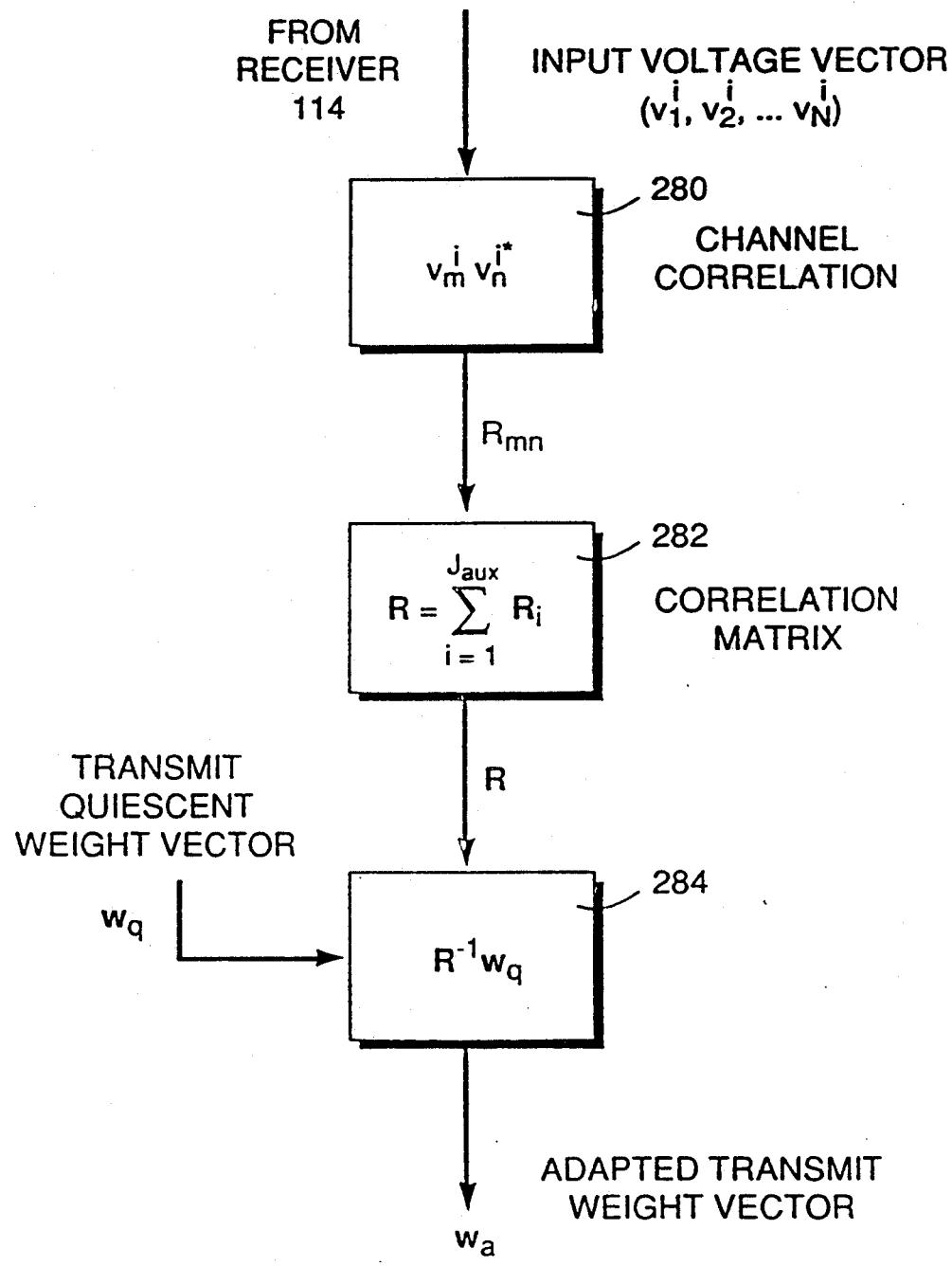
FIG. 9 is a block diagram of the sample matrix inversion algorithm performed by the hyperthermia array controller of FIG. 6.

FIG. 9 is a block diagram of the sample matrix inversion algorithm implemented by the signal processor 116 of FIG. 6. Receiver 114 generates probe-received complex voltage vector $v_1^i, v_2^i, \ldots , v_N^i$ for the ith auxiliary probe. The signal processor generates 280 the transmit channel correlations $R_{mn}^i$ defined by equation (3), and sums 282 them to form the channel correlation matrix R defined by equation (4). Next, the signal processor multiplies 284 the inverse of the channel correlation matrix $R^{-1}$ by the quiescent transmit weight vector $w_q$ to form the new adapted transmit weight vector $w_a$ containing the adapted transmit weights fed back to the transmit weight networks $110_n$ of FIG. 6.

Gradient Search Algorithm

Under conditions where only the probe received voltage amplitude is measured, it is appropriate to consider a gradient search algorithm to minimize the interference power at selected positions. The gradient search is used to control the transmit weights $w_n$ iteratively such that the RF signal received by the probe array is minimized. The transmit array weights (gain and phase) are adaptively changed in small increments and the probe array output power is monitored to determine weight settings that reduce the output power most rapidly to a null.

Consider J sets of N transmit weights that are applied to adaptive hyperthermia phased array antenna 102 of FIG. 6. In terms of adaptive nulling, the optimum transmit weight settings (from the collection of J sets of N transmit weights) occur when the $SNR_P$ is minimized. Equivalently, the total interference power received by the auxiliary probe array, denoted $P^{rec}$, is to be minimized. For notational L convenience let a figure of merit F denote either the $SNR_p$ or $P^{rec}$ and employ a gradient search to find the optimum transmit weights to minimize F, that is, $$F_{opt} = min(F_j) j = 1, 2 \ldots, J. \quad (12)$$

The transmit weight settings for which $F_{opt}$ occurs yields the closest approximation to the optimal transmit weights determined by using the sample matrix inverse approach described above.

Figure 10:
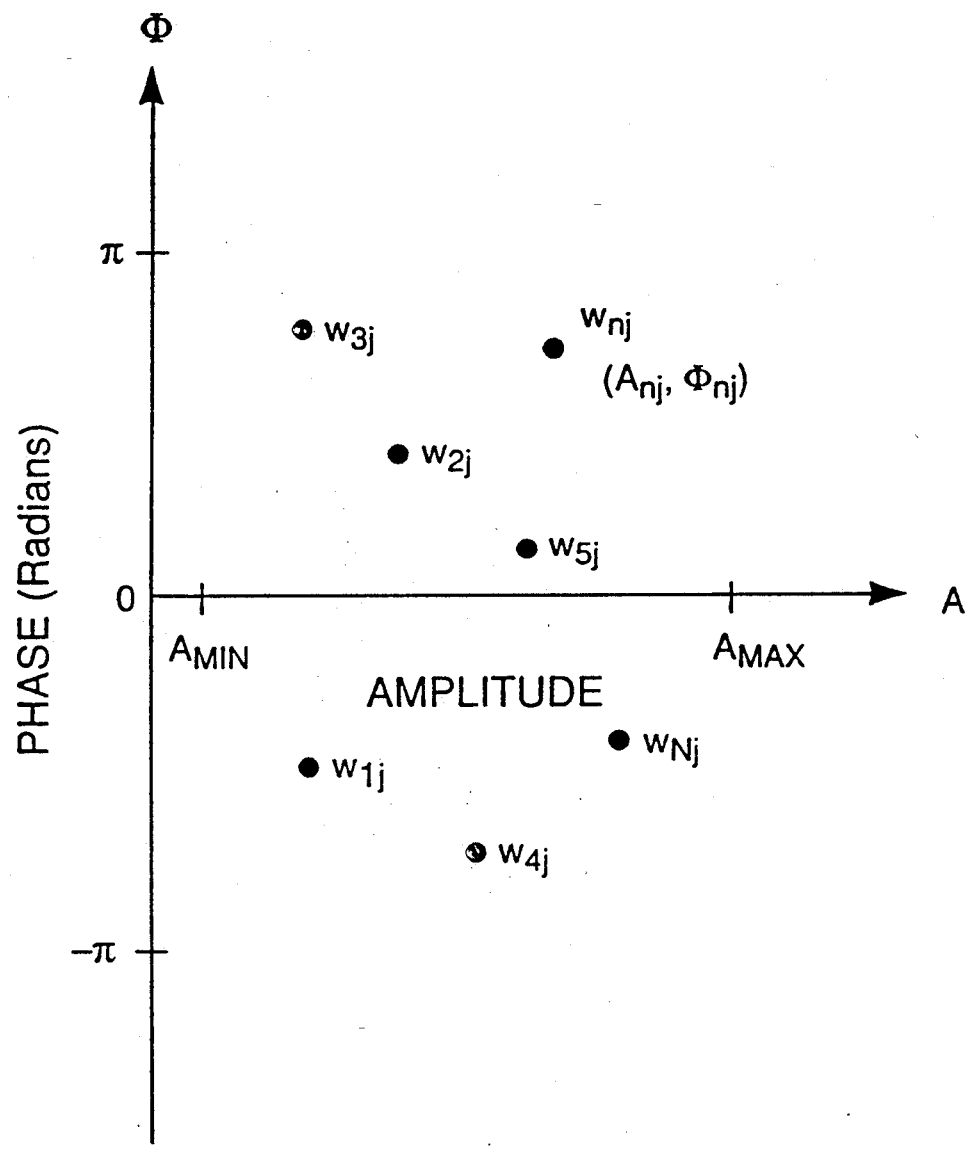
FIG. 10 is a scatter diagram of transmit weights used in deriving the gradient search adaptive hyperthermia algorithm.

FIG. 10 shows an amplitude and phase scatter diagram for the N complex transmit weights $w_n$ at the jth configuration, i.e., the jth set of weights tried. The nth transmit weight in the jth configuration of transmit weights is denoted $$w_{nj} = A_{nj} e^{j\Phi_{nj}}, \quad (13)$$

where $A_{nj}$ is the transmit weight amplitude distributed over the range $A_{min}$ to $A_{max}$ and $\Phi_{nj}$ is the transmit weight phase distributed over the range $-\pi$ to $\pi$ radians.

Figure 11:
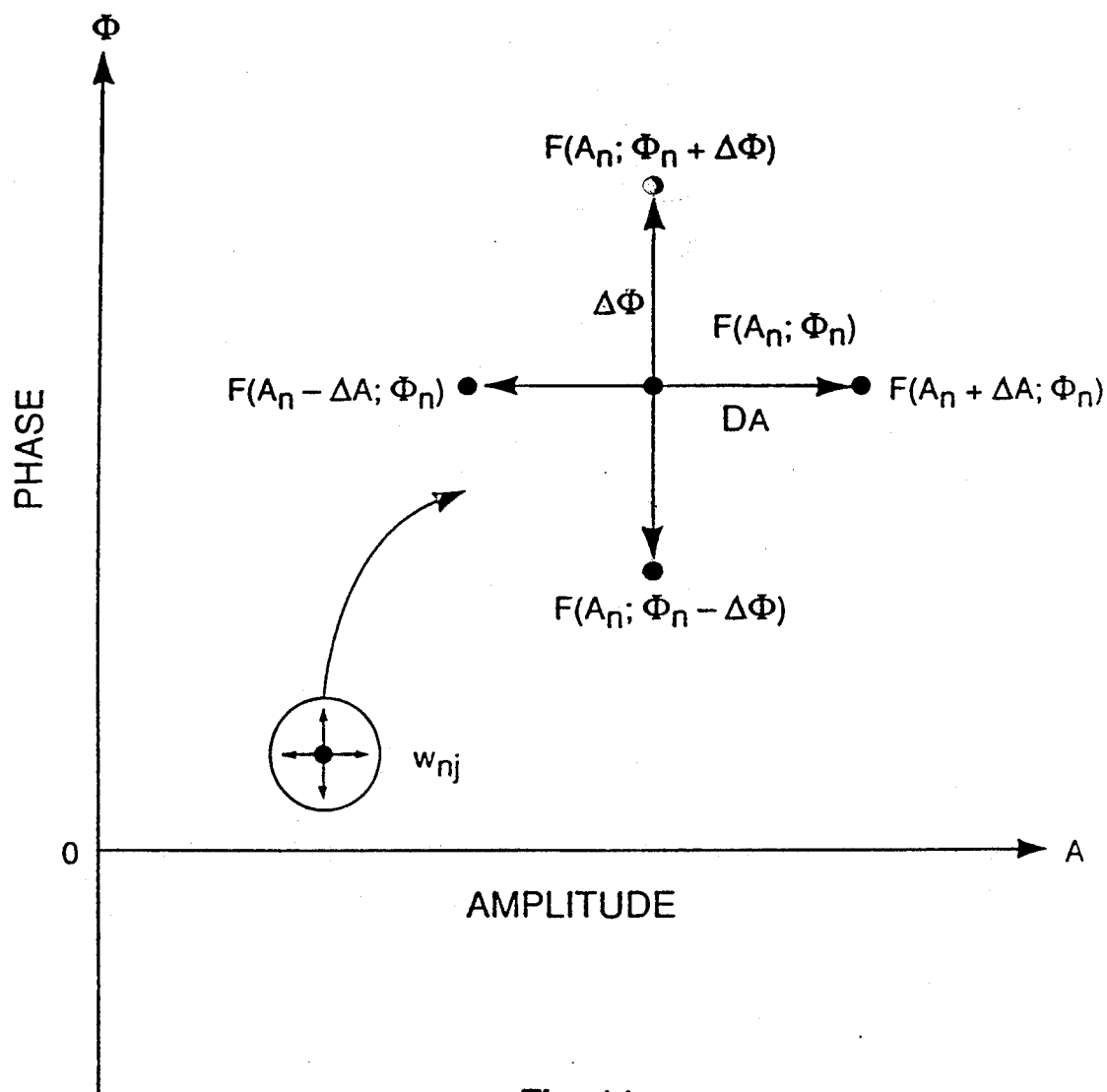
FIG. 11 is a diagram showing the derivation of the gradient search directions.

Referring also to FIG. 11, it is desired to find the values of amplitude and phase for each of the N transmit weights such that the figure of merit F ($SNR_p$ or $p^{rec}$) is minimized. When the figure of merit is minimized, adaptive radiation pattern nulls will be formed at the auxiliary probe positions.

Assuming an initial setting of the N transmit weights such as those selected to focus the radiation pattern on a tumor, the weights are adjusted by dithering them until the optimum figure of merit is achieved. It is desired to find the collective search directions for the N transmit weights such that F decreases most rapidly. That is, weights are selected so that the directional derivative is minimized at $(A_j, \Phi_j)$, where $A_j$ and $\Phi_j$ are vectors representing the transmit amplitude weights and transmit phase weights, respectively, for the jth configuration.

The directional derivative of $F_j$ is expressed in terms of the amplitude and phase changes of the transmit weights as $$D(F_j) = \sum_{n=1}^{N} \left( \frac{\partial F_j}{\partial A_{nj}} r_{Anj} + \frac{\partial F_j}{\partial \Phi_{nj}} r_{\Phi nj} \right) \quad (14)$$

where $\partial$ means partial derivative, and $r_{Anj}$, $r_{\Phi nj}$ are the $(A, \Phi)$ directions for which $F_j$ is decreasing most rapidly. The directions $r_{Anj}$, $r_{101\,nj}$ are constrained by $$\sum_{i=1}^{N} (r_{Anj}^2 + r_{\Phi nj}^2) = 1. \quad (15)$$

It is desired to minimize $D(F_j)$ subject to the above constraint equation.

Using Lagrange multipliers it is possible to construct the Lagrangian function $$L_j = \sum_{n=1}^{N} \left( \frac{\partial F_j}{\partial A_{nj}} r_{Anj} + \frac{\partial F_j}{\partial \Phi_{nj}} r_{\Phi nj} \right) + G \left[ 1 - \sum_{n=1}^{N} (r_{Anj}^2 + r_{\Phi nj}^2) \right] \quad (16)$$

where G is a constant to be determined. The requirement that $L_j$ be an extremum implies $$\frac{\partial L_j}{\partial r_{Anj}} = \frac{\partial F_j}{\partial A_{nj}} - 2G r_{Anj} = 0, \; n = 1, 2, \ldots, N \quad (17)$$

and $$\frac{\partial L_j}{\partial r_{\Phi nj}} = \frac{\partial F_j}{\partial \Phi_{nj}} - 2G r_{\Phi nj} = 0, \; n = 1, 2, \ldots, N \quad (18)$$

or that $$r_{Anj} = \frac{1}{2G} \frac{\partial F_j}{\partial A_{nj}} \quad (19)$$

and $$r_{\Phi nj} = \frac{1}{2G} \frac{\partial F_j}{\partial \Phi_{nj}}. \quad (20)$$

Squaring equations (19) and (20) and invoking equation (15)

$$\sum_{i=1}^{N} (r_{Anj}^2 + r_{\Phi nj}^2) = 1 = \frac{1}{4G^2} \sum_{n=1}^{N} \left[ \left( \frac{\partial F_j}{\partial A_{nj}} \right)^2 + \left( \frac{\partial F_j}{\partial \Phi_{nj}} \right)^2 \right] \quad (21)$$

thus, $$G = \pm \frac{1}{2} \sqrt{ \sum_{n=1}^{N} \left[ \left( \frac{\partial F_j}{\partial A_{nj}} \right)^2 + \left( \frac{\partial F_j}{\partial \Phi_{nj}} \right)^2 \right] }. \quad (22)$$

Substituting the expression for G in equations (19) and (20) gives $$r_{Anj} = - \frac{\frac{\partial F_j}{\partial A_{nj}}}{\sqrt{ \sum_{n=1}^{N} \left[ \left( \frac{\partial F_j}{\partial A_{nj}} \right)^2 + \left( \frac{\partial F_j}{\partial \Phi_{nj}} \right)^2 \right] }} \quad (23)$$

and

-continued $$r_{\Phi nj} = - \frac{\frac{\partial F_j}{\partial \Phi_{nj}}}{\sqrt{\sum_{n=1}^{N}\left[\left(\frac{\partial F_j}{\partial A_{nj}}\right)^2 + \left(\frac{\partial F_j}{\partial \Phi_{nj}}\right)^2\right]}}. \quad (24)$$

The minus sign was chosen corresponding to the direction of maximum function decrease. This choice of minus sign in equation (22) enforces nulls in the hyperthermia array radiation pattern. Alternatively, if the positive sign in equation (22) is selected, then the gradient directions can be used to maximize the figure of merit for the purposes of focusing at an invasive probe at the tumor site, i.e., maximize the $SNR_F$. This may be used, for example, to determine the quiescent transmit weight vector $w_q$. Thus, two gradient searches may be performed to optimize the radiation pattern of the hyperthermia array. The first to produce a peak or focused radiation pattern at the tumor, and the second to form the desired nulls at the auxiliary probes. Furthermore, these two gradient searches may be implemented as a single, combined gradient search constrained to maximize the radiation pattern at the focus and minimize the radiation pattern at the desired nulls. The combined gradient search is implemented by minimizing the figure of merit defined as the ratio of the power received at the auxiliary probes to the power received by the probe at the focus.

The partial derivatives $$\frac{\partial F_j}{\partial A_{nj}}, \frac{\partial F_j}{\partial \Phi_{nj}}; n = 1, 2, \ldots, N \quad (25)$$

represent the gradient directions for maximum function decrease. Since the figure of merit F cannot be expressed here in analytical form, the partial derivatives are numerically evaluated by using finite differences. Thus, we write $$\frac{\partial F_j}{\partial A_{nj}} = \frac{\Delta F_{Anj}}{2\Delta A_{nj}} \quad (26)$$

and $$\frac{\partial F_j}{\partial \Phi_{nj}} = \frac{\Delta F_{\Phi nj}}{2\Delta \Phi_{nj}} \quad (27)$$

where as shown in FIG. 2 the figure of merit differences are $$\Delta F_{Anj} = F_j(A_{nj} + \Delta A_{nj}, \Phi_{nj}) - F_j(A_{nj} - \Delta A_{nj}, \Phi_{nj}) \quad (28)$$

and $$\Delta F_{\Phi nj} = F_j(A_{nj}, \Phi_{nj} + \Delta \Phi_{nj}) - F_j(A_{nj}, \Phi_{nj} - \Delta \Phi_{nj}) \quad (29)$$

and $\Delta A_{nj}$ and $\Delta \Phi_{nj}$ are assumed to be small increments. We will assume that the increments $\Delta A_{nj}$ and $\Delta \Phi_{nj}$ are independent of the configuration number and element number, that is, $$\Delta A_{nj} = \Delta A \quad (30)$$

and $$\Delta \Phi_{nj} = \Delta \Phi \quad (31)$$

Substituting equations (26), (27), (30) and (31) in equations (23) and (24) gives the desired result for the search directions $$r_{Anj} = - \frac{\frac{\Delta F_{Anj}}{\Delta A}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}} \quad (32)$$

and $$r_{\Phi nj} = - \frac{\frac{\Delta F_{\Phi nj}}{\Delta \Phi}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}. \quad (33)$$

Equations (32) and (33) are used to compute the new amplitude and phase settings of the (j+1)th transmit weight configuration according to $$A_{n,j+1} = A_{nj} + \Delta A r_{Anj} \quad (34)$$

and $$\Phi_{n,j+1} = \Phi_{nj} + \Delta \Phi r_{\Phi nj}. \quad (35)$$

In practice, it may be necessary to keep one of the transmit weights fixed (in amplitude and in phase) during the gradient search to guarantee convergence.

Figure 12:
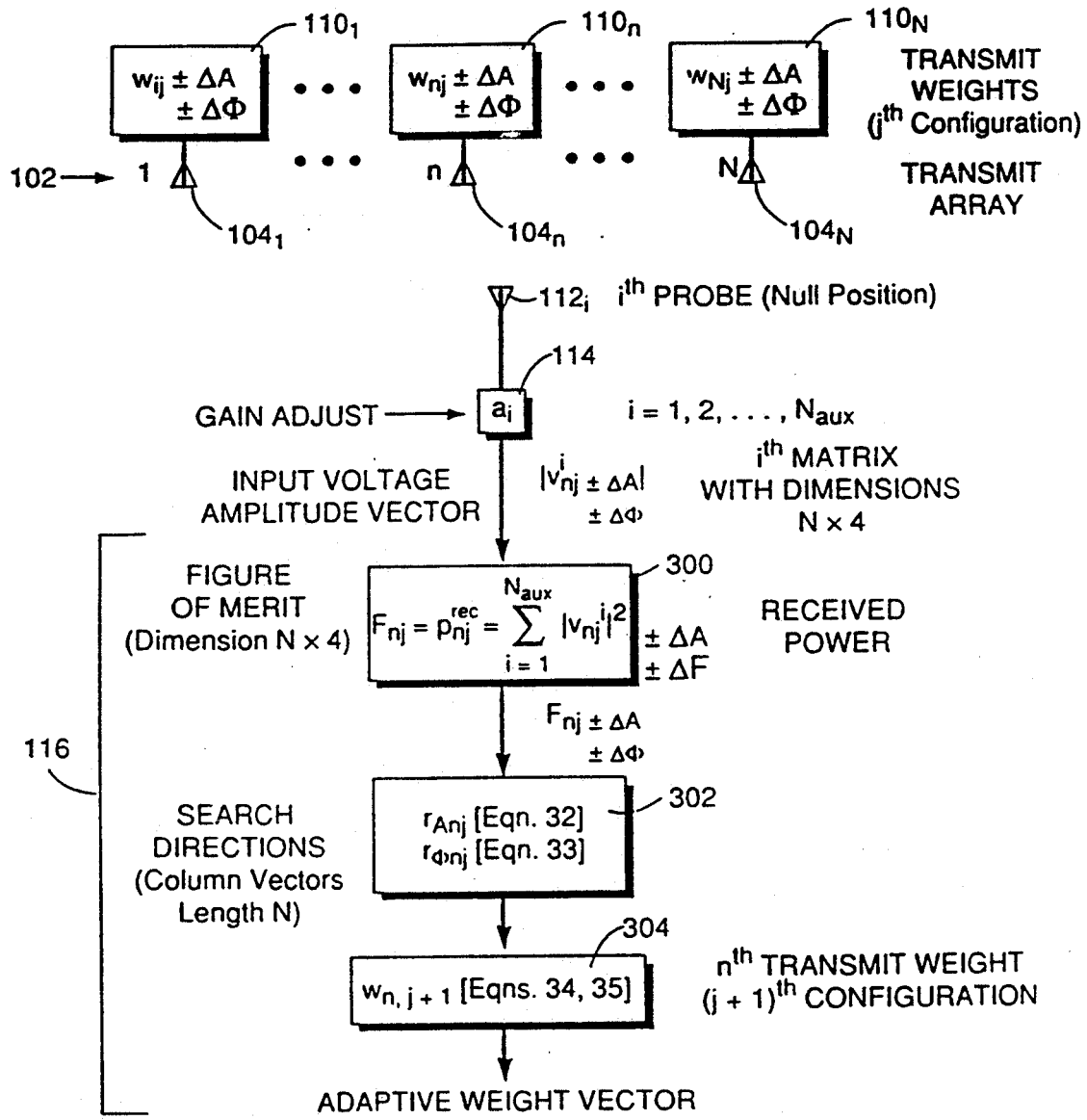
FIG. 12 is a block diagram of the gradient search performed by the hyperthermia array controller of FIG. 6.

FIG. 12 is a block diagram of the gradient search algorithm implemented by the signal processor 116 of FIG. 6. Each of the N transmit antennas $104_n$ of array 102 (FIG. 6) is driven through its corresponding weighting network $110_n$ which applies complex transmit weights $w_{nj}$ at the jth configuration of the weights. The transmit antennas induce a voltage across the ith probe antenna $112_i$ at the corresponding input to receiver 114 (FIG. 6). Receiver 114 amplifies the signal received from the ith probe by gain $a_i$ to produce voltage amplitude vector $|v_1{}^j|, |v_2{}^j|, \ldots, |v_N{}^j|$ at the receiver output.

The voltage amplitude vector is input to signal processor 116 which performs the gradient search. For any initial configuration (j=1) of the transmit weights $w_{nj}$, the signal processor causes each weight to be dithered by a small amount in amplitude, $\Delta A_{nj}$, and phase, $\Delta \Phi_{nj}$. Each transmit weight is dithered independent of the other transmit weights, which remain in their jth configuration state. Received voltage vectors $|v_1{}^j|, |v_2{}^j|, \ldots, |v_N{}^j|$, i.e., are stored and used to calculate the resulting figure of merit $F_{nj}$ 300 for each dithered condition, the figure of merit being the power received by the auxiliary prove array. The figure of merit is a rectangular matrix of dimension N×4, where the dimensionality of four is due to the plus and minus dithering of both of the amplitude and phase. The figure of merit differences $\Delta F_{Anj}$ and $\Delta F_{\Phi nj}$ caused by dithering the amplitude and phase, respectively, are calculated according to equations (28) and (29). The gradient search directions $r_{Anj}$ and $r_{\Phi nj}$, based upon minimizing the auxiliary probe array received power, are then determined 302 from the figure of merit differences according to equations (32) and (33), respectively. The resulting search directions are used to update 304 transmit weights $w_{nj}$ to the (j+1)th configuration transmit weights $w_{n,(j+1)}$ according to equations (34) and (35). The transmit weights $w_{n,(j+1)}$ are sent to update the transmit weighting networks $110_n$, and the process is repeated. The final adaptive weight vector $w_a$ is achieved when the (j+1)th transmit weight configuration has converged. Convergence is expected to occur within several hundred iterations depending on the dither step size $\Delta A$ and $\Delta \Phi$.

COMPUTER SIMULATION OF ADAPTIVE NULLING HYPERTHERMIA

Moment-Method Formulation

Referring again to FIG. 8, a method of moments formulation 258 is used to compute the probe-received voltages in Equation (2) due to the transmitting hyperthermia phased-array antenna in an infinite homogeneous conducting medium. The medium is described by the three parameters $\mu$, $\epsilon$, and $\sigma$, which are discussed below. The formulation given here is analogous to that developed under array-receiving conditions for an adaptive radar. The software used to analyze a hyperthermia array is based on the receive-array analogy but the theory presented below is given in the context of a transmit array.

An antenna analysis code (WIRES) originally developed by J. H. Richmond is capable of analyzing antenna or radar cross section problems. See, J. H. Richmond, "Computer program for thin-wire structures in a homogeneous conducting medium", Ohio State University, ElectroScience Laboratory, Technical Report 2902-12, August 1973; and, J. H. Richmond, "Radiation and scattering by thin-wire structures in a homogeneous conducting medium (computer program description)", IEEE Trans. Antennas Propagation, Vol. AP-22, no. 2, p. 365, March 1974. WIRES was modified to analyzing the near-field and far-field adaptive nulling performance of thin-wire phased arrays in free space. A new version of the thin-wire code that can analyze adaptive hyperthermia arrays in an infinite homogeneous conducting medium was written to conduct the adaptive hyperthermia simulation discussed below. The new version of the thin-wire code is attached as Appendix A.

WIRES is a moment-method diode that uses the electric field integral equation (EFIE) to enforce the boundary condition of the tangential field being zero at the surface of the antenna of interest. The moment-method basis and testing functions used in this code are piecewise sinusoidal.

Appendix B lists sample input and output files for the adaptive hyperthermia simulation. The first data file was used to generate the E-field results for a four auxiliary probe system, and the second data file was used to generate the E-field results for a two auxiliary probe system. The corresponding output files give the values for the array mutual coupling, quiescent and adaptive transmit weights, channel correlation matrix, eigenvalues, and cancellation.

Figure 13:
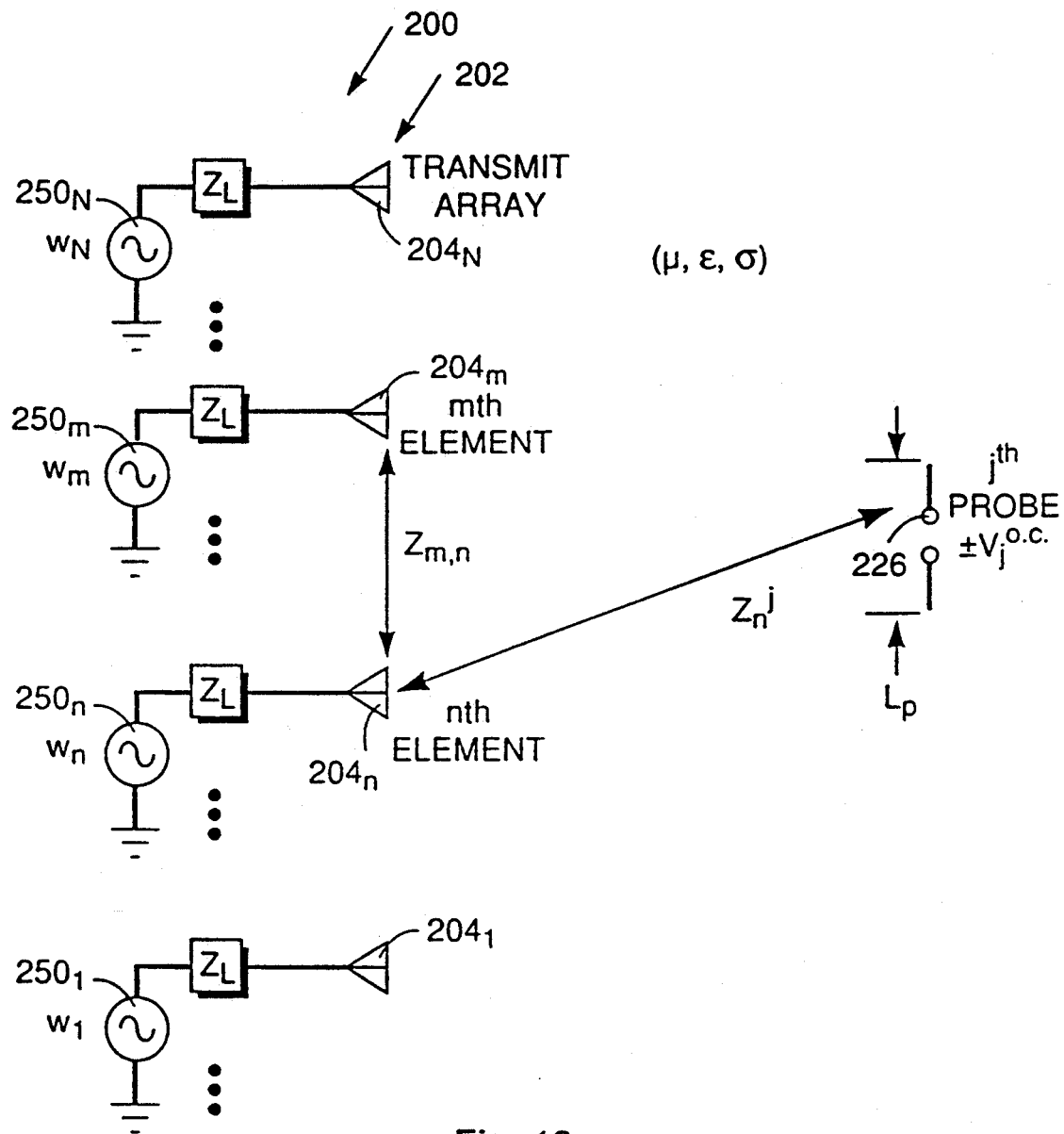
FIG. 13 is a schematic diagram of the analytical model of FIG. 7 redrawn to simplify derivation of method of moments analysis.

Referring to FIG. 13, there is shown the hyperthermia phased-array antenna system 200 of FIG. 7, redrawn to simplify the following method of moments analysis. The RF source 208, power divider 209 and weights $210_n$ of FIG. 7, are modeled as a plurality of RF signal generators $250_1$ through $250_N$, feeding its corresponding transmit antenna element $204_1$ through $204_N$. Each generator $250_1$ through $250_N$ has a corresponding amplitude and phase weight denoted by $w_1$ through $w_N$, and a known output impedance $Z_L$. The jth probe 226 (i.e., the same as the ith probe 226 of FIG. 7, with different notation) is modeled as a dipole antenna having an overall length $L_p$ and an open-circuit voltage $v_j^{o.c.}$ induced by the RF energy transmitted from the antenna array 200.

The open-circuit voltage at the jth probe antenna 226 is computed from the array terminal currents and from $Z_n^j$ the open-circuit mutual impedance between the nth array element and the jth probe antenna. Let $v_{nj}^{o.c.}$ represent the open-circuit voltage at the jth probe due to the nth transmit-array element. Here, the jth probe can denote either the focal point calibration probe (calibration probe 212 of FIG. 7) or one of the auxiliary probes used to null a sidelobe. The number of auxiliary probes is denoted by $N_{aux}$.

Figure 14:
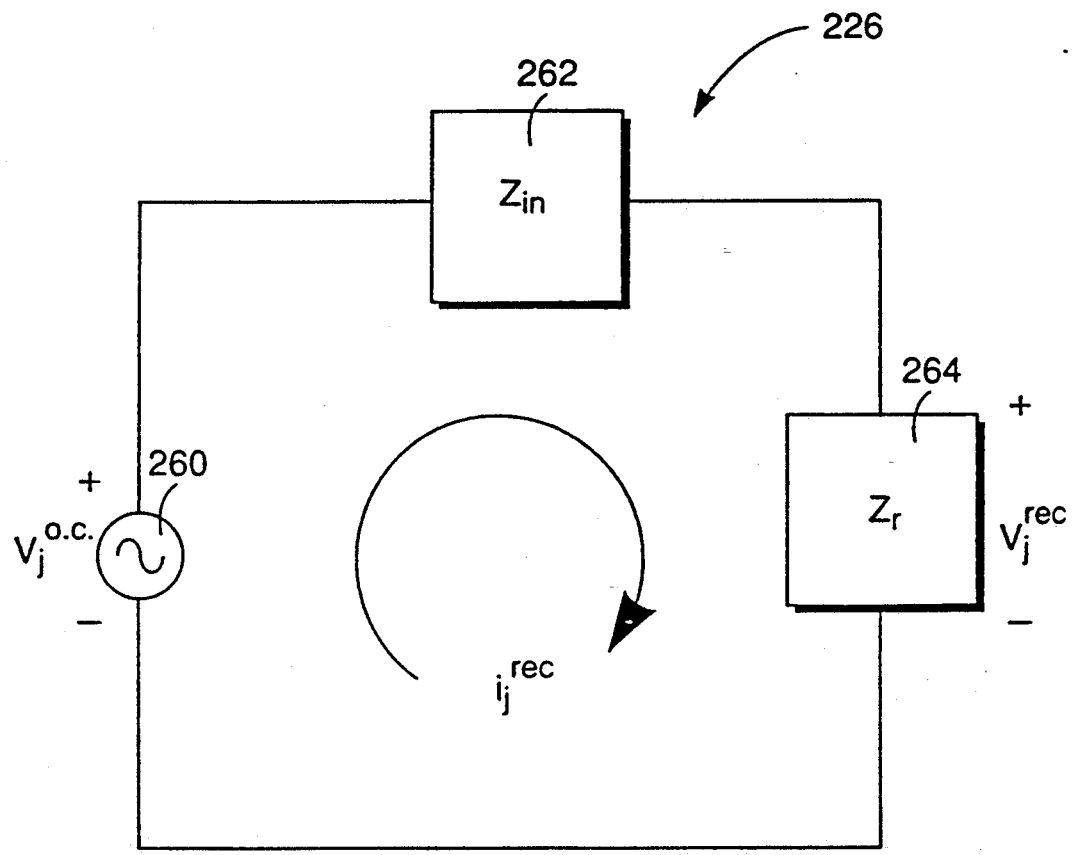
FIG. 14 is a schematic diagram of an equivalent circuit model for simulating an auxiliary probe.

Referring also to FIG. 14, the jth probe 226 is modeled as a voltage source 260, having an output voltage $v_j^{o.c.}$, driving a first impedance 262, representing the input impedance $Z_{IN}$ of the jth probe, in series with a second impedance 264, representing the termination impedance $Z_r$ of the jth probe. The jth probe receive current $i_j^{rec}$ flows through these two impedances. The output voltage of the jth probe $v_j^{rec}$ appears across the termination impedance $Z_r$.

Referring again to FIG. 13, next, let Z denote the open-circuit mutual impedance matrix (with dimensions N X N for the N-element array). The open-circuit mutual impedance between array elements $204_m$ and $204_n$ is denoted $Z_{m,n}$. It is assumed that multiple interaction between the hyperthermia array and the auxiliary probe can be neglected. Thus, the hyperthermia array terminal current vector i can be computed in terms of the transmit weights w as $$i=[Z+Z_L I]^{-1} w. \tag{36}$$

Next, let $Z_n^j$ be the open-circuit mutual impedance between the jth probe and the nth array element. The induced open-circuit voltage $v_{nj}^{o.c.}$ at the jth receive probe, due to the nth array element transmit current $i_n$, can then be expressed as $$V_{nj}^{o.c.}=Z_n^j \cdot i_n \tag{37}$$

In matrix form, the induced open-circuit probe-voltage matrix $v_{probe}^{o.c.}$ is $$V_{probe}^{o.c.}=Z_{probe,array} i \tag{38}$$

or $$V_{probe}^{o.c.}=Z_{probe,array}[Z-Z_L I]^{-1} W \tag{39}$$

where $Z_{probe,array}$ is a rectangular matrix of order $N_{aux}$ X N for the open-circuit mutual impedance between the probe array and the hyperthermia array. Note that the jth row of the matrix $Z_{probe,array}$ is written as ($Z_1^j$, $Z_2^j$, ..., $Z_N^j$), where j=1,2, ..., $N_{aux}$. The receive voltage matrix is then computed by the receiving circuit equivalence theorem for an antenna. The receive-antenna equivalent circuit is depicted in FIG. 14, where it is readily determined that $$v_{probe}^{rec} = v_{probe}^{o.c.} \frac{Z_r}{Z_{in} + Z_r} \tag{40}$$

where $Z_{in}$ is the input impedance of the probe. It should be noted that the $v_{probe}^{rec}$ matrix is a column vector of length $N_{aux}$ and $v_j^{rec}$ is the jth element of the matrix. The probe-receive current matrix is given by $$i_{probe}^{rec} = v_{probe}^{o.c.} \frac{1}{Z_{in} + Z_r} \quad (41)$$

The jth element of the column vector $i_{probe}^{rec}$ is denoted $i_j^{rec}$, $j=1,2,\ldots,N_{aux}$. Finally, the power received by the jth probe is $$p_j^{rec} = \tfrac{1}{2} Re(v_j^{rec} \cdot i_j^{rec*}) \quad (42)$$

where Re means real part. Substituting Equations (40) and into Equation (42) yields $$p_j^{rec} = \frac{1}{2} |v_j^{o.c.}|^2 \frac{Re(Z_r)}{|Z_{in} + Z_r|^2} \quad (43)$$

The total interference power received by the auxiliary probe array is given by $$p^{rec} = \sum_{j=1}^{J_{aux}} p_j^{rec} \quad (44)$$

The incident electric field E is related to the open-circuit voltage $v^{o.c.}$ by the effective height h of the probe antenna as $$v^{o.c.} = hE \quad (45)$$

If the length $L_p$ of the probe antenna 226 is approximately $0.1\lambda$ or less, the current distribution is triangular and the effective height is $h=0.5L_p$. Thus, for a short-dipole probe the open-circuit voltage can be expressed as $$v^{o.c.} = \frac{L_p}{2} E \quad (46)$$

It then follows from Equation (46) that the E field for a short-dipole probe at position (x,y,z) is given by $$E(x,y,z) = \frac{2v^{o.c.}(x,y,z)}{L_p} \quad (47)$$

Finally, the quiescent and adapted E-field radiation patterns are computed using the quiescent and adapted weight vectors $w_q$ and $w_a$, respectively, in Equations (39) and (47).

The moment-method expansion and testing functions are assumed to be sinusoidal. The open-circuit mutual impedances in Equation (39) between thin-wire dipoles in a homogeneous conducting medium are computed based on subroutines from the moment-method computer code developed by J. H. Richmond. In evaluating $Z_r^j$ for the jth auxiliary probe, double precision computations are used.

As mentioned previously, the array is calibrated (phased focused) initially using a short dipole at the focal point. To accomplish this numerically, having computed $v_{focus}^{rec}$, the transmit array weight vector w will have its phase commands set equal to the conjugate of the corresponding phases in $v_{focus}^{rec}$. Transmit antenna radiation patterns are obtained by scanning (moving) a dipole probe with half-length 1 in the near-field and computing the receive probe-voltage response.

The received voltage matrix for the jth probe (denoted $v_j^{rec}$) is computed at K frequencies across the nulling bandwidth. Thus, $v_j^{rec}(f_1), v_j^{rec}(f_2), \ldots v_j^{rec}(f_K)$ are needed. For the purposes of this computer simulation, the impedance matrix is computed at K frequencies and is inverted K times. The probe channel correlation matrix elements are computed by evaluating Equation (2) numerically, using Simpson's rule numerical integration. For multiple auxiliary probes, the channel correlation matrix is evaluated using Equation (4). Adaptive array radiation patterns are computed by superimposing the quiescent radiation pattern with the weighted sum of auxiliary-channel-received voltages.

Wave Propagation in Conducting Media

To gain insight into the effect of a lossy medium, e.g., the target body, on the propagation of an electromagnetic wave, it is useful to review certain fundamental equations which govern the field characteristics. In a conducting medium, Maxwell's curl equations in time-harmonic form are $$\nabla \times H = J + j\omega\epsilon E \quad (48)$$

and $$\nabla \times E = -j\omega\mu H \quad (49)$$

where E and H are the electric and magnetic fields, respectively, J is the conduction current density, $\omega = 2\pi f$ is the radian frequency, $\epsilon$ is the permittivity of the medium, and $\mu$ is the permeability of the medium. The permittivity is expressed as $\epsilon = \epsilon_r \epsilon_o$, where $\epsilon_r$ is the dielectric constant (relative permittivity) and $\epsilon_o$ is the permittivity of free space. Similarly, $\mu = \mu_r \mu_o$, where $\mu_r$ is the relative permeability and $\mu_o$ is the permeability of free space. For a medium with electrical conductivity $\sigma$, J and E are related as $$J = \sigma E \quad (50)$$

Substituting Equation (50) into Equation (48) yields $$\nabla \times H = (\sigma + j\omega\epsilon) E \quad (51)$$

From Equations (48) and (49), the vector wave equation in terms of E is derived as $$\nabla^2 E - \gamma^2 E = 0 \quad (52)$$

It is readily shown that $$\gamma = \pm \sqrt{j\omega\mu(\sigma + j\omega\epsilon)} = \pm j\omega \sqrt{\mu\epsilon} \sqrt{1 - j\frac{\sigma}{\omega\epsilon}} \quad (53)$$

The quantity $\sigma/\omega\epsilon$ is referred to as the loss tangent. It is common to express the complex propagation constant as $$\gamma = \alpha + j\beta \quad (54)$$

where $\alpha$ is the attenuation constant and $\beta$ is the phase constant. The constants $\alpha$ and $\beta$ are found by setting Equation (53) equal to Equation (54) and then squaring both sides, equating the real and imaginary parts, and solving the pair of simultaneous equations, with the result $$\alpha = \frac{\omega \sqrt{\mu\epsilon}}{\sqrt{2}} \left[ \sqrt{1 + \left(\frac{\sigma}{\omega\epsilon}\right)^2} - 1 \right]^{\frac{1}{2}} \quad (55)$$

The wavelength λ in the lossy dielectric is then computed from $$\beta = \frac{\omega \sqrt{\mu\epsilon}}{\sqrt{2}} \left[ \sqrt{1 + \left(\frac{\sigma}{\omega\epsilon}\right)^2} + 1 \right]^{\frac{1}{2}} \quad (56)$$

$$\lambda = \frac{2\pi}{\beta} \quad (57)$$

The intrinsic wave impedance η is given by $$\eta = \sqrt{\frac{j\omega\mu}{\sigma + j\omega\epsilon}} = \sqrt{\frac{\mu}{\epsilon}} \frac{1}{\sqrt{1 - j\frac{\sigma}{\omega\epsilon}}} \quad (58)$$

The instantaneous power density of the electromagnetic field is given by Poynting's vector, denoted P, $$P = \tfrac{1}{2} E \times H^* \quad (59)$$

which had units of (W/m²). The time-average power flow density is equal to the real part of the complex Poynting's vector. The time-average power dissipation per unit volume $P_d$ (W/m³) is derived from Maxwell's equations, with the result $$P_d = \tfrac{1}{2} E \cdot J^* = \tfrac{1}{2}\sigma |E|^2 \quad (60)$$

The specific absorption rate (SAR) is the power dissipated or absorbed per unit mass (W/kg) of the medium (tissue), or $$SAR = \frac{P_d}{\rho} = \frac{\sigma}{2\rho} |E|^2 \quad (61)$$

where ρ is the density of the medium in kg/m³.

It is convenient to have a simple equation for computing the propagation loss between any two points in the near field of an isolated transmitting antenna. Thus, mutual coupling effects are ignored for the time being. Consider a time-harmonic source radiating a spherical wave into an infinite homogeneous conducting medium. For an isotropic radiator, and suppressing the $e^{j\omega t}$ time dependence, the electric field as a function of range r can be expressed as $$E(r) = E_o \frac{e^{-\gamma r}}{r} \quad (62)$$

where $E_o$ is a constant.

For a source at the origin, the amplitude of the electric field at range $r_1$ is given by $$|E(r_1)| = E_o \frac{e^{-\alpha r_1}}{r_1} \quad (63)$$

and at range $r_2$ by $$|E(r_2)| = E_o \frac{e^{-\alpha r_2}}{r_2} \quad (64)$$

The total propagation loss between ranges $r_1$ and $r_2$ is found by taking the ratio of Equations (64) and (63), or $$\frac{|E(r_2)|}{|E(r_1)|} = \frac{r_1}{r_2} e^{-\alpha(r_2 - r_1)} \quad (65)$$

The field attenuation $A_\alpha$ in dB from range $r_1$ to range $r_2$ due to the lossy dielectric is simply $$A_\alpha = 20 \log_{10}(e^{-\alpha(r_2 - r_1)}) \quad (66)$$

Similarly, the 1/r attenuation loss $A_r$ in dB is $$A_r = 20 \log_{10} \frac{r_1}{r_2} \quad (67)$$

Thermal Modeling of an Inhomogeneous Target

A thermal analysis computer program called the transient thermal analyzer (TTA), developed by Arthur D. Little, Inc., has been used to accomplish the thermal modeling of homogeneous muscle tissue surrounded by a constant-temperature water bolus.

The TTA program uses the finite-difference technique to solve a set of nonlinear energy balance equations. Consider a system of interconnected nodes that model an inhomogeneous volume for which the temperature $T_i$ of the ith node is to be determined. The heat-balance equation, which is solved by TTA, is expressed as $$\sum_{i=1}^{N} Q_{i,j} - P_i(t) + M_i \frac{dT_i}{dt} = 0 \quad (68)$$

where $Q_{ij}$ is the net outward heat flow from node i in the direction of node j, $P_i(t)$ is the power into node i at time t, and $M_i$ is the thermal mass (mass times specific heat) of node i.

Figure 15:
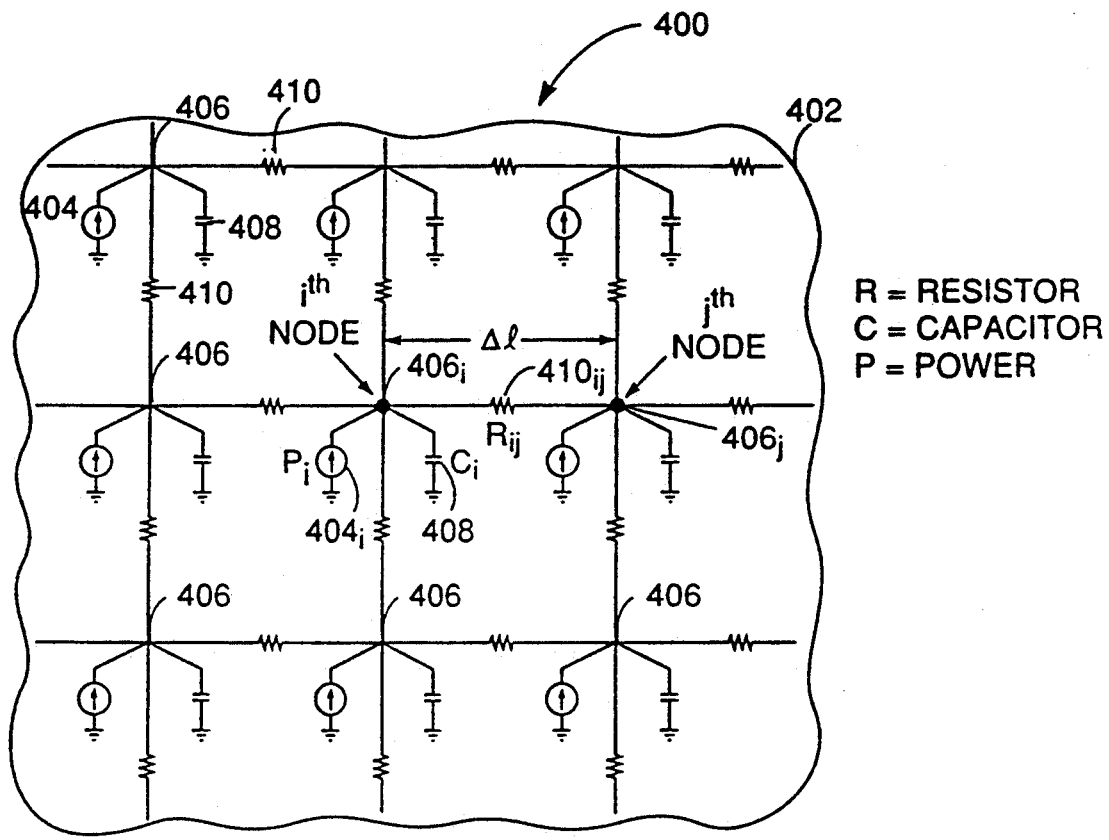
FIG. 15 is a schematic diagram of a thermal conductivity model for simulating hyperthermia heating within a target.

FIG. 15 shows an electric circuit analog 400 which is used to model the two-dimensional thermal characteristics of the material volume 402 which simulates the target body as a plurality of uniformly distributed nodes 406 spaced Δ1 apart. With reference to the ith node 406$_i$, but applying generally to the other nodes, power $P_i$ in watts is delivered 404$_i$ to the ith node. Capacitor 408$_i$, having thermal capacitance denoted $C_i$ (with units Joules/°C.), is used to model the thermal capacitance at the ith node. Resistor 410$_{ij}$, having heat resistance denoted $R_{ij}$ (with units °C./W), is used to model the heat resistance between ith node 406$_i$ and the jth node 406$_j$.

With a spacing of Δ1 between nodes (assuming cubic cells), the values of $R_{ij}$, $C_i$ and $P_i$ are computed as $$R_{i,j} = \frac{1}{k_{i,j}\Delta l} \quad (69)$$

where $k_{ij}$ is the thermal conductivity (with units W/m°C.) between nodes i and j;

$$C_i = \rho_i C_{pi} (\Delta 1)^3 \quad (70)$$

where $C_{pi}$ is the specific heat at the ith node and $\rho_i$ is the density (kg/m³) at the ith node; and $$P_i = (SAR)_i \rho_i (\Delta l)^3 \qquad (71)$$

where $(SAR)_i$ is the SAR for the ith node, which is given by $$(SAR)_i = \frac{\sigma_i}{2\rho_i} |E_i|^2 \qquad (72)$$

where $\sigma_i$ is the electrical conductivity of the ith node and $|E_i|$ is the magnitude of the electric field delivered by the hyperthermia array to the ith node. It should be noted that in substituting Equation (72) into Equation (71), the density $\rho_i$ cancels. Thus, an equivalent approach to computing the power delivered to the ith node is written in terms of the time-average power dissipated per unit volume of the ith node (denoted $P_{di}$) as $$P_i = P_{di}(\Delta l)^3 \qquad (73)$$

Figure 16A:
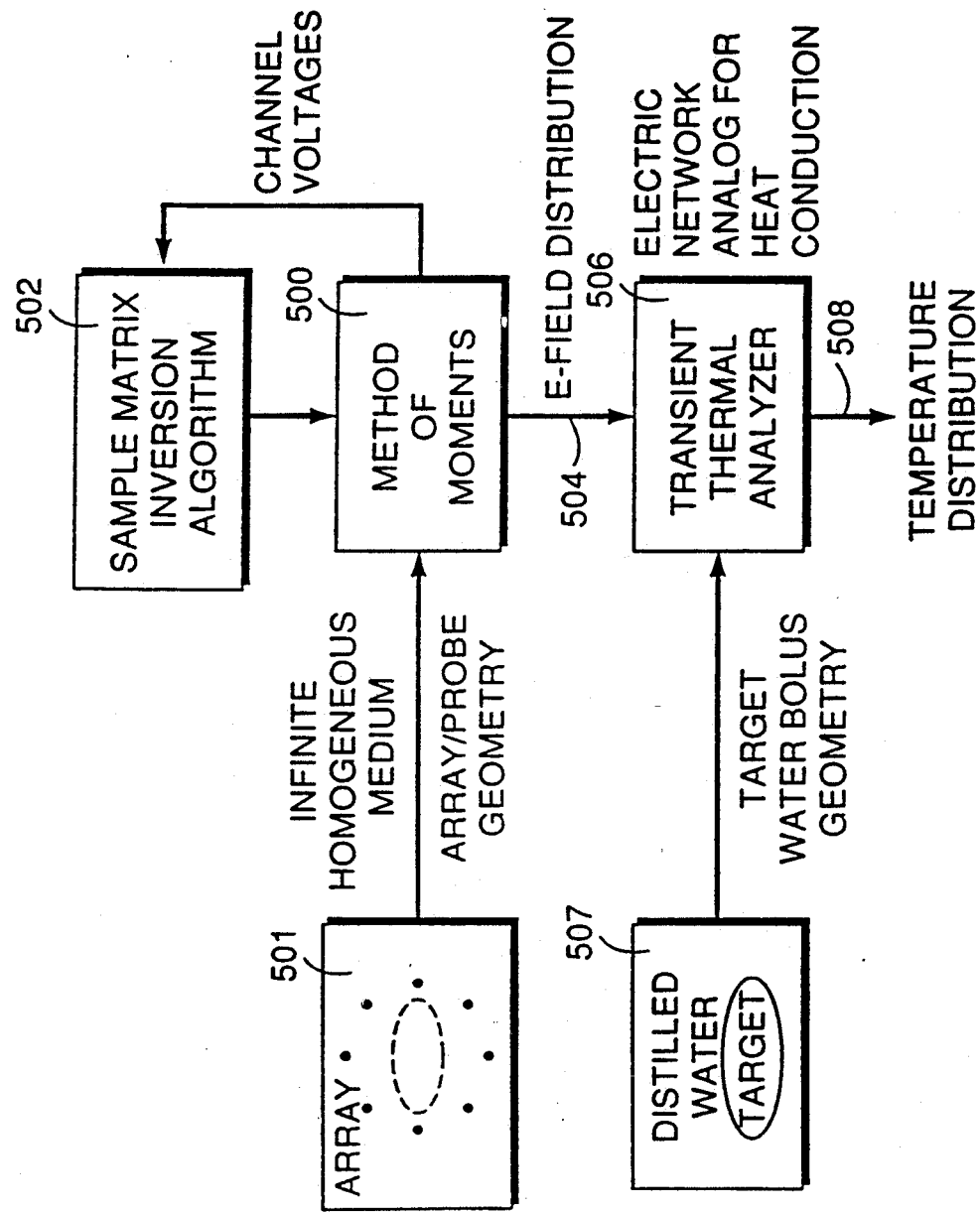
FIG. 16(a) is a block diagram detailing the simulation model of the hyperthermia array of FIG. 1.

FIG. 16 is a block diagram showing how TTA is used in the hyperthermia simulation described herein. First, the method of moments 500, controlled by the SMI nulling algorithm 502, is used to compute the electric field radiation pattern throughout a homogeneous region, simulating muscle tissue, inside an annular phased array 501. These E-field simulations assume that the signal received by a short-dipole probe within the region is due to a transmitting phased array embedded in an infinite homogeneous lossy dielectric (muscle tissue).

The resulting E-Field power distribution is then read 504 into the TTA program 506, which computes the temperature distribution inside an elliptical muscle-tissue target surrounded with a constant-temperature water bolus 507. Because the RF wavelengths in the target and water bolus are similar, the E-field simulations are believed to give a reasonable approximation to the field distribution inside the elliptical target. The computed temperature distribution is output 508 from the TTA for further analysis or display.

The E-field calculation in the assumed infinite homogeneous medium introduces additional field attenuation not present in a clinical hyperthermia system with an annular array transmitting through a water bolus into a patient. As mentioned earlier, the water bolus has very little RF propagation loss. In addition, the transmit array weights are normalized according to Equation (6). Thus, no attempt is made to compute the absolute E-field strength in volts/meter in the elliptical target. Instead, the peak power in the elliptical target is adjusted (by a scale factor) to produce a desired maximum focal-region temperature ($T_{max}$) after t minutes. It should be noted that an approximate absolute scale factor could be computed by making an initial computer simulation with an infinite homogeneous water bolus and then matching the target boundary field to the infinite homogeneous muscle tissue simulation.

The computer simulation model is related, in part, to the hyperthermia annular phased-array antenna system shown in FIG. 1. The simulated array is assumed to have a 60-cm array diameter with eight uniformly spaced dipole elements which operate over the frequency band 60–120 MHz. The eight elements of the array are assumed to be fully adaptive, whereby seven independent nulls can be formed while simultaneously focusing on a tumor.

It is further assumed for the purpose of this simulation that the adaptive radiation pattern null-width characteristics in a homogeneous target are similar to the characteristics observed in an inhomogeneous target. The null-width characteristics are directly related to the RF wavelength, and, only a 5 percent change in wavelength occurs between the assumed muscle tissue and water bolus. With this assumption, the transmit array may be simulated as embedded in homogeneous tissue, which allows direct use of the thin-wire moment-method formulation discussed above.

After computing the two-dimensional E-field distribution in the homogeneous medium, we then consider only an elliptical portion of the homogeneous region and use the ellipse as the homogeneous target. In the thermal analysis, the elliptical target is surrounded with a constant 10° C. water bolus. The E-field amplitude is scaled to produce a 46° C. peak temperature, at time t=20 minutes, at the center of the elliptical phantom. The initial temperature of the phantom is assumed to be 25° C. (room temperature).

All computer simulations assume a 120 MHz operating frequency with initially four auxiliary nulling probes, i.e., $N_{aux}=4$. The parameters used in the electrical and thermal analyses are summarized in Table 1. These parameters are for a frequency of 100 MHz, but is assumed that similar values of the parameters will exist at 120 MHz. It should be noted that although the relative dielectric constants of phantom muscle tissue and distilled water are very similar, the electrical conductivities are vastly different. The relevant thermal characteristics—density, specific heat, and thermal conductivity—are very similar for phantom muscle tissue and distilled water.

SIMULATION RESULTS

Electric Field for Array in Homogeneous Tissue

Substituting the values f=120 MHz, $\sigma=0.5$ S/m, and $\epsilon_r=73.5$ into Equation (53) yields $\gamma_m=10.0+j23.8$ for the muscle tissue. With $\beta_m=23.8$ radians/m, the wavelength in the phantom muscle tissue is $\lambda_m=26.5$ cm. The attenuation constant for the muscle tissue is $\alpha_m=10.0$ radians/m. Similarly, for distilled water $\gamma_w=0.0021+j22.5$, so the wavelength is $\lambda_w=27.9$ cm. The attenuation constant for the distilled water medium is $\alpha_w=0.0021$ radians/m. The propagation loss in the phantom muscle tissue is $20\log_{10}e^{-10.0}$, or $-0.87$ dB/cm. Similarly, the propagation loss in the distilled water is found to be $-0.0002$ dB/cm. Thus, the total loss due to propagation through 15 cm of distilled water is 0.003 dB. For 15 cm of muscle tissue the corresponding loss is 13.1 dB. The wave impedance in the muscle tissue is computed from Equation (58) as $\eta_m=33.9+j14.2\ \Omega$, and similarly in the distilled water $\eta_w=42.1+j0.004\ \Omega$.

Figure 17:
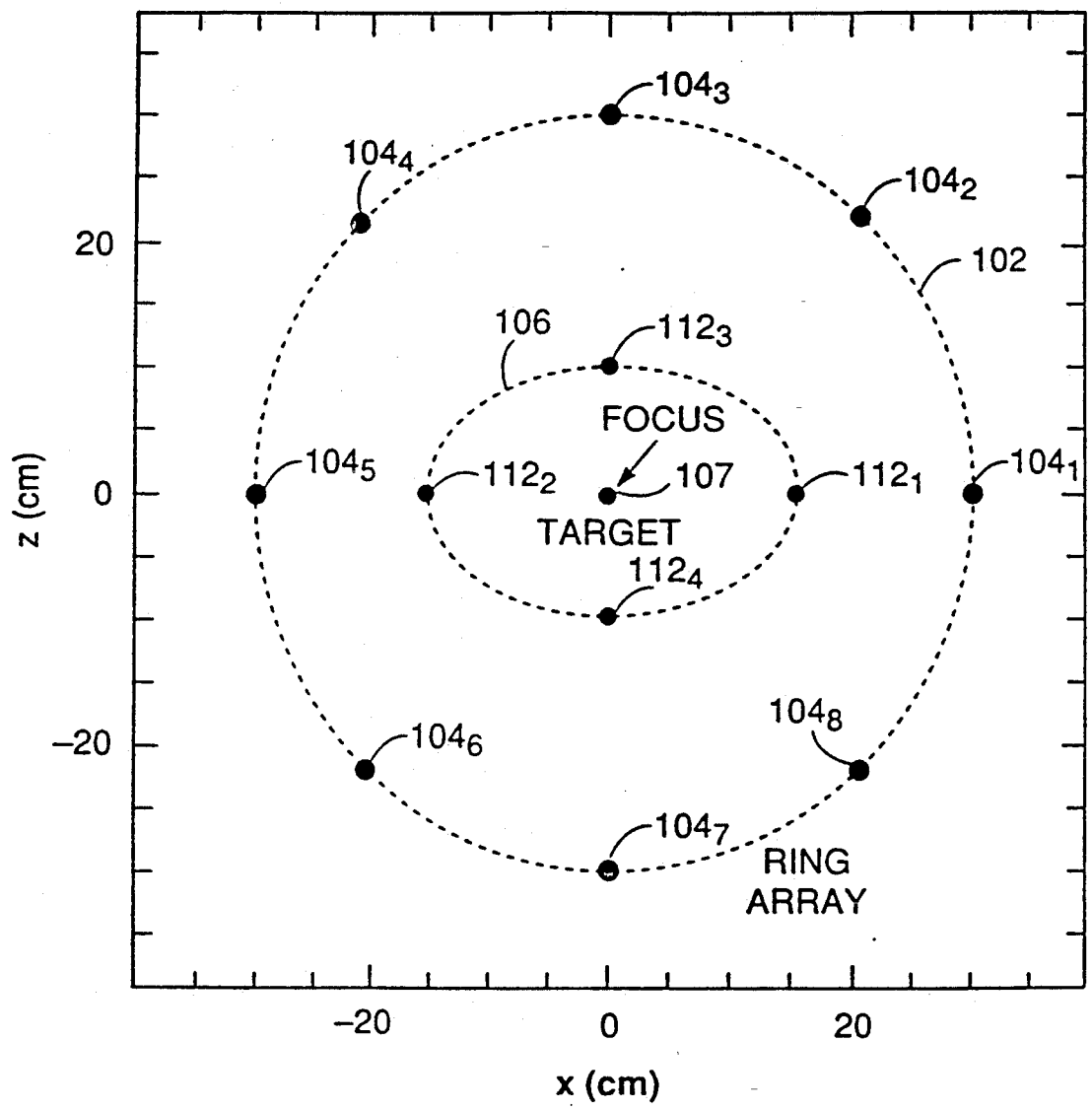
FIG. 17 is a schematic diagram of the transmit antenna array and auxiliary probe array geometries for the simulation model of FIG. 16(a).

FIG. 17 shows the geometry used in the simulations, which parallels the array shown in FIG. 3. A 60-cm-diameter ring array 102 of eight perfectly conducting center-fed dipoles, $104_1$ through $104_8$, uniformly surrounds a fictitious elliptical target zone 106 with major axis 30 cm and minor axis 20 cm. The length of each dipole array element $104_n$ at 120 MHz in the infinite homogeneous muscle tissue is $\lambda/2$, or 13.25 cm. The array focus 107 is assumed at the origin (x=0, y=0, z=0) and four auxiliary short-dipole probes, $112_1$ through $112_4$, with length 1.27 cm (0.05λ) are positioned at (x,y,z) coordinates at (15 cm, 0, 0), (−15 cm, 0, 0), (0, 0, 10 cm), and (0, 0, −10 cm), respectively, i.e., the auxiliary E-field probes are located every 90° in azimuth on the perimeter of the target. In rectangular coordinates, each dipole is oriented along the ŷ direction and the feed terminals of each dipole are located at y=0.

The moment-method computer simulations were run on a Sun 3/260 workstation. The total CPU time for a complete moment-method run is 19.2 minutes. This CPU time includes computing the quiescent and adaptive radiation patterns on a 41 by 41 grid of points. The CPU time without radiation pattern calculations is 33 seconds.

Figure 18:
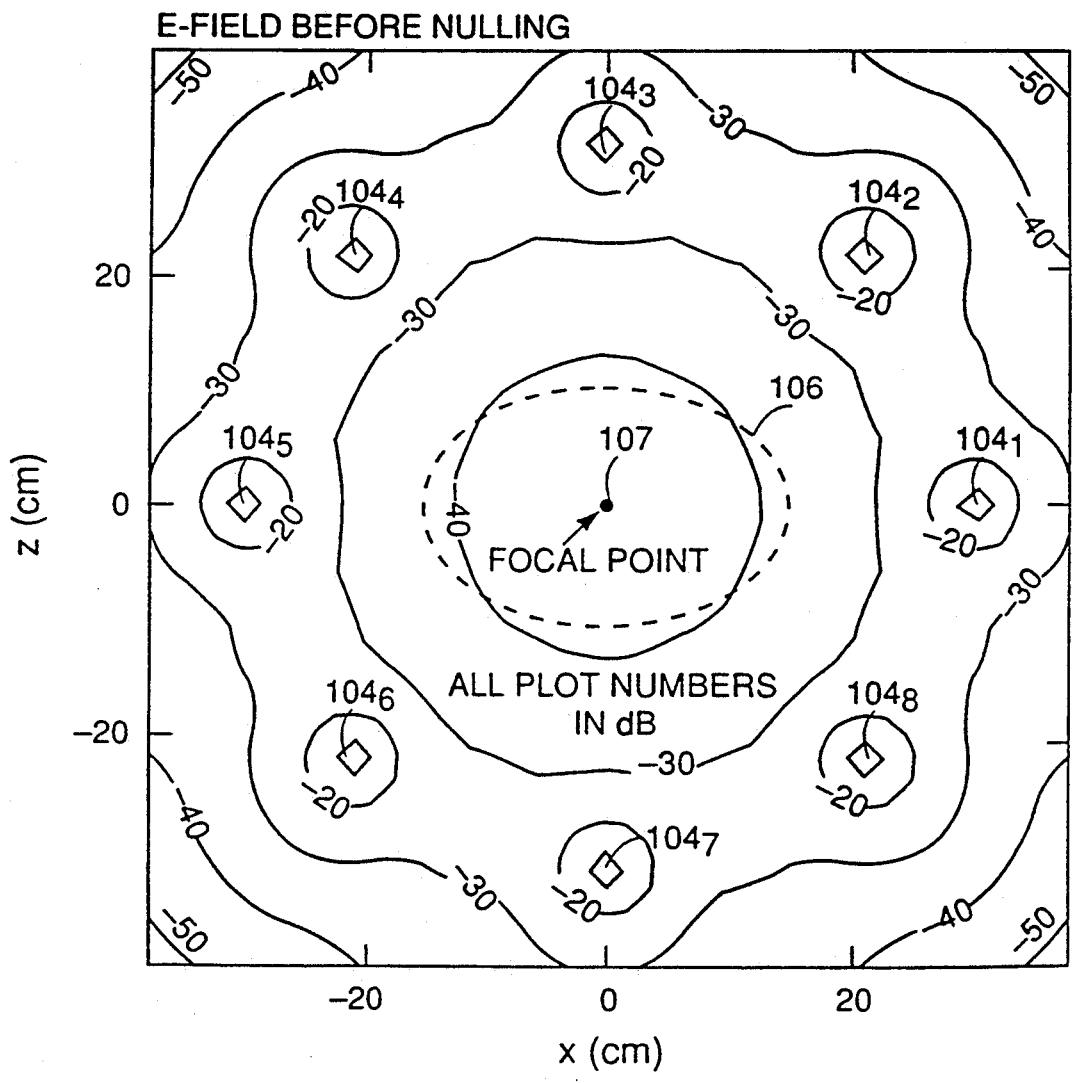
FIG. 18 is a diagram of the simulated E-field for the simulation model of FIG. 16(a) prior to adaptive nulling.

FIG. 18 shows the two-dimensional radiation pattern in the plane y=0, before nulling, at 120 MHz with uniform amplitude and phase illumination. The calculated data are collected on a 41 by 41 grid of points over a square region, with side length 76.2 cm, centered at the focus 107. The spacing between data points is 1.905 cm, or 0.072λ, and the contour levels are displayed in 10-dB steps. The E-field data are computed for the case of a 1.27-cm short-dipole observation probe. The positions of the eight dipole radiators $104_1$ through $104_8$ are clearly evident by the −20 dB contours surrounding each element. The radiation pattern is symmetric because of the symmetry of the array and the assumed homogeneous medium.

Figure 19:
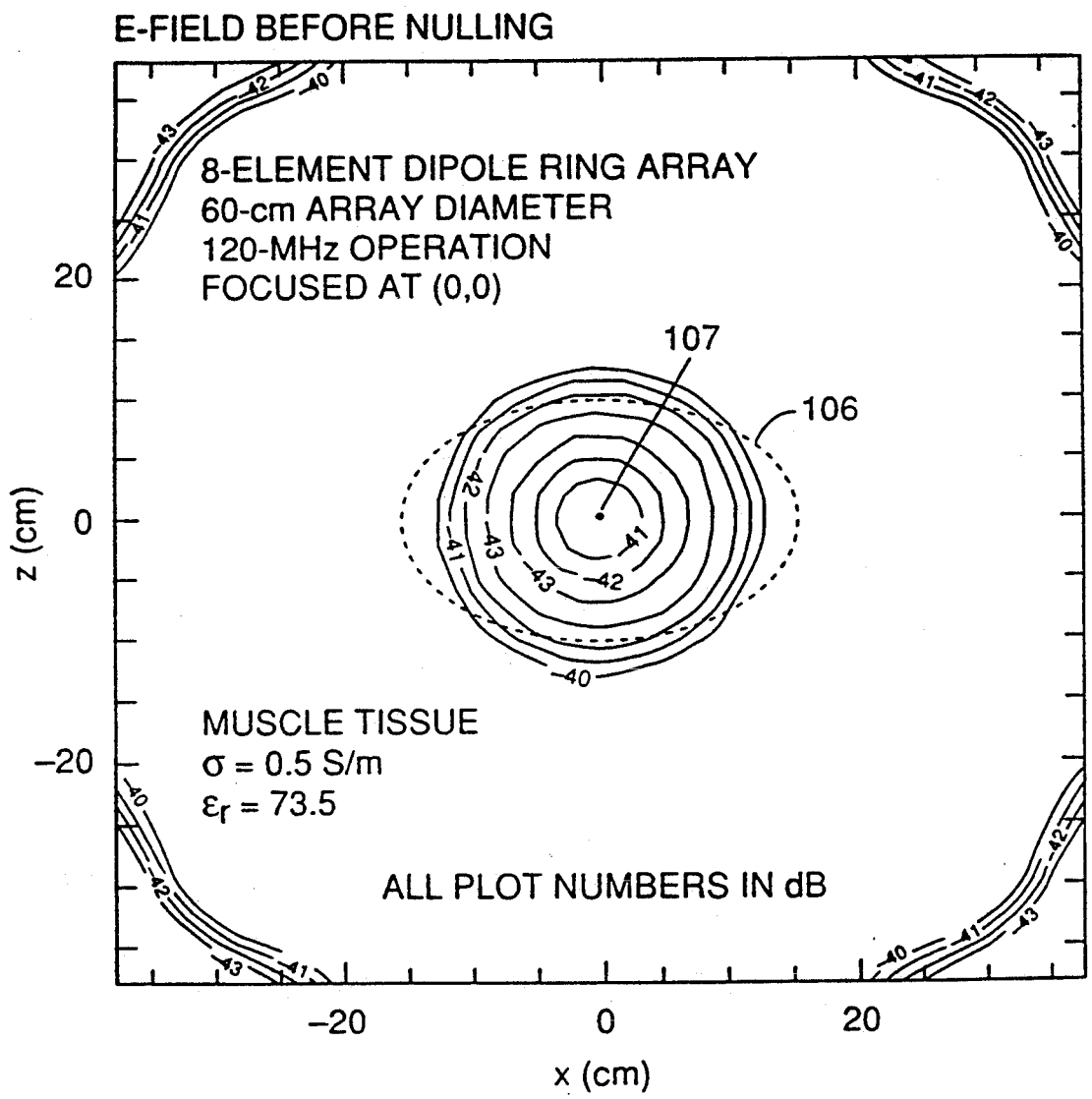
FIG. 19 is a diagram of the simulated temperature profile for the E-field of FIG. 18.

FIG. 19 shows finer contour levels (1-dB steps) for the quiescent radiation pattern of FIG. 18. Here, it is evident that the focused main beam of the ring array is increasing in amplitude as the observation point moves closer to the focus. Away from the main beam region, the pattern amplitude is seen to increase as the observation position moves toward the array perimeter.

Figure 20:
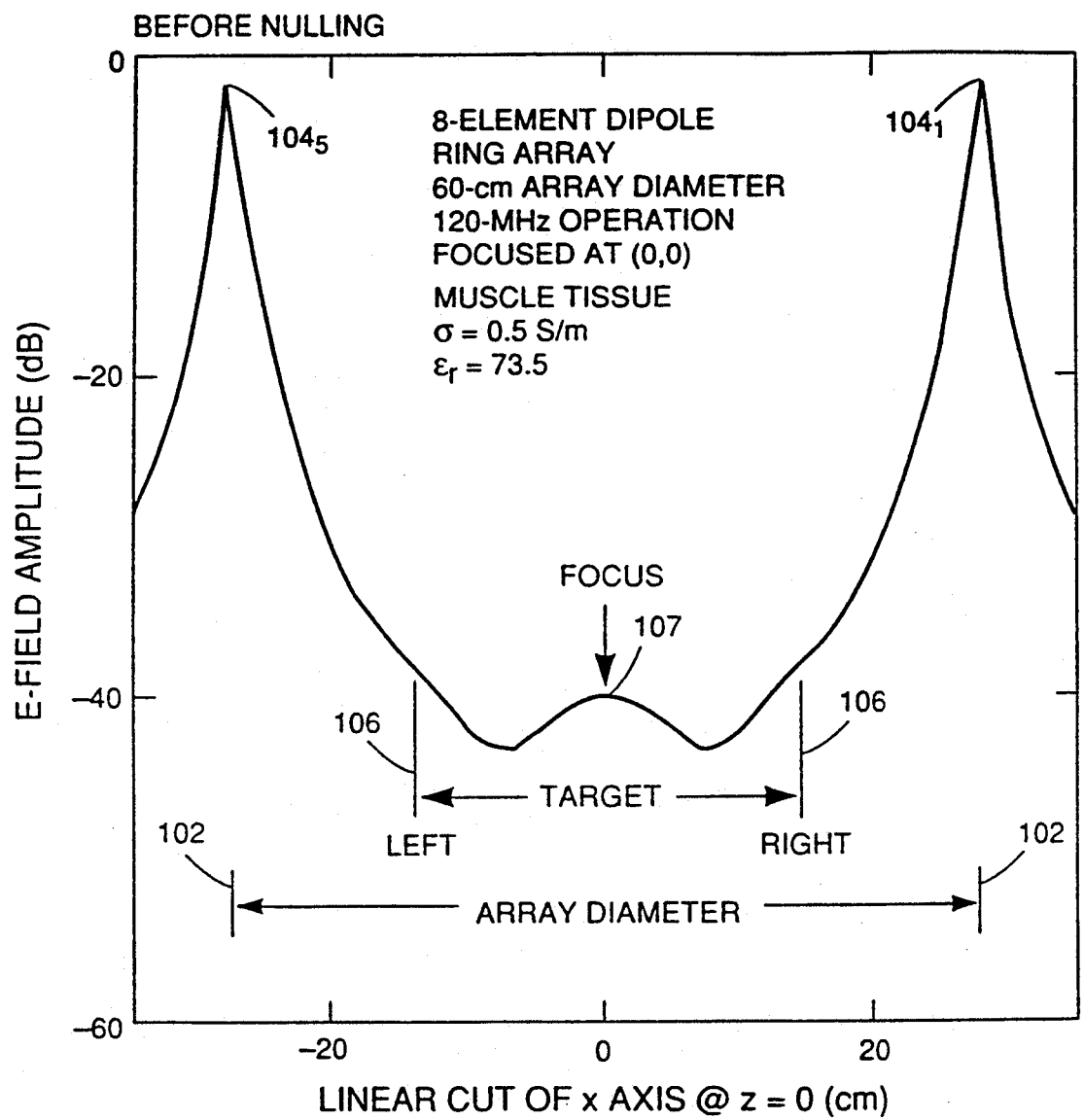
FIGS. 20 and 21 are diagrams of the simulated temperature profile of FIG. 19 taken along the x- and z-axis, respectively.
Figure 21:
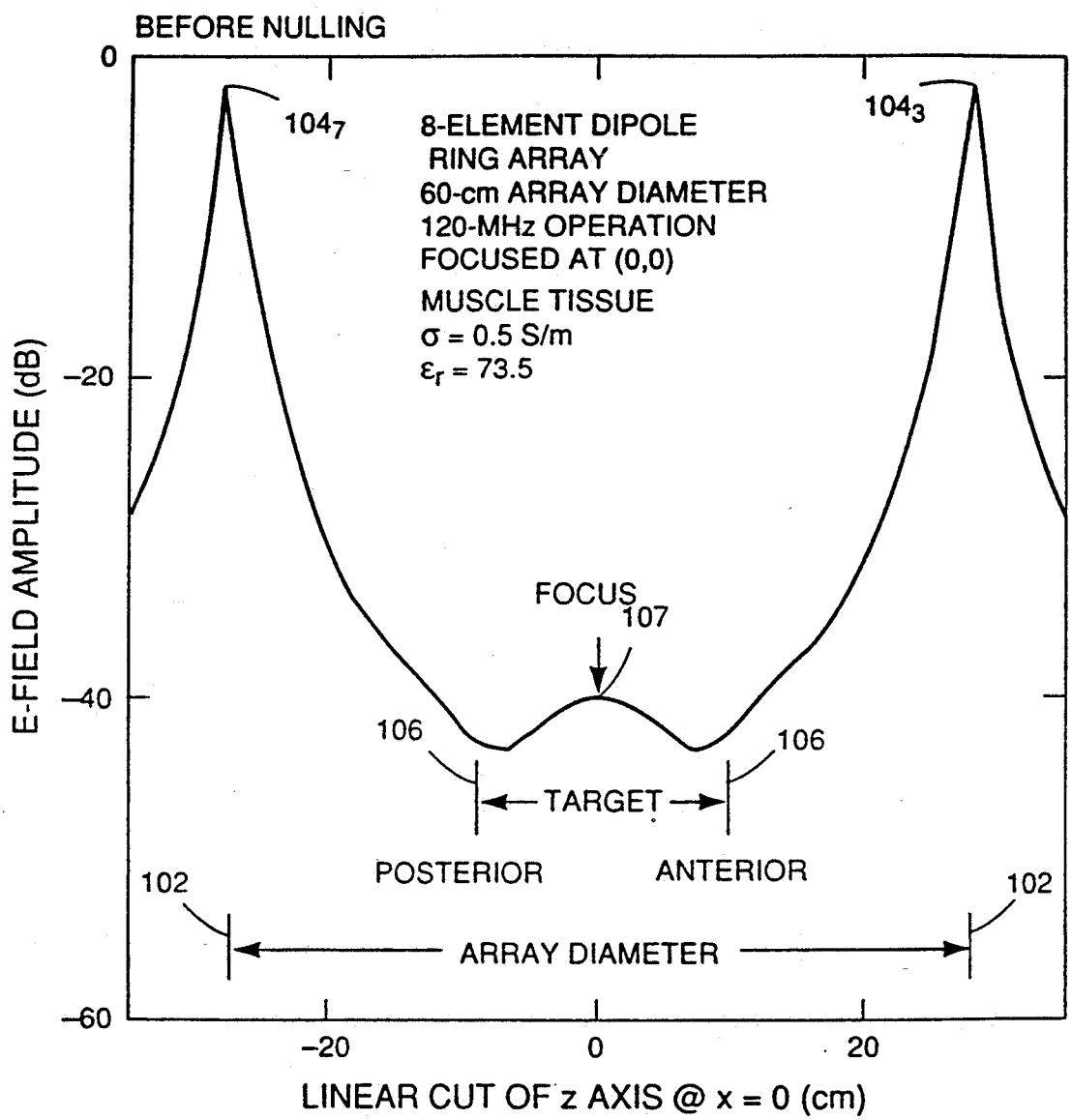

FIG. 20 shows the quiescent radiation pattern of FIG. 18 cut at z=0. The large amplitude that occurs at ±30 cm, i.e., at the position of the array 102, is due to the E-field probe's close proximity to the transmitting elements $104_1$ and $104_5$. The large attenuation that occurs from the array diameter to the focus is due to the 1/r attenuation loss and the loss in the uniform homogeneous muscle tissue. FIG. 21 shows the radiation pattern of FIG. 18 cut at x=0. Here, the pattern is identical to the pattern of FIG. 20 due to the symmetry of the array. In both FIGS. 20 and 21 the boundary of the fictitious elliptical target zone 106 is indicated. The target zone of FIG. 20 is larger than that of FIG. 21 since the major axis of elliptical target 106 lies along the x-axis, and the minor axis of target 106 lies along the Z-axis.

The increasing radiation pattern amplitude near the left and right sides of the elliptical target of FIG. 20 is shown to produce hot spots in the thermal distribution. Because the top (anterior) and bottom (posterior) of the elliptical target of FIG. 21 are not as strongly illuminated as to the left and right sides of the elliptical target of FIG. 20, no quiescent hot spots occur at the top or bottom.

Further, FIG. 20 shows that the ring-array half-power beamwidth in the target region is approximately 13 cm, or approximately one-half the wavelength (26.5 cm) in the phantom muscle tissue. The adaptive nulling resolution or closest allowed spacing between a deep adaptive null and the main beam has been shown to be equal to the half-power beamwidth of the antenna. Thus, the closest allowed null position is 13 cm from the focus. Since the target width is 30 cm across the major axis, two nulls can be formed at (x=±15 cm, z=0) at the left and right side of the target without disturbing the focus. However, if two deep nulls are formed at the posterior and anterior (x=0, z=±10 cm) of the target the focus will be compromised. In practice, the water bolus surrounding the target would restrict the placement of short-dipole probes $112_n$ to the surface of the target. Thus, only weak nulls can be formed at (x=0, z=±10 cm) so that the focus will not be affected by the adaptive nulling process. That is, the effect of the two minor axis nulls is to keep the z=±10 cm E-field from increasing beyond the quiescent values.

Next, adaptive radiation patterns are computed with four auxiliary dipole probes $112_1$ through $112_4$ positioned as shown in FIG. 17. The value of the receiving gain for auxiliary dipole probes $112_1$ and $112_2$ is adjusted to produce a SNR>35 dB. This amount of SNR results in greater than 35 dB of nulling in the direction of auxiliary dipole probes $112_1$ and $112_2$. In contrast, the gain values for auxiliary dipole probes $112_3$ and $112_4$ are turned down to produce about a 3 dB SNR. Thus, only about 3 dB of nulling will occur at probe positions $112_3$ and $112_4$ as the adaptive algorithm reduces the interference to the noise level of the receiver. The reason for choosing these null depths will become apparent with the data that follow.

Figure 22:
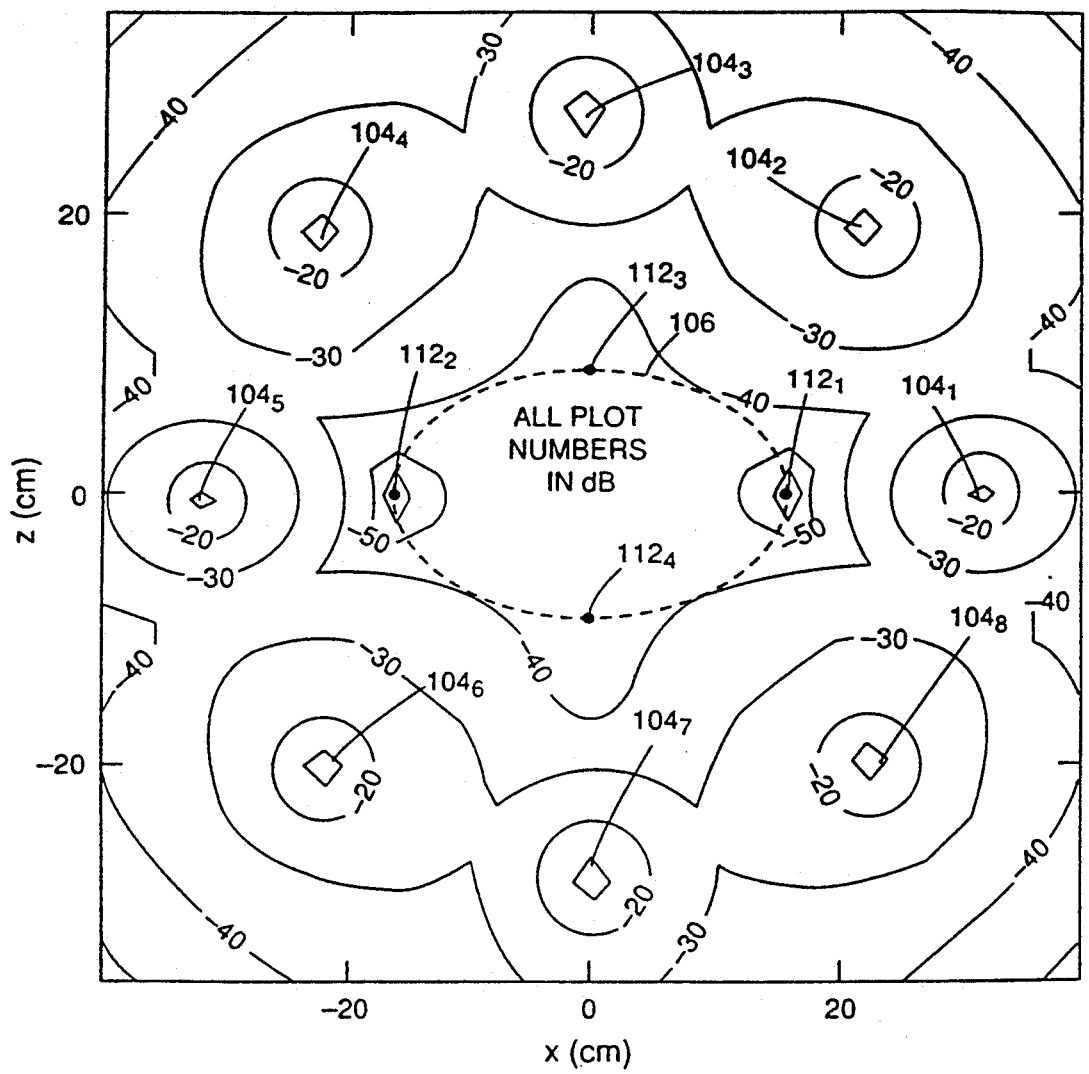
FIG. 22 is a diagram of the simulated E-field for the simulation model of FIG. 16(a) after adaptive nulling.

FIG. 22 shows the two-dimensional radiation pattern after nulling with four auxiliary probes $112_1$ through $112_4$. Two deep adaptive nulls at x=±15 cm occur as expected, and weak nulling occurs at z=±10 cm, also as expected.

Figure 23:
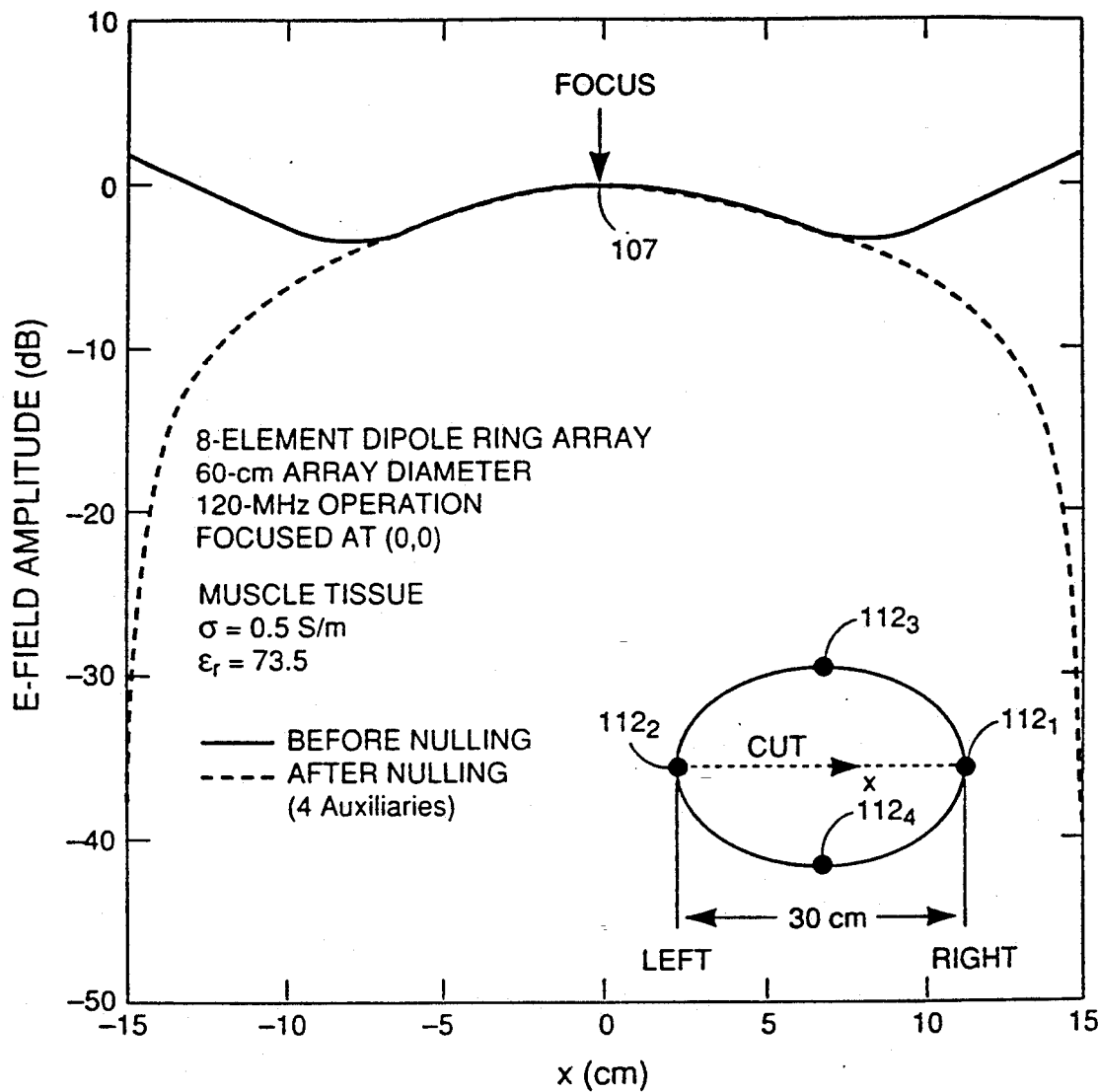
FIGS. 23 and 24 are diagrams of the simulated E-field of FIG. 22 taken along the x- and z- axis, respectively.
Figure 24:
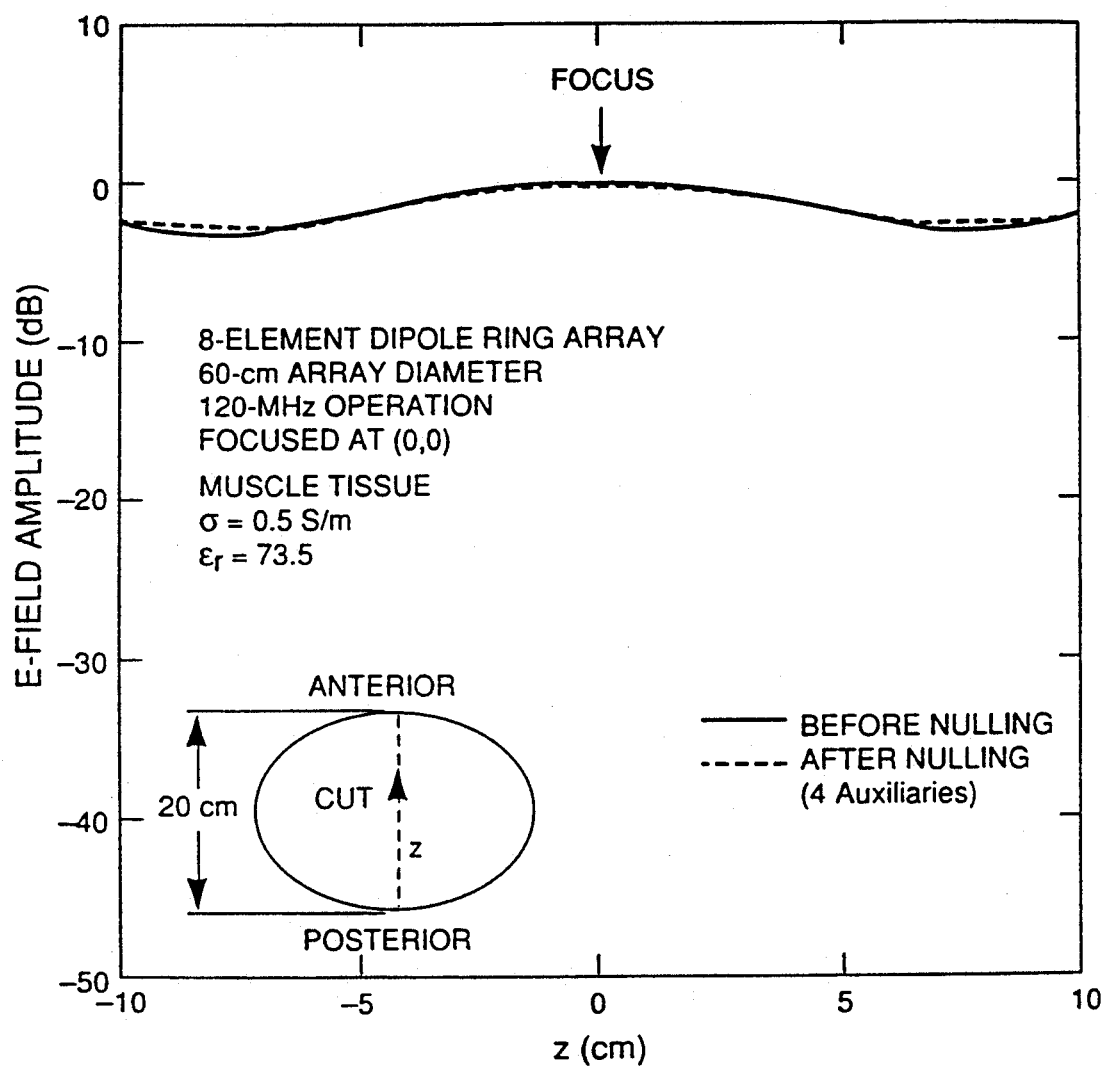

The two deep nulls in the z=0 cut are quantified in FIG. 23, where greater than 35 dB of interference nulling or pattern reduction occurs at x=±15 cm. The peak level at the focus 107 is adjusted to 0 dB for both the quiescent and adaptive patterns. Two weak adaptive nulls are seen in the x=0 radiation pattern cut shown in FIG. 24. The weak nulls in effect in the adaptive patterns reduce variation from the quiescent radiation pattern.

Figure 25A:
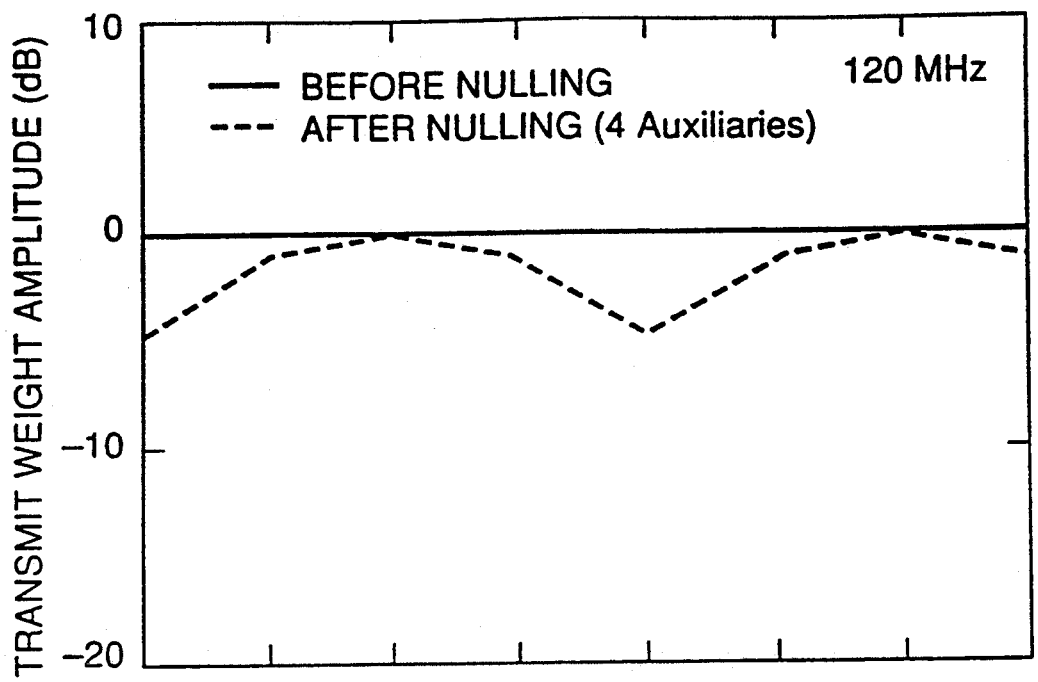
FIGS. 25(a) and 25(b) are graphs showing the transmit weight amplitude and phase, respectively, before and after adaptive nulling.
Figure 25B:
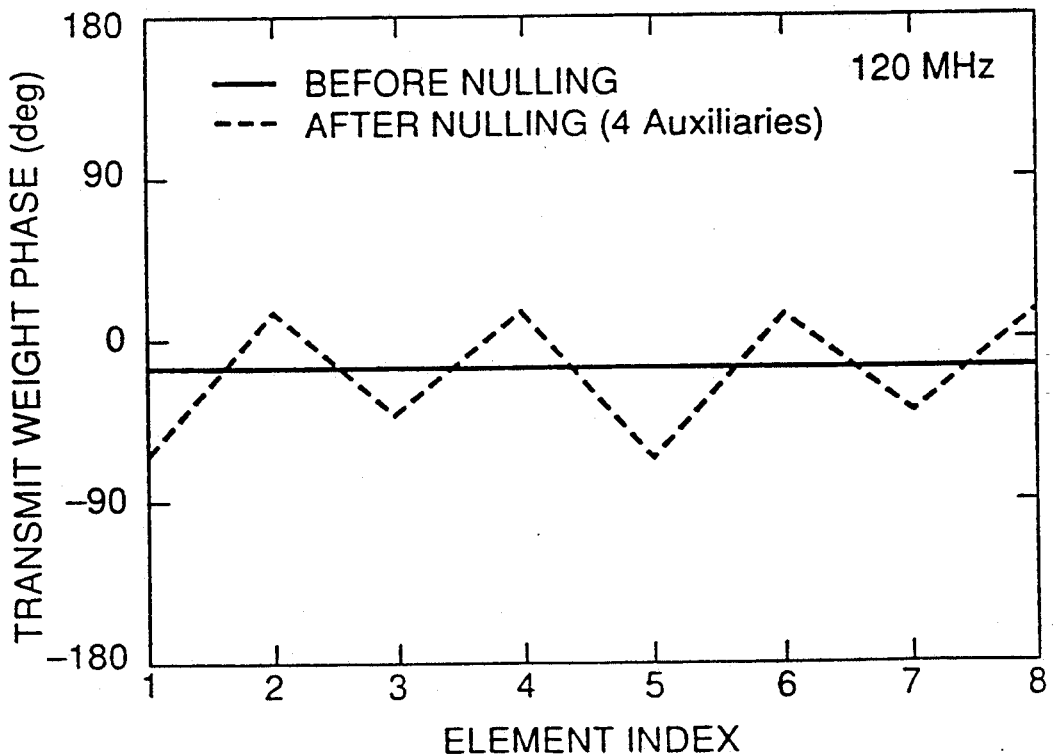

FIG. 25(a) shows the transmit array amplitude weights before (solid line) and after (broken line) nulling, and FIG. 25(b) shows the transmit array phase weights before (solid line) and after (broken line) nulling. As shown, the adaptive transmit weights exhibit a 5-dB dynamic range in FIG. 25(a).

Figure 26:
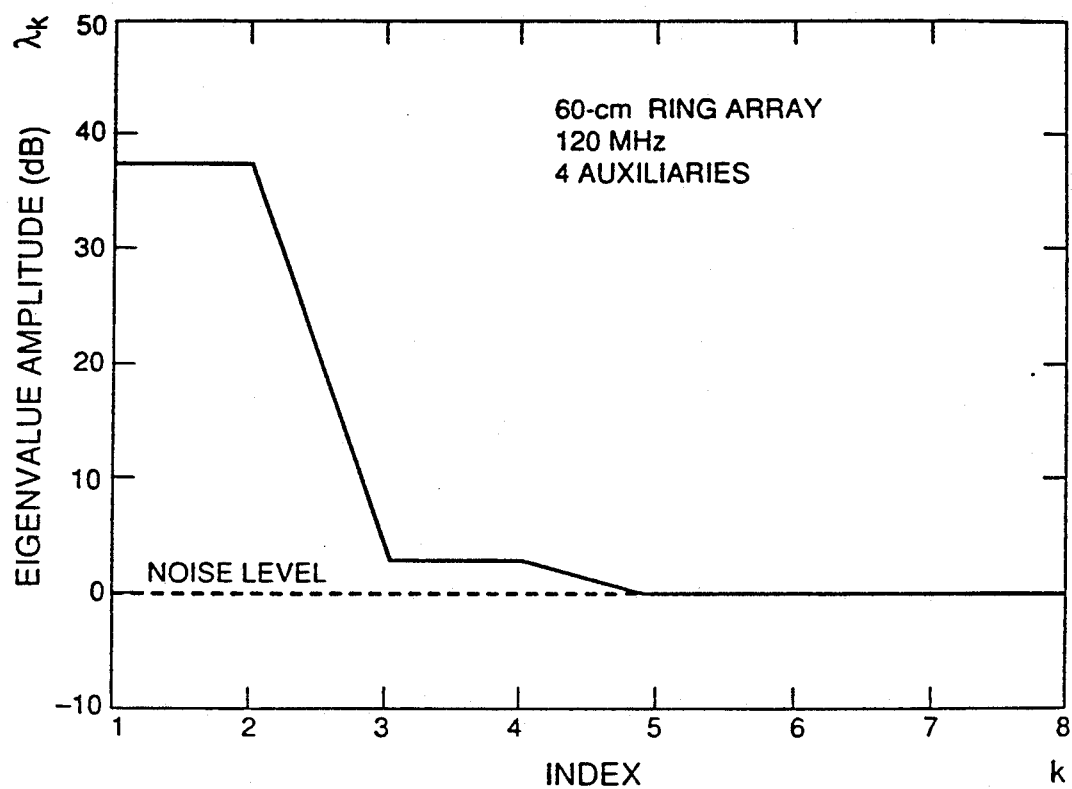
FIG. 26 is a graph showing the channel correlation matrix eigenvalues.

FIG. 26 shows the channel correlation matrix eigenvalues before (solid line) and after (broken line) nulling. There are two large eigenvalues, $\lambda_1$ and $\lambda_2$, and two weak (non-zero) eigenvalues, $\lambda_3$ and $\lambda_4$, shown in FIG. 26. These eigenvalues are directly associated with the two high-SNR auxiliary probes $112_1$ and $112_2$, and the two weak-SNR auxiliary probes $112_3$ and $112_4$, respectively. Note that the 0-dB level in FIG. 26 is equal to the receiver noise level. The probe-array output power before and after adaptive nulling is 31.4 dB and 0.9 dB, respectively, as calculated from equation (10). This difference in power before and after nulling indicates that the adaptive cancellation is −30.5 dB.

Temperature Distribution in Elliptical Phantom

To simulate the temperature distribution in the target body resulting from the calculated E-fields, the transient thermal analysis (TTA) software is used to compute the temperature distribution in an elliptical phantom surrounded with a constant-temperature water bolus. The 41×41 two-dimensional E-field radiation pattern data of FIGS. 18 through 24 are used as the power source for the thermal node network. Two node spacings are considered. First, the node spacing $\Delta x = \Delta z = \Delta 1 = 1.905$ cm (coarse grid) is used to obtain thermal data. Then, the node spacing is decreased by a factor of two to $\Delta 1 = 0.9525$ cm (fine grid) to check convergence. The coarser spacing is shown to be adequate.

Figure 27:
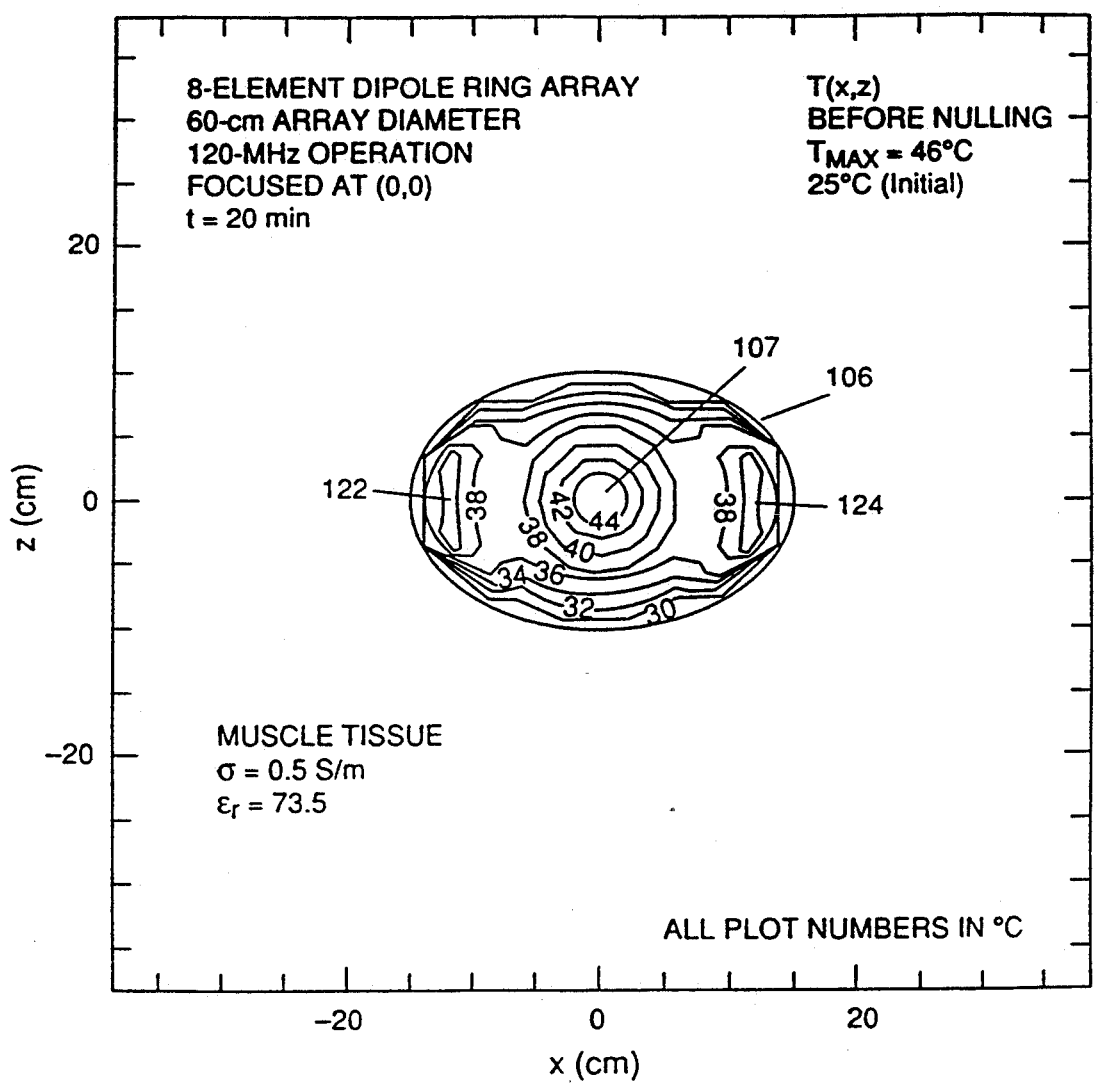
FIG. 27 is a diagram of the simulated target temperature profile for the E-field of FIG. 18 prior to adaptive nulling.
Figure 28:
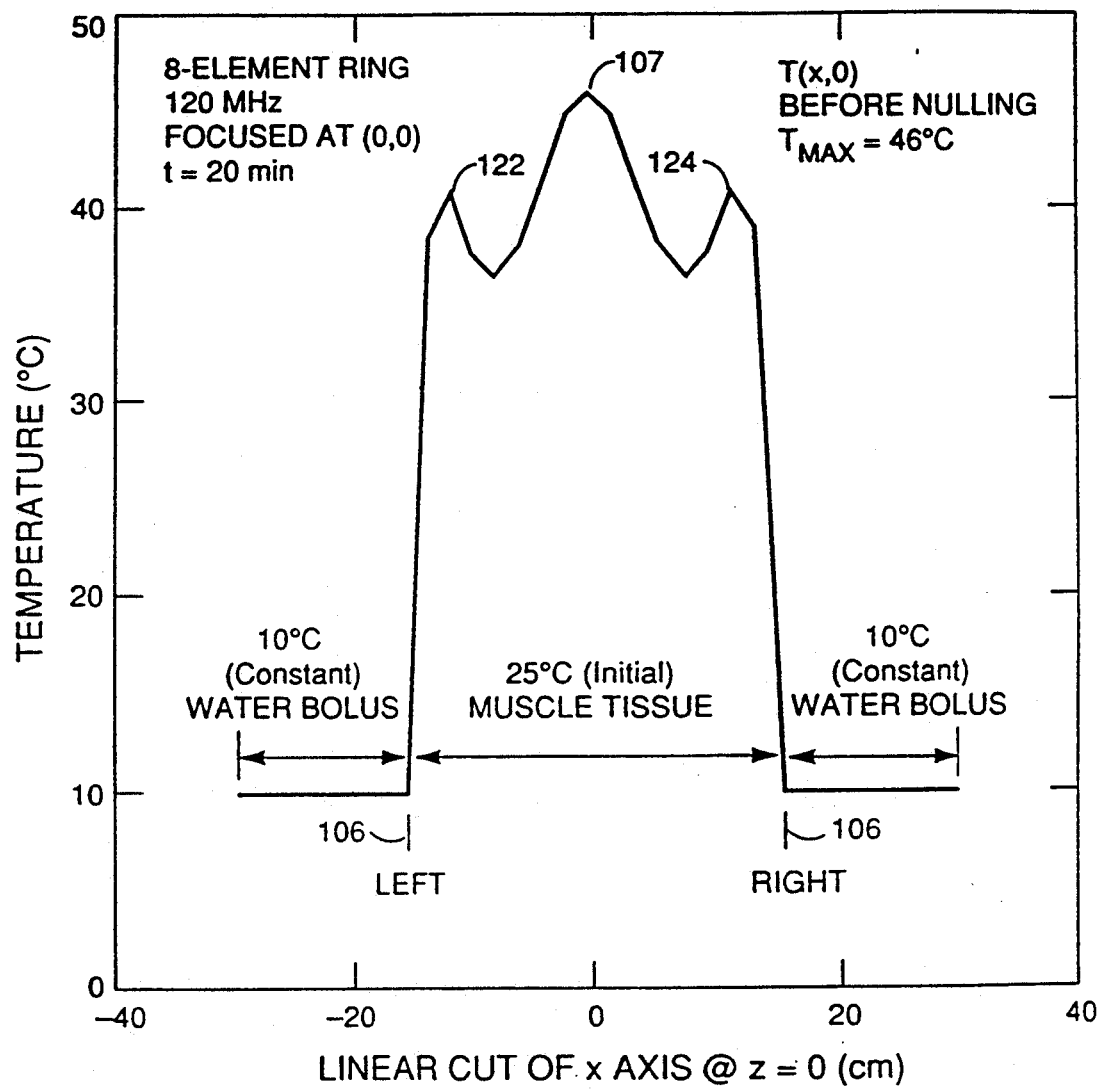
FIGS. 28 and 29 are diagrams of the temperature profile of FIG. 27 taken along the x- and z- axis, respectively.
Figure 29:
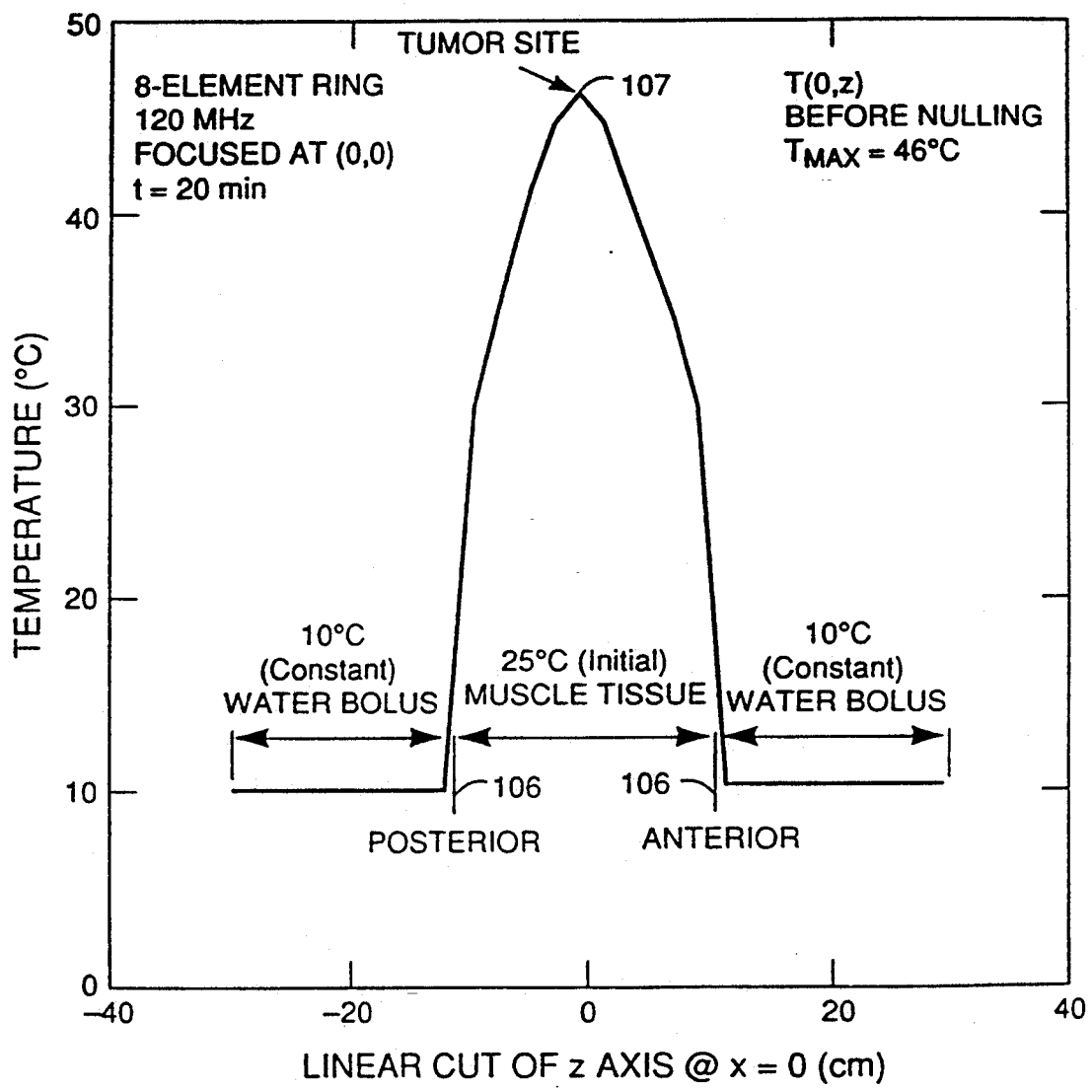

The scale factors used to convert the normalized E-field distributions to a power level that induces a 46° C. peak temperature at t=20 minutes are 94.1 dB and 96.0 dB for the quiescent and adaptive patterns, respectively. These scale factors are determined empirically. From Equations (68) through (73) and the parameter values given in Table 1, all resistors $R_{ij}$ in the phantom muscle tissue had a value of 96.5° C./W and all resistors $R_{ij}$ in the water bolus had a value of 87.2° C./W. The value of the capacitors $C_i$ in the phantom muscle tissue is 23.6 J/°C. Capacitors are not used in the water-bolus region in the input to the transient thermal analysis software. Instead, a constant temperature of 10° C. is enforced at each water-bolus node. With a 41×41 grid, a total of 3280 resistors and 1681 capacitors are used in the thermal simulation. The CPU time required to compute this temperature distribution is under four minutes. FIG. 27 shows the two-dimensional temperature distribution produced at time t=20 minutes in the elliptical phantom muscle tissue target 106 without adaptive nulling. To generate FIG. 27, the power source used in the transient thermal analysis is the quiescent radiation pattern given in FIG. 18. The initial temperature (at time t=0) is 25° C. Notice the occurrence of two hot spots 122 and 124 on the left and right sides of the elliptical phantom, respectively. The peak temperature at focus 107 is 46° C., which is achieved by scaling the normalized quiescent E-field as described earlier. The two hot spots 122 and 124 are quantified in the z=0 temperature pattern cut shown in FIG. 28, and have a peak temperature at each hot spot of approximately 41° C. The temperature profile for x=0 in FIG. 29 shows no hot spots. As any undesired hot spot is a potential source for compromising the therapy session, adaptive nulling is used to reduce the sidelobes corresponding to the hot spots.

Figure 30:
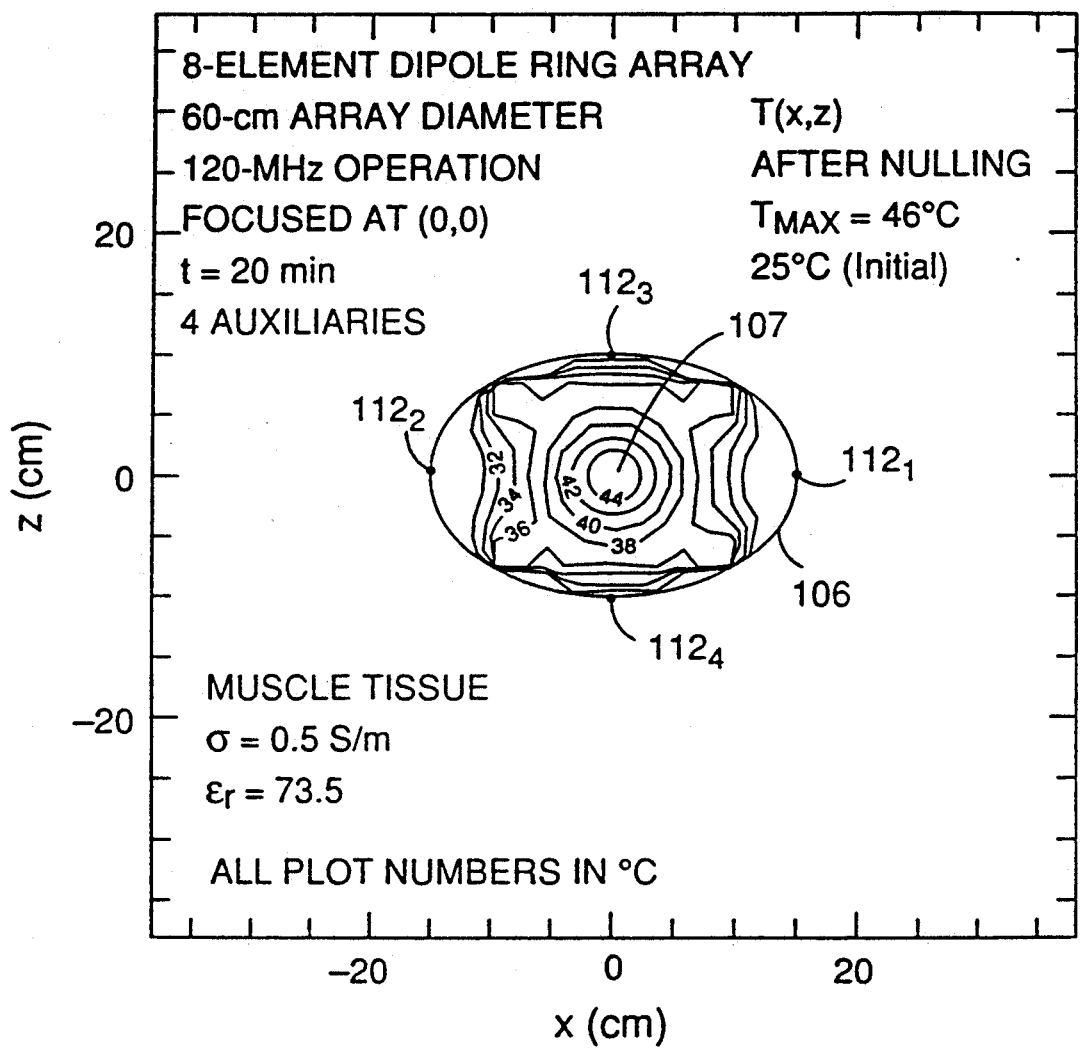
FIG. 30 is a diagram of the simulated target temperature profile for the E-field of FIG. 22 after adaptive nulling.
Figure 31:
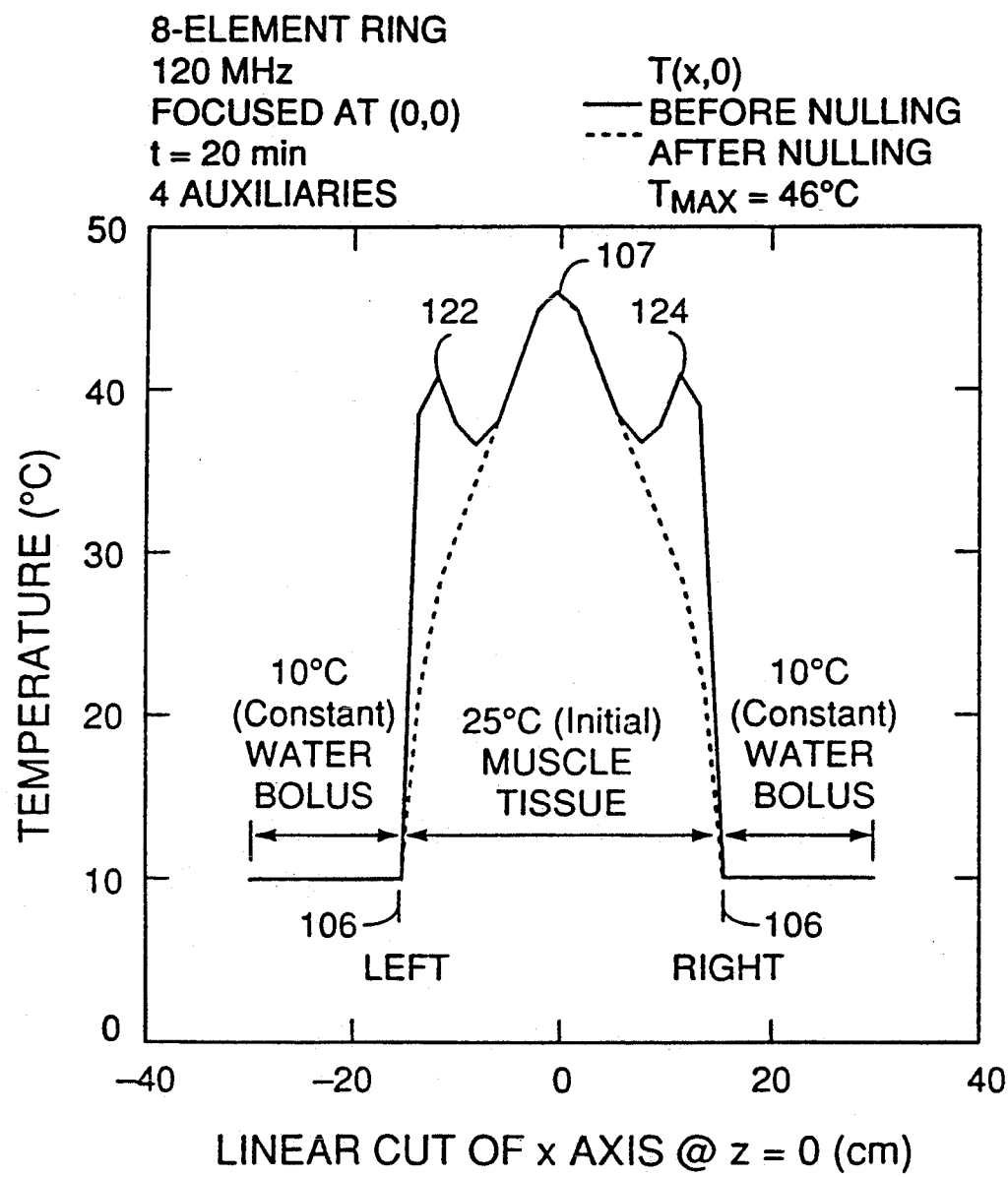
FIGS. 31 and 32 are diagrams of the temperature profile of FIG. 30 taken along the x- and z- axis, respectively.
Figure 32:
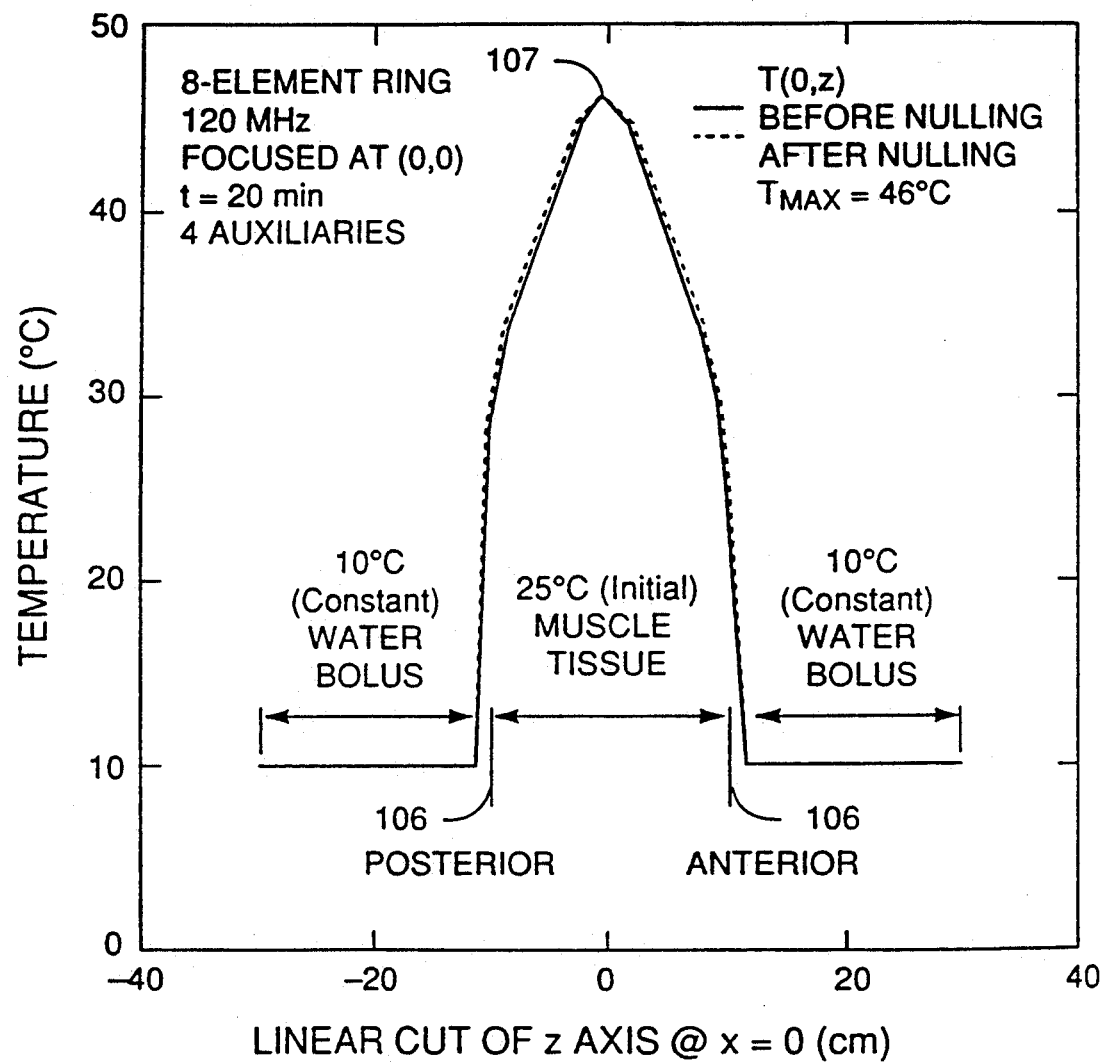

FIG. 30 shows the simulated two-dimensional thermal distribution at time t=20 minutes, with adaptive nulling at four auxiliary probes $112_1$ through $112_4$ in effect. The focal-spot diameter at focus 107 with adaptive nulling is equivalent to the focal-spot diameter before adaptive nulling, shown in FIG. 27. Hot spots on the left and right sides of the target 106 are eliminated. FIG. 31 shows a comparison of the temperature distribution before (solid line) and after (broken line) nulling along the major axis (z=0) of the target ellipse 106. Similarly, FIG. 32 shows the temperature distribution before (solid line) and after (broken line) nulling along the minor axis (x=0) of the target ellipse 106.

Figure 33:
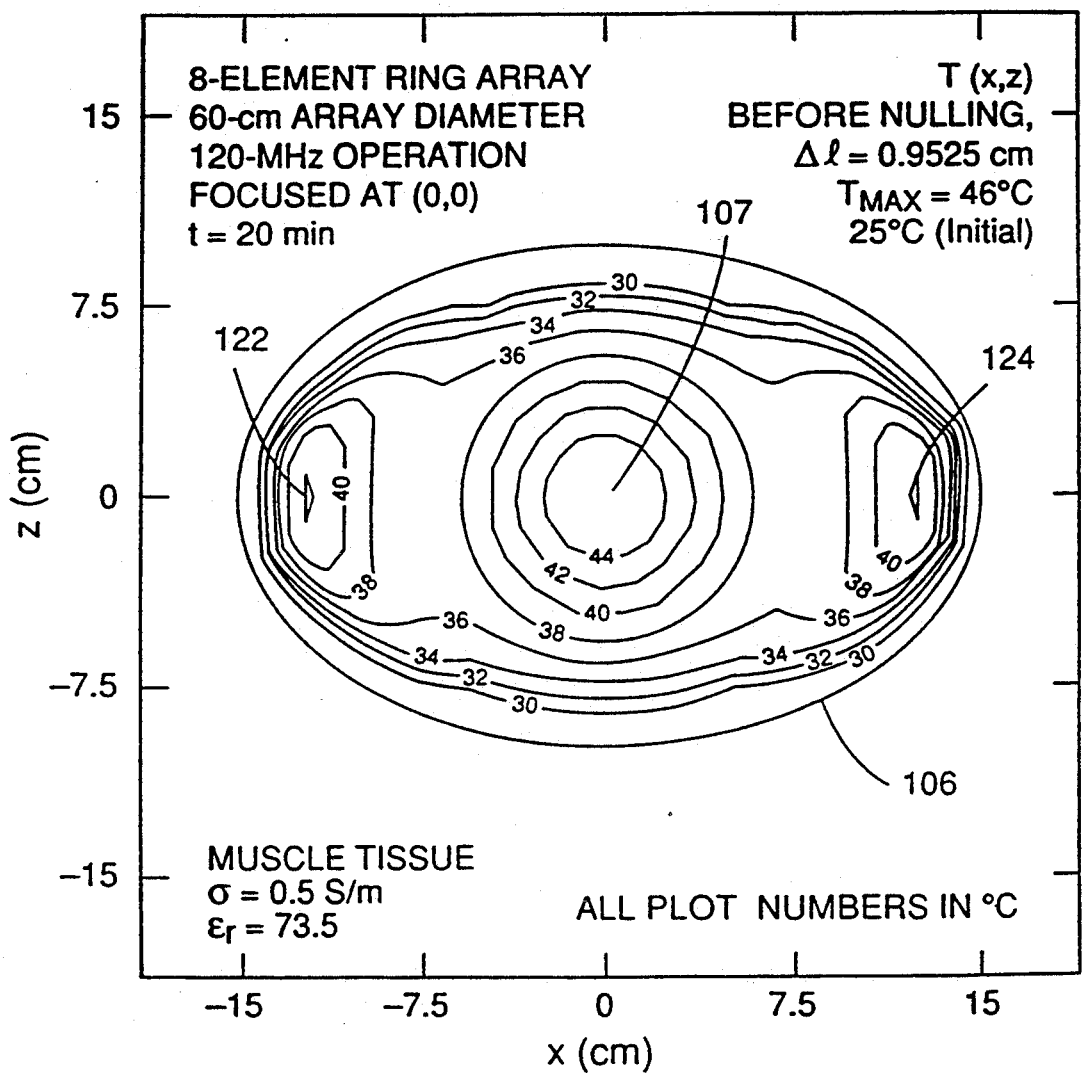
FIG. 33 is a diagram of the simulated target temperature profile for the E-field of FIG. 18 prior to adaptive nulling.
Figure 34:
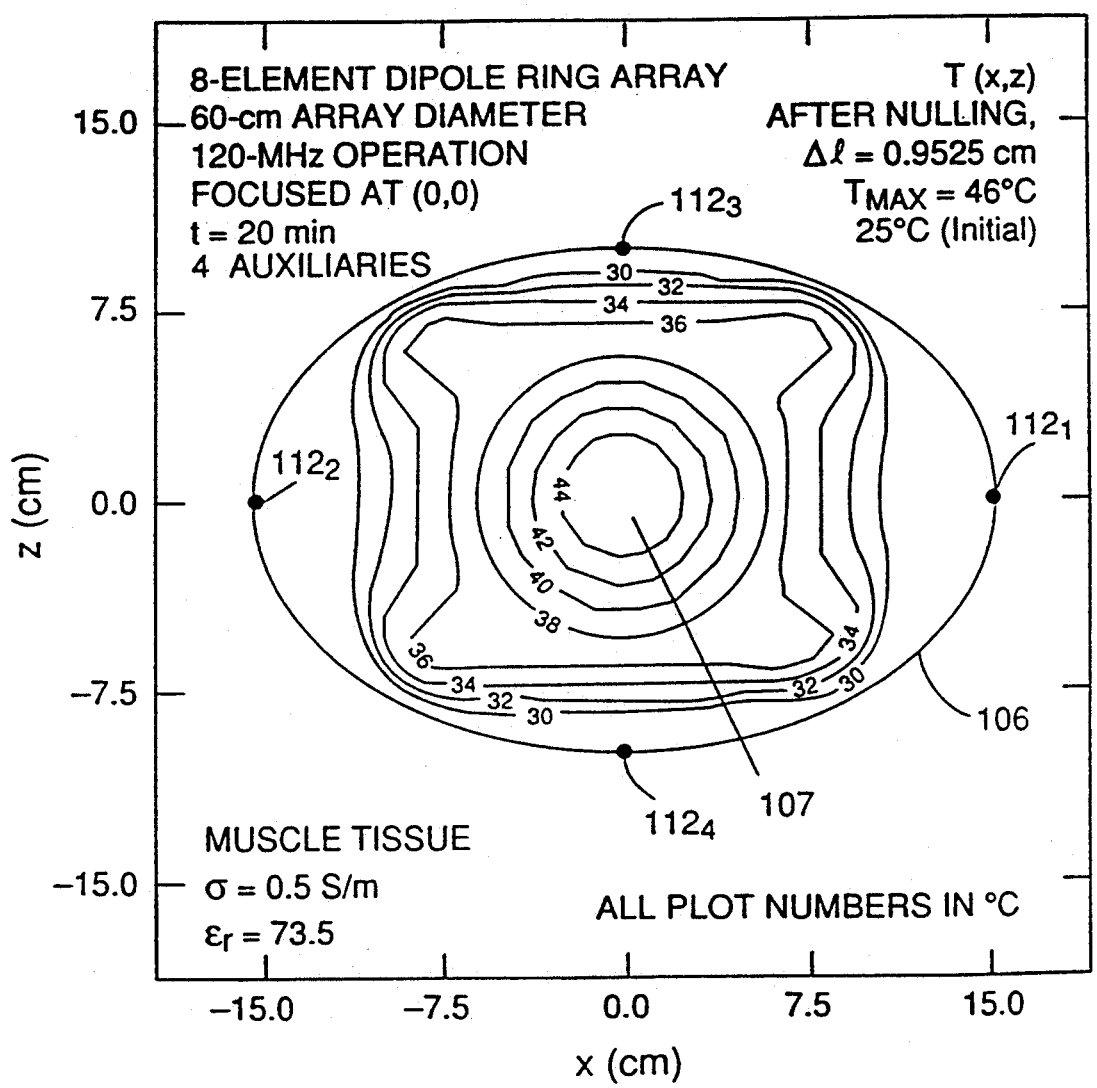
FIG. 34 is a diagram of the simulated target temperature profile for the E-field of FIG. 22 after adaptive nulling.
Figure 35:
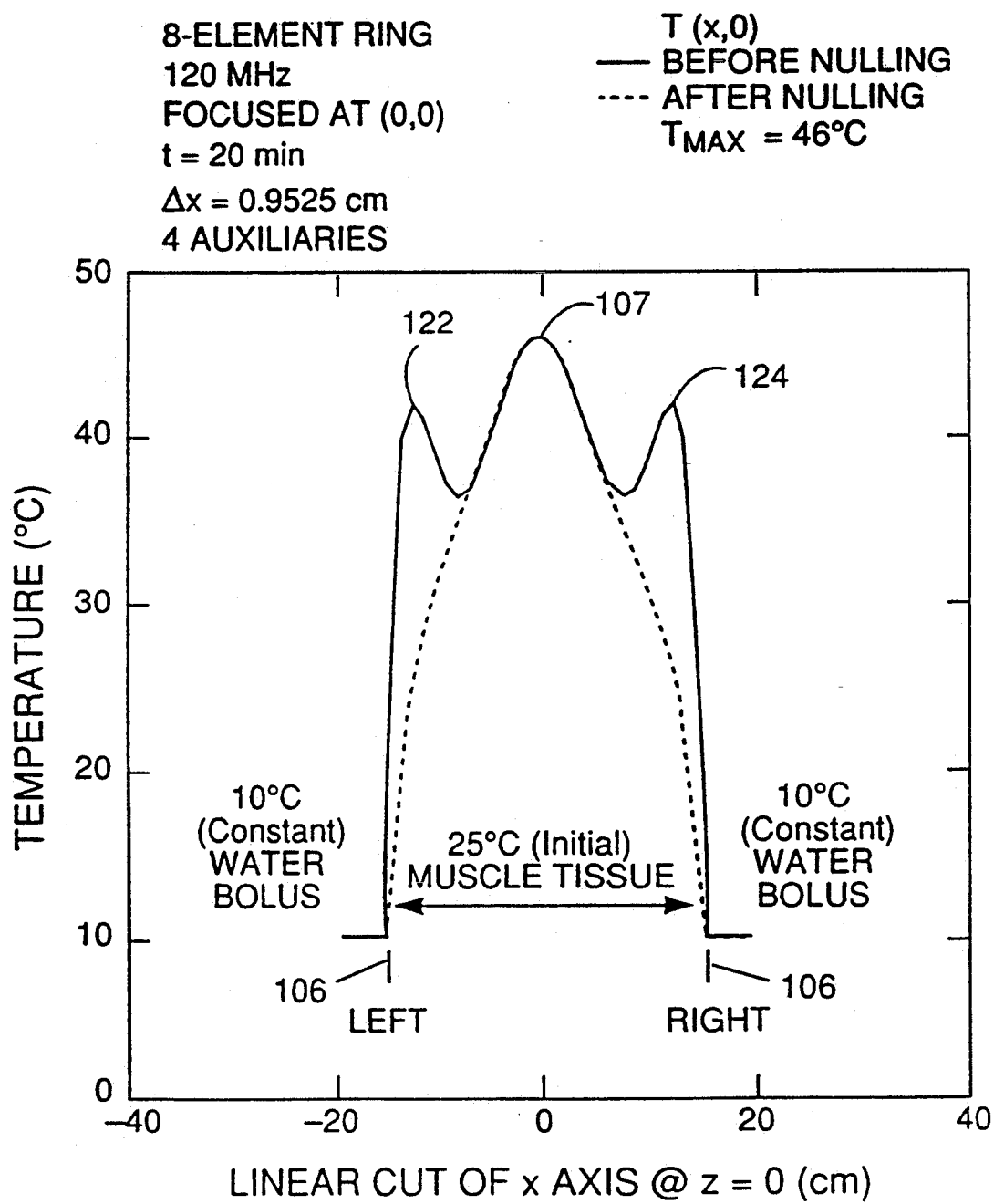
FIGS. 35 and 36 are diagrams of the temperature profile of FIG. 34 taken along the x- and z- axis, respectively.
Figure 36:
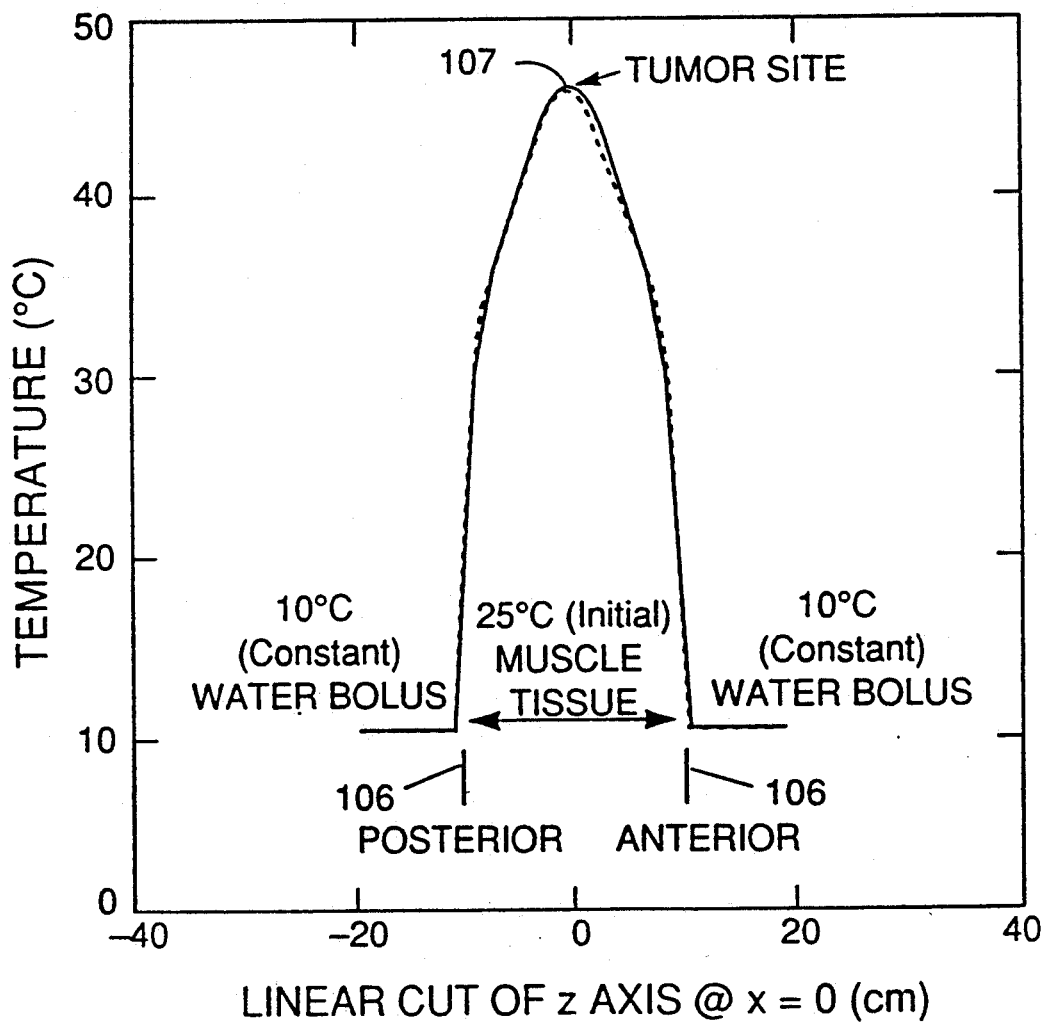

The convergence of the previous thermal simulations was verified by increasing the density of E-field observation probe positions by a factor of two, with a new spacing between points of 0.9525 cm, still with a 41×41 grid. The ring array operates as before at 120 MHz, and there are four auxiliary probes $112_1$ through $112_4$ laid out as shown in FIG. 17. As the auxiliary positions are the same, the adaptive weights and channel correlation matrix eigenvalues in FIGS. 25 and 26, respectively, remain the same. From the parameter values in Table 1, all resistors $R_{ij}$ in the finer-grid muscle-tissue phantom had a value of 193.0° C./W and all resistors $R_{ij}$ in the water bolus had a value of 174.4° C./W. The value of the capacitors $C_i$ in the phantom muscle-tissue is 2.95 J/°C. Again, a constant temperature of 10° C. is enforced at each water-bolus node. The E-field scaling factors to raise the focal-point temperature to 46° C. before and after nulling are 76.5 dB and 78.4 dB, respectively. The finer-grid two-dimensional thermal distributions before and after nulling are shown in FIGS. 33 and 34, respectively. Although the temperature contours are smoother, the general agreement between these patterns and the coarser-grid patterns in FIGS. 27 and 30 are evident. Similarly, one-dimensional thermal pattern cuts with the finer grid are shown in FIGS. 35 (x axis) and 36 (z axis), and good agreement with the coarse-grid patterns of FIGS. 31 and 32, respectively, is observed. In particular, the finer detail in FIG. 35 shows that the hot spots 122 and 124 are at approximately 42° C. compared to 41° C. observed for the coarse grid of FIG. 31. Thus, convergence of the coarse-grid thermal patterns is demonstrated.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. For instance, the adaptive nulling methods described herein are applicable to any hyperthermia system using waves to induce heating, such an ultrasound hyperthermia system, or a combination ultrasound and RF hyperthermia system. Further, although the hyperthermia system is described herein with respect to a particular range of RF frequencies, the invention is applicable to hyperthermia systems operating from low frequencies to microwave frequencies. Although the preferred embodiment of the invention describes using four auxiliary probes, it is understood that a larger or smaller number of auxiliary probes may also be used with differing nulled radiation patterns, e.g., more control over the radiation pattern with more probes and less control with fewer probes. Still further, the invention is applicable to non-medical hyperthermia systems, such as those used for industrial materials heating.

APPENDIX A

```
*** Copyright MIT Lincoln Laboratory 1991
******************makefile for moment method software*******
****file sdipjamhyperMake*****
EXECUTABLE = sdipjamhyper.out
OBJS = sdipjamhyper.o dzabgnloss.o \
        dpack2.o zabgenloss.o pack2.o fwgh.o \
        chebaf.o wwquan.o taylor.o \
        eigenv.o reordr.o ydipsubloss.o \
        plothyper.o contek.o plabel.o \
        conturek.o circsubloss.o
```

```
# use tabs for continues
IL = /usr/lib/f68881/libm.il
FLAGS = -O1 -v -f68881
$(EXECUTABLE): $(OBJS)
        dislink -lF77 $(FLAGS) -o $(EXECUTABLE) $(OBJS) $(IL)

sdipjamhyper.o: /home/ajf/hyperthermia/sdipjamhyper.f
        f77 $(FLAGS) -c /home/ajf/hyperthermia/sdipjamhyper.f $(IL)

plothyper.o: /home/ajf/hyperthermia/plothyper.f
        f77 $(FLAGS) -c /home/ajf/hyperthermia/plothyper.f $(IL)

dzabgnloss.o: /home/ajf/hyperthermia/dzabgnloss.f
        f77 $(FLAGS) -c /home/ajf/hyperthermia/dzabgnloss.f $(IL)

dpack2.o: /home/ajf/monjam/dpack2.f
        f77 $(FLAGS) -c /home/ajf/monjam/dpack2.f $(IL)

contek.o: /home/ajf/monjam/contek.f
        f77 $(FLAGS) -c /home/ajf/monjam/contek.f $(IL)

plabel.o: /home/ajf/monjtr/plabel.f
        f77 $(FLAGS) -c /home/ajf/monjtr/plabel.f $(IL)

conturek.o: /home/ajf/hyperthermia/conturek.f
        f77 $(FLAGS) -c /home/ajf/hyperthermia/conturek.f $(IL)
zabgenloss.o: /home/ajf/hyperthermia/zabgenloss.f
        f77 $(FLAGS) -c /home/ajf/hyperthermia/zabgenloss.f $(IL)

pack2.o: /home/ajf/monjam/pack2.f
        f77 $(FLAGS) -c /home/ajf/monjam/pack2.f $(IL)

fwgh.o: /home/ajf/monjam/fwgh.f
        f77 $(FLAGS) -c /home/ajf/monjam/fwgh.f $(IL)

chebaf.o: /home/ajf/monjam/chebaf.f
        f77 $(FLAGS) -c /home/ajf/monjam/chebaf.f $(IL)

wwquan.o: /home/ajf/monjam/wwquan.f
        f77 $(FLAGS) -c /home/ajf/monjam/wwquan.f $(IL)

taylor.o: /home/ajf/monjam/taylor.f
        f77 $(FLAGS) -c /home/ajf/monjam/taylor.f $(IL)

eigenv.o: /home/ajf/monjam/eigenv.f
        f77 $(FLAGS) -c /home/ajf/monjam/eigenv.f $(IL)
reordr.o: /home/ajf/monjam/reordr.f
        f77 $(FLAGS) -c /home/ajf/monjam/reordr.f $(IL)

ydipsubloss.o: /home/ajf/hyperthermia/ydipsubloss.f
        f77 $(FLAGS) -c /home/ajf/hyperthermia/ydipsubloss.f $(IL)

circsubloss.o: /home/ajf/hyperthermia/circsubloss.f
        f77 $(FLAGS) -c /home/ajf/hyperthermia/circsubloss.f $(IL)

******file sdipjamhyper.f*************
C***PROGRAM SDIPJAMHYPER.F --- ANALYZES FINITE ARRAYS OF DIPOLES
C***IN LOSSY DIELECTRIC OR FREE SPACE.
C***THE DIPOLES ARE ASSUMED TO BE ORIENTED PARALLEL
C***TO THE PLANE OF THE GRID FOR A PLANAR ARRAY, OR THEY CAN BE
C***ARRANGED IN AN ANNULAR (RING) ARRAY CONFIGURATION.
C***RECEIVING CONDITIONS ARE ASSUMED.
C***DOUBLE-PRECISION VERSION
      PARAMETER (NUMCHN=8)
      PARAMETER (NUMAUX=8)
      PARAMETER (NUMJAM=7)
      PARAMETER (NUMELM=8)
      PARAMETER (NUMFRQ=5)
      PARAMETER (NUMNPT=1681)
      COMPLEX PS(1825),CZ(900),VA(NUMELM),Z(NUMELM,NUMELM)
      COMPLEX VTA(NUMELM),VREFA,VRECVA(NUMELM)
      COMPLEX VCW(NUMELM),VRECVX(NUMELM),CJ,CSUMA,VXA
```

CC***THE ABOVE MATRICES ARE DIMENSIONED BY THE NUMBER OF ELEMENTS
      COMPLEX *16 COVNF(NUMCHN,NUMCHN),COVNFI(NUMCHN,NUMCHN)
      COMPLEX *16 COVAAJ(NUMCHN,NUMCHN),CINVCN(NUMCHN,NUMCHN)
      COMPLEX *16 VCHA(NUMCHN,NUMFRQ)
      COMPLEX *16 VMAJMA(NUMJAM,NUMFRQ)
      COMPLEX *16 VAUXJA(NUMAUX,NUMJAM,NUMFRQ)
      COMPLEX *8 VAXCWA(NUMAUX,NUMNPT)
C***NOTE DIMENS.  VCHA(NCHAN,NFREQ),VMAJMA(NJAM,NFREQ)
C                 VAUXJA(NAUX,NJAM,NFREQ),VAXCWA(NAUX,NPTS)
      COMPLEX *8 VXMANA(NUMNPT),ETASP,GAMSP
      COMPLEX *16 EIGVAN(NUMCHN),EIGVEN(NUMCHN,NUMCHN)
      COMPLEX *16 WANA(NUMCHN,1)
      COMPLEX *16 WTCTR(1,NUMCHN),WQSLC(NUMCHN,1)
      COMPLEX *16 WQNA(NUMELM,1),CMPROD(1,NUMCHN),WAN(NUMCHN,1)
      COMPLEX *16 WANDMA(NUMELM,1)
      COMPLEX *16 CWTA(NUMELM,1),ETADP,GAMDP
      DIMENSION ACALPH(NUMELM),RWTA(NUMELM),RWTB(NUMELM)
      DIMENSION VXADB(NUMNPT),VXAPH(NUMNPT)
      DIMENSION XC(NUMNPT),YC(NUMNPT),ZC(NUMNPT)
      DIMENSION THSD(1),PHSD(1),THCT(1),PHCT(1)
      DIMENSION XJAMIN(NUMJAM),YJAMIN(NUMJAM),ZJAMIN(NUMJAM)
      DIMENSION XJAM(NUMJAM),YJAM(NUMJAM),ZJAM(NUMJAM)
      DIMENSION PWRJDB(NUMJAM)
      DIMENSION PCHADB(NUMNPT)
      REAL *8 CNDB,PHASEN,DPDCR,WKE(144),EVLDBN
      REAL *8 PREALN,PIMAGN
      REAL *8 QINRDB,AINRDB,CANCDB,EXCPCB
      REAL *8 QINRAA,AINRAA
      REAL *8 CNCLNA,ELSGDB,ELSGDG,AWSGDB,AWSGDG
      REAL *8 SUMC,SUMAA,AVECAN,AVCAA,SAVE,SAVESR
      REAL *4 RX(100),RY(100),RZ(100),FM(41,41),DMF(41,41)
      REAL *4 AUXADB(NUMAUX),VATENA(NUMAUX)
      INTEGER IAUXA(NUMAUX),LTMP(NUMCHN),MTMP(NUMCHN)
      CHARACTER DATNAM*35, OUTNAM*35
      COMMON/A/DX,DY,NCOLX,NROWY,NEL,HZ,HL,ARAD,ZLOAD,ZCHAR
      COMMON /B/ NGEN,IGEN,THETAS,PHIS,IMUT,IBLTSL,IPATRN
      COMMON /D/ FGHZ,RLAMDA,IWL,IS,NSCANS
      COMMON /DEG/ THDR,THDMIN
      COMMON /PLT/ INEAR,IPLOTM
      COMMON/XLYL/XL,YL
      COMMON/NEAR/IANTX,IANTY,NPOWER,IPCONN,IPCONF,IPCUTF
      COMMON/NEAR2/IPCFX,IPCFY,IPCFZ
      COMMON /P/XN,YN,ZN,RLSX,RLSY,RLSZ,NCOLXN,NROWYN,NCOLZN
      COMMON /P2/EDGET,ICOMB,PUNFLX,PUNFLY
      COMMON /CHEBY/ ICHEB,SLLDB
      COMMON /GROUND/ IGRNDP
      COMMON /NORM/ IENORM,BIGNDB
      COMMON /NORMAL/ INRNOR
      COMMON/PCENTR/PCDXIN
      COMMON /WRITE/ IWR
      COMMON /SPLOSS/ ETASP,GAMSP
      COMMON /DPLOSS/ ETADP,GAMDP
      COMMON /F/ FHZ,ER3,SIG3,TD3
      COMMON /CIRCLE/ ICIRC,RADIUS,HLS
      NAMELIST/DIPOLE/NCOLX,NROWY,HZIN,HLIN,ARADIN,ZLOAD,NGEN,IGEN,
     1DXIN,DYIN,IMUT,NSCANS,THSD,PHSD,THSINC,IBLTSL,IPATRN,ER3,SIG3,TD3,
     2NPHCT,PHCT,NTHPT,ZCHAR,IWL,FCHZ,BWFHZ,NFREQ,THDR,THDMIN,ICIRC,
     3XNIN,YNIN,ZNIN,NCOLXN,NROWYN,NCOLZN,INEAR,IPRCOM,IANGLP,CRADIN,
     4IANTX,IANTY,NPOWER,NFCOLX,NFROWY,IPCONN,IPCONF,IPCUTF,IPOL,HLSIN,
     5IPCFX,IPCFY,IPCFZ,ITEK,IGRNDP,IGAIN,ICHEB,IWR,IENORM,BIGNDB,
     6NXDUM,NYDUM,NPDX,EDGTDB,RLSXIN,RLSYIN,RLSZIN,ISLC,INUNIF,
     7XFOCIN,ZFOCIN,XJAMIN,YJAMIN,ZJAMIN,IATTEN,AUXADB,INRNOR,
     8NJAMS,PWRCDB,PWRJDB,NAUX,IAUXA,IAUXB,ITLTPR,ITLTDP,
     9IQUAN,IRNERR,ELERDB,ELERDG,AWERDB,AWERDG,NBMOD,NBADWT,NRAN,SLLDB
C**NOTE; IF IWL=0 (INCHES), IWL=2 (METERS)
      WRITE(6,2959)
 2959 FORMAT(1X,'ENTER INPUT DATA FILE NAME (typ. sdipjamhyper.data)')
      READ(5,*) DATNAM
      OPEN(4,FILE=DATNAM,FORM='FORMATTED')
      WRITE(6,3959)
 3959 FORMAT(1X,'ENTER OUTPUT DATA FILE NAME (typ sdipjamhyper.output)')

```
      READ(5,*) OUTNAM
      OPEN(8,FILE=OUTNAM,FORM='FORMATTED')
      CALL GETCP2(CPU1)
      PI=3.141592654
      DCR=PI/180.
      DPDCR=DCR
      CJ=(0.,1.)
      CINMTR=0.0254
      IGRNDP=1
      IGAIN=0
      ZLOAD=0.0
      ICHEB=0
      IWR=0
      IENORM=1
      EXCPCB=-1.0D0
      IQUAN=0
      NRAN=1
      TILTPR=0.0
      TILTDP=0.0
      IATTEN=0
      IPOL=1
      ER3=1.0
      SIG3=0.0
      TD3=-1.0
      ICIRC=0
      CRADIN=0.0
      HLSIN=0.0
      ISLC=1
      INUNIF=0
      INRNOR=0
      READ(4,DIPOLE)
      IF(NFREQ.EQ.1) BWFHZ=0.0
      IF(ISLC.EQ.0) WRITE(6,81100)
81100 FORMAT(1X,'FULLY ADAPTIVE ARRAY')
      IF(ISLC.EQ.0.AND.ICHEB.EQ.0) INUNIF=1
      IF(ICIRC.EQ.1) WRITE(6,7000)
7000  FORMAT(1X,'RING ARRAY GEOMETRY')
      FHZ=FCHZ
      IXZ=0
      IXY=0
      IF(NROWYN.EQ.1) IXZ=1
      IF(NCOLZN.EQ.1) IXY=1
      IF(IPOL.EQ.2) IPRCOM=0
      IF(IPRCOM.EQ.0) WRITE(6,7898)
7898  FORMAT(1X,'NO PROBE COMPENSATION')
      WRITE(6,9276)IGRNDP
9276  FORMAT(1X'GROUND PLANE PARAMETER, IGRNDP=',I4)
CC    DO 1615 IX=1,NAUX
CC    IF(IATTEN.EQ.0) AUXADB(IX)=0.0
CC    WRITE(6,2318)IX,AUXADB(IX)
C2318  FORMAT(1X,'IX,AUXADB(IX)=',I4,2X,F12.2)
CC    VATENA(IX)=10.**(AUXADB(IX)/20.)
C1615 CONTINUE
      IF(NJAMS.GT.1) WRITE(8,2009)XJAMIN(1),YJAMIN(1),ZJAMIN(1)
2009  FORMAT(1X,'XJAMIN(1),YJAMIN(1),ZJAMIN(1)=',3F12.3)
      WRITE(6,6987) BWFHZ,NFREQ
6987  FORMAT(1X,'BWFHZ,NFREQ=',E12.5,2X,I5)
      IF(ITEK.EQ.0)CALL COMPRS
      IF(ITEK.EQ.1)CALL TEKALL(4014,480,0,1,0)
CC    IF(INEAR.EQ.0) CALL PRNTDA
      IF(IMUT.EQ.0) ZLOAD=1.0
      IF(ITLTPR.EQ.1) TILTPR=45.
      IF(ITLTDP.EQ.1) TILTDP=45.
      CTPR=COS(TILTPR*DCR)
      STPR=SIN(TILTPR*DCR)
      CTDP=COS(TILTDP*DCR)
      STDP=SIN(TILTDP*DCR)
      FGHZ=FCHZ/1.0E9
      NEL=NCOLX*NROWY
      RNEL=NEL
      XLIN=DXIN*(NCOLX-1)
      YLIN=DYIN*(NROWY-1)
      NACOLX=NCOLX-NPDX-2*NXDUM
      NAROWY=NROWY-2*NYDUM
```

```
              NAEL=NACOLX*NAROWY
              PCDXIN=NPDX*DXIN
              NAUXP1=NAUX+1
              NAUXP2=NAUX+2
              IF(ISLC.EQ.1) NMAX=NAUXP1
              IF(ISLC.EQ.0) NMAX=NEL
              NMAXP1=NMAX+1
              ELSGDB=ELERDB*SQRT(3.)
              ELSGDG=ELERDG*SQRT(3.)
              AWSGDB=AWERDB*SQRT(3.)
              AWSGDG=AWERDG*SQRT(3.)
              INITRN=1
              IF(ISLC.EQ.0) THEN
                 NAUX=NEL
                 NAUXP1=NAUX+1
                 NAUXP2=NAUX+2
                 DO 79130 I=1,NEL
                 IAUXA(I)=I
                 WRITE(6,76767)I,IAUXA(I)
76767            FORMAT(1X,'I,IAUXA(I)=',2I5)
79130         CONTINUE
              ENDIF
              DO 1615 IX=1,NAUX
              IF(IATTEN.EQ.0) AUXADB(IX)=0.0
              WRITE(6,2318)IX,AUXADB(IX)
2318          FORMAT(1X,'IX,AUXADB(IX)=',I4,2X,F12.2)
              VATENA(IX)=10.**(AUXADB(IX)/20.)
1615       CONTINUE
30         CONTINUE
              NR=1
              IF(NGEN.EQ.1) NSCANS=0
              ICC=NEL
              ICC1=ICC
              IF(IBLTSL.EQ.1) ICC1=NROWY
CC            IF(IWL.EQ.1)GO TO 50
              WRITE(8,40)FGHZ
40            FORMAT(/,1X,'FGHZ=',F15.7)
C****************************************************************
C*****COMPUTE FREE SPACE LAMBDA*******
C*****ALL UNITS HAVE TO BE IN METERS
              RLAMDA=2.997925E10/FCHZ/2.54
C***PARAMETER CONVERSIONS TO PROPER UNITS
55         CONTINUE
              IF(IWL.EQ.2) GO TO 50
              DX=DXIN*CINMTR
              DY=DYIN*CINMTR
              HL=HLIN*CINMTR
              HLS=HLSIN*CINMTR
              ARAD=ARADIN*CINMTR
              HZ=HZIN*CINMTR
              RLSX=RLSXIN*CINMTR
              RLSY=RLSYIN*CINMTR
              RLSZ=RLSZIN*CINMTR
              XN=XNIN*CINMTR
              YN=YNIN*CINMTR
              ZN=ZNIN*CINMTR
              XFOC=XFOCIN*CINMTR
              ZFOC=ZFOCIN*CINMTR
              XL=XLIN*CINMTR
              YL=YLIN*CINMTR
              PCDX=PCDXIN*CINMTR
              RADIUS=CRADIN*CINMTR
50         CONTINUE
              WRITE(8,60)DX,DY,HL,ARAD
60            FORMAT(1X,'DX,DY,HL,ARAD=',2X,4F14.5)
C
C***COMPUTE CALIBRATION CONSTANTS (PHASE ONLY) TO
C***MAXIMIZE GAIN (FOCUS ANTENNA) TO NEAR FIELD RANGE
C
C***PHASE CENTER 'A' VOLTAGE EXCITATION
              X0A=-XL/2.+NXDUM*DX+(NACOLX-1)/2.*DX
              YP=0.0
              IF(ICIRC.EQ.0) WRITE(6,24690)
```

```
24690   FORMAT(1X,'CALLING NFDPX2')
        IF(ICIRC.EQ.0)
       2CALL NFDPX2(CTPR,STPR,CTDP,STDP,XFOC,YP,ZFOC,X0A,0,VA,VREFA)
        IF(ICIRC.EQ.1)
       2CALL NFDPC2(XFOC,YP,ZFOC,X0A,0,VA,VREFA)
C***SAVE INCIDENT VOLTAGES
        DO 65 IV=1,NEL
        VTA(IV)=VA(IV)
        WRITE(6,3757)IV,VTA(IV)
        WRITE(8,3757)IV,VTA(IV)
3757    FORMAT(1X,'IV,VTA=',I4,2X,2E12.4)
65      CONTINUE
        WRITE(6,9876)VTA(2)
9876    FORMAT(1X,'VTA(2)=',2E12.4)
        NB=NCOLX
        IDMB=NROWY
        IDM=NEL
        ICC=NEL
        IBLT=IBLTSL
        IDM1=IDMB
        IF(IBLT.EQ.0) IDM1=NEL
        I2=1
8889    CONTINUE
        CALL ZMATRX(CTDP,STDP,IBLTSL,ICC1,ICC,CZ,Z)
C***SOLVE SYSTEM OF EQUATIONS FOR THE UNKNOWN CURRENTS
        IF(IBLT.EQ.1) GO TO 240
        ISYM=0
        I12=1
        WRITE(6,9876)VTA(2)
        WRITE(6,6110)
6110    FORMAT(1X,'CALL CROUT')
        CALL CROUT(Z,VA,ICC1,ICC,ISYM,IWR,I12,NEL)
        I12=2
        WRITE(6,9876)VTA(2)
        GO TO 255
240     IENTRY=4
        CALL BLTSOL(CZ,VA,PS,NCOLX,IDMB,IENTRY)
        IENTRY=3
255     WRITE(8,270)
270     FORMAT(1X,'CURRENTS')
        IF(NEL.LT.40) CALL CNORM(VA,NEL)
        WRITE(6,280)
280     FORMAT(1X,'AFTER CURRENTS SOLUTION')
C***VA ARE CURRENTS (AMPERES) NOW
C*
C***COMPUTE RECEIVED VOLTAGES
        DO 285 IC=1,NEL
        WRITE(6,7531)ZLOAD
7531    FORMAT(1X,'ZLOAD=',F12.5)
        WRITE(6,1134)IC,VTA(IC)
        VRECVA(IC)=VA(IC)*ZLOAD
        WRITE(6,1174)IC,VRECVA(IC)
1134    FORMAT(1X,'IC,VTA=',I4,2X,2E12.4)
1174    FORMAT(1X,'IC,VRECVA=',I4,2X,2E12.4)
        WRITE(6,1135)IC,VA(IC)
1135    FORMAT(1X,'IC,VA=',I4,2X,2E12.4)
        VRADB=20.*ALOG10(CABS(VRECVA(IC)))
        VRAPH=ATAN2(AIMAG(VRECVA(IC)),REAL(VRECVA(IC)))/DCR
C***COMPUTE CALIBRATION CONSTANTS (PHASE ONLY)
        ACALPH(IC)=-VRAPH
285     CONTINUE
        DO 7777 IC=1,NEL
        WRITE(6,6667)IC,ACALPH(IC)
CC      WRITE(8,6667)IC,ACALPH(IC)
6667    FORMAT(1X,'IC,ACALPH=',I4,2X,F10.2,' DEGS')
7777    CONTINUE
C***COMPUTE NEAR FIELD PATTERN OF FOCUSED ARRAY
C
C***COMPUTE BEAMFORMER WEIGHTS (I.E. TAPER)
        IF(INUNIF.EQ.0)
       2CALL VRCVWT(NACOLX,NAROWY,NXDUM,NYDUM,EDGTDB,RWTA,RWTB)
        DO 1199 IC=1,NEL
        IF(INUNIF.EQ.1.AND.ISLC.EQ.0) RWTA(IC)=1./SQRT(RNEL)
```

```
              WRITE(6,5111)IC,RWTA(IC)
         WRITE(8,5111)IC,RWTA(IC)
5111     FORMAT(1X,'IC,RWTA=',I4,2X,E12.5)
1199     CONTINUE
         DO 5333 KC=1,NEL
         CWTA(KC,1)=RWTA(KC)*CEXP(CJ*ACALPH(KC)*DCR)
5333     CONTINUE
         IF(IQUAN.EQ.1)
        2CALL ADQUAN(NEL,CWTA,NBMOD,IRNERR,INITRN,ELSGDB,ELSGDG)
         BIGWDB=-299.0
         DO 91020 I=1,NEL
         WRITE(6,61910)I,CWTA(I,1)
         WRITE(8,61910)I,CWTA(I,1)
61910    FORMAT(1X,'I,CWTA(I,1)=',I4,2X,2E12.5)
         CWTADB=20.*DLOG10(CDABS(CWTA(I,1)))
         IF(CWTADB.GT.BIGWDB) BIGWDB=CWTADB
91020    CONTINUE
         DO 91120 I=1,NEL
         CWTADB=20.*DLOG10(CDABS(CWTA(I,1)))-BIGWDB
         CWTADG=DATAN2(DIMAG(CWTA(I,1)),DREAL(CWTA(I,1)))/DCR
         WRITE(6,35990)I,CWTADB,CWTADG
         WRITE(8,35990)I,CWTADB,CWTADG
35990    FORMAT(1X,'I=',I4,2X,'CWTADB,CWTADG=',1X,2F14.5)
91120    CONTINUE
         INITRN=2
C***PERFORM NEAR FIELD SCAN WITH CW RADIATING DIPOLE
         IF(INEAR.EQ.0) GO TO 390
         WRITE(6,350)
         WRITE(6,360)XNIN,YNIN,ZNIN,RLSXIN,RLSYIN,RLSZIN,NCOLXN,NROWYN,
        2NCOLZN
         WRITE(6,320)IWL
320      FORMAT(1X,'IWL=',I4)
         WRITE(6,330)
330      FORMAT(1X,'CHANGE NEAR FIELD SCAN PARAMETERS?, ICHANG=1')
         READ(5,*,END=370)ICHANG
         IF(ICHANG.EQ.0) GO TO 370
340      WRITE(6,350)
350      FORMAT(1X,'XN,YN,ZN,RLSXIN,RLSYIN,RLSZIN,NCOLXN,NROWYN,NCOLZN=')
         READ(5,*)XNIN,YNIN,ZNIN,RLSXIN,RLSYIN,RLSZIN,NCOLXN,NROWYN,NCOLZN
         WRITE(6,360)XNIN,YNIN,ZNIN,RLSXIN,RLSYIN,RLSZIN,NCOLXN,NROWYN,
        2NCOLZN
360      FORMAT(1X,6F10.3,2X,3I5)
         IF(IWL.EQ.2) GO TO 370
         XN=XNIN*CINMTR
         YN=YNIN*CINMTR
         ZN=ZNIN*CINMTR
         RLSX=RLSXIN*CINMTR
         RLSY=RLSYIN*CINMTR
         RLSZ=RLSZIN*CINMTR
370      CONTINUE
C**ALL DIMENSIONS IN METERS
         NELN=NCOLXN*NROWYN
         NPTSN=NELN*NCOLZN
C***SET DEFAULT VALUES FOR DXN,DYN,DZN
         DXN=0.0
         DYN=0.1
         DZN=0.0
         IF(NCOLXN.GT.1)DXN=RLSX/(NCOLXN-1)
         IF(NROWYN.GT.1)DYN=RLSY/(NROWYN-1)
         IF(NCOLZN.GT.1)DZN=RLSZ/(NCOLZN-1)
         IC=0
         BIGNDB=-299.0
         DO 3000 ICOLZN=1,NCOLZN
         ZPOS=ZN+DZN*(ICOLZN-1)
         DO 3000 IROWYN=1,NROWYN
         Y=YN+DYN*(IROWYN-1)
         DO 3000 ICOLXN=1,NCOLXN
         CALL GETCP2(CPU2)
         CPUSUB=CPU2-CPU1
         WRITE(6,7319)CPUSUB
7319     FORMAT(1X,'CPU SUBTOTAL=',F14.2)
         IC=IC+1
         X=XN+DXN*(ICOLXN-1)
```

```
            XC(IC)=X
            YC(IC)=Y
            ZC(IC)=ZPOS
            WRITE(6,6969)IC,XC(IC),YC(IC),ZC(IC)
 6969       FORMAT(1X,'IC,XC,YC,ZC=',I4,2X,3F12.3)
            IF(ICIRC.EQ.0)
           2CALL NFDPX2(CTPR,STPR,CTDP,STDP,X,Y,ZPOS,0.0,0,VCW,VREFCW)
            IF(ICIRC.EQ.1)
           2CALL NFDPC2(X,Y,ZPOS,0.0,0,VCW,VREFCW)
            IF(IMUT.EQ.0) GO TO 4255
C***SOLVE EACH SYSTEM OF EQUATIONS FOR THE UNKNOWN CURRENTS
            IF(IBLT.EQ.1) GO TO 4040
            I12=2
            WRITE(6,6110)
            CALL CROUT(Z,VCW,ICC1,ICC,ISYM,IWR,I12,NEL)
            GO TO 4255
 4040       IENTRY=3
            CALL BLTSOL(CZ,VCW,PS,NCOLX,IDMB,IENTRY)
 4255       CONTINUE
C***COMPUTE RECEIVED VOLTAGES FOR PRESENT SCAN
            DO 3285 IIIC=1,NEL
            VRECVX(IIIC)=VCW(IIIC)*ZLOAD
 3285       CONTINUE
C***STORE AUX. CHANNEL VOLTAGES
            DO 1681 IAX=1,NAUX
C**MODIFICATION TO INCLUDE AUX. ATTEN.
            VAXCWA(IAX,IC)=VRECVX(IAUXA(IAX))*VATENA(IAX)
CC          WRITE(6,3231)IAX,IC,XC(IC),VAXCWA(IAX,IC)
 3231       FORMAT(1X,'IAX,IC,XC,VAXCWA(IAX,IC)=',2I4,2X,F12.3,2X,2E12.5)
 1681       CONTINUE
C***PERFORM BEAM FORMATION
            CSUMA=(0.,0.)
            DO 5444 KC=1,NEL
            CSUMA=CSUMA+VRECVX(KC)*CWTA(KC,1)
 5444       CONTINUE
            VXA=CSUMA
            IF(CABS(VXA).EQ.0.)VXA=(1.E-10,0.)
            VXADB(IC)=20.*ALOG10(CABS(VXA))
            IF(VXADB(IC).GT.BIGNDB) BIGNDB=VXADB(IC)
            VXAPH(IC)=ATAN2(AIMAG(VXA),REAL(VXA))/DCR
            VXMANA(IC)=10.**(VXADB(IC)/20.)*CEXP(CJ*VXAPH(IC)*DCR)
CC          WRITE(6,4457)IC,VXMANA(IC)
 4457       FORMAT(1X,'IC,VXMANA=',I4,2X,2E12.5)
            WRITE(6,6429)IC,XC(IC),VXADB(IC)
 6429       FORMAT(1X,'IC,X,VXADB=',I4,2X,F10.2,2X,F12.2)
 3000       CONTINUE
            IF(IENORM.EQ.0) GO TO 2500
            WRITE(6,3765)BIGNDB
 3765       FORMAT(1X,'BIGNDB=',F12.2)
            DO 3020 IC=1,NPTSN
CC          WRITE(6,3343)IC,VXADB(IC)
            VXADB(IC)=VXADB(IC)-BIGNDB
CC          WRITE(6,3343)IC,VXADB(IC)
 3020       CONTINUE
 2500       WRITE(6,3030)
 3030       FORMAT(1X,'WANT TO PLOT NEAR FIELD CUTS, IPLOTN=1')
            READ(5,*)IPLOTN
C***NEXT LINE ADDED TO AVOID RUN TIME ERROR
            IF(IPCONN.EQ.1) IPLOTN=0
            IF(IPCONN.EQ.0) THEN
               WRITE(30,18889)
               WRITE(30,18888)XN,NCOLXN,DXN,ZN,NCOLZN,DZN
               WRITE(30,4547)
 4547       FORMAT(1X,'IZ,IX,VXADB(IC)')
            ENDIF
            IPP=0
            DO 7788 IZ=1,NCOLZN
            DO 7788 IY=1,NROWYN
            DO 7788 IX=1,NCOLXN
            IPP=IPP+1
CC          DO 7788 IPP=1,NPTSN
CC          WRITE(6,3343)IPP,VXADB(IPP)
 3343       FORMAT(1X,'IPP,VXADB=',I4,2X,F12.2)
            IF(IPCONN.EQ.0) WRITE(30,*) IZ,IX,VXADB(IPP)
```

```
      7788 CONTINUE
      3040 IF((NCOLXN.GT.1.OR.NROWYN.GT.1).AND.IPLOTN.EQ.1)
          1CALL PLOTTR(NCOLXN,NROWYN,NCOLZN,XC,YC,ZC,NPTSN,VXADB,VXAPH,
          2VXADB,VXAPH)
           IF(NELN.EQ.1.AND.IPLOTN.EQ.1)
          1CALL PLOTAX(NPTSN,ZC,VXADB,VXAPH,VXADB,VXAPH)
           IF(IPCONN.EQ.0) GO TO 3939
C***THIS SECTION FOR CONTOUR PLOTS
           NCLXN2=NCOLXN+2
           NRWYN2=NROWYN+2
           NCLZN2=NCOLZN+2
           DO 3777 IX=1,NCOLXN
           RX(IX)=(XN+DXN*(IX-1))/CINMTR
      3777 CONTINUE
           DO 3008 IY=1,NROWYN
           RY(IY)=(YN+DYN*(IY-1))/CINMTR
      3008 CONTINUE
           DO 3009 IZ=1,NCOLZN
           RZ(IZ)=(ZN+DZN*(IZ-1))/CINMTR
      3009 CONTINUE
           IC=0
           IF(IXZ.EQ.1) WRITE(30,18889)
     18889 FORMAT(1X,'XN,NCOLXN,DXN,ZN,NCOLZN,DZN=')
           IF(IXZ.EQ.1) WRITE(30,18888)XN,NCOLXN,DXN,ZN,NCOLZN,DZN
     18888 FORMAT(1X,E14.5,I5,2X,E14.5,2X,E14.5,I5,2X,E14.5)
           IF(IXZ.EQ.1) WRITE(30,4546)
      4546 FORMAT(1X,'IZ,IX,FM(IZ,IX)')
           DO 3022 IZ=1,NCOLZN
           DO 3022 IY=1,NROWYN
           DO 3022 IX=1,NCOLXN
           IC=IC+1
        IF(IXY.EQ.1) FM(IY,IX)=VXADB(IC)
        IF(IXZ.EQ.1) FM(IZ,IX)=VXADB(IC)
        IF(IXZ.EQ.1.AND.IPCONN.EQ.1) WRITE(30,*) IZ,IX,FM(IZ,IX)
      3022 CONTINUE
           IF(IXY.EQ.1)
          2CALL PLCONT(NCOLXN,NROWYN,NCLXN2,NRWYN2,RX,RY,FM,DMF,-50.,
           310.,5,1)
           IF(IXZ.EQ.1)
          2CALL PLCONT(NCOLXN,NCOLZN,NCLXN2,NCLZN2,RX,RZ,FM,DMF,-50.,
           310.,5,1)
      3939 CONTINUE
CC         WRITE(25,*)NCOLXN
           DO 1767 IDDD=1,NCOLXN
CC         WRITE(25,*)VXADB(IDDD)
      1767 CONTINUE
           WRITE(6,3050)
      3050 FORMAT(1X,'PLOT NEAR FIELD AGAIN?, IPLA=1')
           READ(5,*)IPLA
           IF(IPLA.EQ.1) GO TO 3040
       390 CONTINUE
           ISTOP=0
           IF(ISTOP.EQ.1) GO TO 9999
C***CALL PRNTDA (PRINT PARAMETERS)
C370       CALL PRNTDA
           IF(IPATRN.EQ.0) GO TO 440
       410 WRITE(6,420)
       420 FORMAT(1X,'ISYLMBL FOR PLOTTING, LT. 0 THEN NOT USED')
           READ(5,*)ISYMBL
           WRITE(6,430)
       430 FORMAT(1X,'WANT TO PLOT PATTERNS AGAIN?, IPFNA=1')
           READ(5,*)IPFNA
           IF(IPFNA.EQ.1) GO TO 410
       440 CONTINUE
C***THIS SECTION FOR COVARIANCE MATRIX COMPUTATION
           IF(NJAMS.EQ.0) GO TO 9999
           DO 7999 ICH=1,NMAX
           DO 7999 JCH=1,NMAX
           COVNF(ICH,JCH)=DCMPLX(0.0D0,0.0D0)
      7999 CONTINUE
      8888 IF(NJAMS.EQ.0) GO TO 4444
C***THIS SECTION FOR JAMMER COVARIANCE MATRIX
           FMINHZ=FCHZ-BWFHZ/2.
```

```
      DELFHZ=0.0
      IF(NFREQ.GT.1) DELFHZ=BWFHZ/(NFREQ-1)
      DO 600 IFR=1,NFREQ
      FHZ=FMINHZ+DELFHZ*(IFR-1)
      FGHZ=FHZ/1.0E9
C***COMPUTE FREE SPACE WAVELENGTH AT EACH FREQUENCY
      RLAMDA=2.997925E10/FHZ/2.54
C***NOTE: GAMMA= ALPHA +J BETA
C***      AND RLAMDA=2 PI/ BETA   (REF. HAYT PG. 334)
C***THUS NEED TO COMPUTE GAMMA, AND ETA FOR EACH FREQ.
      IF(IWL.EQ.2) GO TO 8789
      DX=DXIN*CINMTR
      DY=DYIN*CINMTR
      HL=HLIN*CINMTR
      ARAD=ARADIN*CINMTR
      HZ=HZIN*CINMTR
 8789 CONTINUE
      CALL ZMATRX(CTDP,STDP,IBLTSL,ICC1,ICC,CZ,Z)
C***COMPUTE ELEMENT INDUCED VOLTAGES DUE TO JAMMER SOURCES
      CALL VJAMMR(NJAMS,NEL,PWRJDB,ICC1,ICC,PS,CZ,Z,CWTA
     1,NB,IDMB,NAUX,IAUXA,ZLOAD,XJAMIN,YJAMIN,ZJAMIN,
     2IFR,NFREQ,CTPR,STPR,CTDP,STDP,VMAJMA,VAUXJA)
      WRITE(6,1234)IFR,VMAJMA(1,IFR),VAUXJA(1,1,IFR)
      WRITE(8,1234)IFR,VMAJMA(1,IFR),VAUXJA(1,1,IFR)
 1234 FORMAT(1X,'IFR,VMAJMA,VAUXA=',I4,2X,4E11.4)
  600 CONTINUE
C***FORM RECEIVED VOLTAGE MATRIX
C***VRECVM(MAIN A, AUX A1, AUX A2,... AUX AN :)
      DO 9001 IJAM=1,NJAMS
      DO 9002 IFR=1,NFREQ
      IF(ISLC.EQ.1) VCHA(1,IFR)=VMAJMA(IJAM,IFR)
CC    WRITE(6,6789)IJAM,IFR,VMAJMA(IJAM,IFR)
 6789 FORMAT(1X,'IJAM,IFR,VMAJMA(IJAM,IFR)=',2I4,2X,2E12.5)
      DO 9003 IA=1,NAUX
      IAP1=IA+1
      IF(ISLC.EQ.1) VCHA(IAP1,IFR)=VAUXJA(IA,IJAM,IFR)*VATENA(IA)
      IF(ISLC.EQ.0) VCHA(IA,IFR)=VAUXJA(IA,IJAM,IFR)*VATENA(IA)
      WRITE(6,8876)IJAM,IFR,IA,VAUXJA(IA,IJAM,IFR)
      WRITE(8,8876)IJAM,IFR,IA,VAUXJA(IA,IJAM,IFR)
 8876 FORMAT(1X,'IJAM,IFR,IA,VAUXJA=',3I4,2X,2E12.4)
 9003 CONTINUE
 9002 CONTINUE
      DO 5555 KKK=1,4
      DO 5555 LLL=1,NFREQ
CCC   WRITE(6,6655)KKK,LLL,VCHA(KKK,LLL)
 5555 CONTINUE
      WRITE(6,5533)
 5533 FORMAT(1X,'NOW COMPUTE JAMMER COVARIANCE MATRIX')
C***COMPUTE COVARIANCE MATRIX FOR JTH JAMMER SOURCE
      IF(NFREQ.GT.1) CALL COVSWC(VCHA,VCHA,NMAX,NFREQ,BWFHZ,COVAAJ)
      DO 9005 ICH=1,NMAX
      DO 9005 JCH=1,NMAX
      COVNF(ICH,JCH)=COVNF(ICH,JCH)+COVAAJ(ICH,JCH)
CC    WRITE(6,2299)ICH,JCH,COVNF(ICH,JCH)
 9005 CONTINUE
 9001 CONTINUE
C***ADD RECEIVER NOISE TO DIAGONAL ELEMENTS
 4444 DO 8006 ICH=1,NMAX
      COVNF(ICH,ICH)=COVNF(ICH,ICH)+1.0D0
 8006 CONTINUE
      DO 2727 I=1,NMAX
      DO 2727 J=1,NMAX
      IF(CDABS(COVNF(I,J)).EQ.0.0D0) GO TO 2727
      CNDB=10.*DLOG10(CDABS(COVNF(I,J)))
      PREALN=DREAL(COVNF(I,J))
      PIMAGN=DIMAG(COVNF(I,J))
      PHASEN=DATAN2(PIMAGN,PREALN)/DCR
      WRITE(8,4411)I,J,CNDB,PHASEN
      IF(I.EQ.1)WRITE(6,4411)I,J,CNDB,PHASEN
 4411 FORMAT(1X,'I,J,CNDB,PHASEN=',2I4,2X,2F12.2)
 2727 CONTINUE
C***COMPUTE COVARIANCE MATRIX INVERSE
      DO 8007 ICH=1,NMAX
```

```
      DO 8007 JCH=1,NMAX
      COVNFI(ICH,JCH)=COVNF(ICH,JCH)
8007  CONTINUE
      CALL DCMINV(COVNFI,LTMP,MTMP,NMAX,NMAX)
C***CHECK MATRIX INVERSION ACCURACY   (CINVERSE*C=I)
      CALL CMMULT(COVNFI,COVNF,NMAX,NMAX,NMAX,CINVCN)
      DO 8008 ICH=1,NMAX
      DO 8008 JCH=1,NMAX
      IF(ICH.EQ.1)WRITE(6,8009)ICH,JCH,CINVCN(ICH,JCH)
8009  FORMAT(1X,'ICH,JCH,CINVCN=',2I4,2X,2E12.5)
8008  CONTINUE
C***COMPUTE EIGENVALUES (ALSO EIGENVECTORS AND PERFORMANCE INDEX)
      IJOB=2
      CALL EIGCC(COVNF,NMAX,NMAX,IJOB,EIGVAN,EIGVEN,NMAX,WKE,IER)
      WRITE(6,155)IER
155   FORMAT(1X,'AFTER COMPUTE EIGENVALUES, IER=',I5)
      DO 200 I=1,NMAX
      WRITE(6,300)I,EIGVAN(I)
300   FORMAT(1X,'I,EIGVAN=',2X,I4,2E10.3)
200   CONTINUE
      DO 205 I=1,NMAX
      EVLDBN=10.*DLOG10(CDABS(EIGVAN(I)))
      WRITE(8,207)I,EVLDBN
      WRITE(6,207)I,EVLDBN
207   FORMAT(1X,'I,EVLDBN=',I4,2X,2F12.3)
205   CONTINUE
C***   CALL PRNTDA
C***FILL-IN SIDELOBE CANCELLER QUIESCENT WEIGHTS
      DO 8985 I=1,NMAX
      WQSLC(I,1)=DCMPLX(0.0D0,0.0D0)
8985  CONTINUE
      WQSLC(1,1)=DCMPLX(1.0D0,0.0D0)
      DO 7769 I=1,NMAX
      WRITE(6,1212)I,WQSLC(I,1)
      WRITE(8,1212)I,WQSLC(I,1)
1212  FORMAT(1X,'I,WQSLC=',I4,2X,2E12.5)
7769  CONTINUE
C***COMPUTE QUIESCENT INR
      IF(ISLC.EQ.1) CALL INRTIO(WQSLC,COVNF,NMAX,WTCTR,CMPROD,QINRDB)
      IF(ISLC.EQ.0) CALL INRTIO(CWTA,COVNF,NMAX,WTCTR,CMPROD,QINRDB)
      QINRAA=10.*DLOG10(CDABS(COVNF(1,1)))
C***COMPUTE AVERAGE CANCELLATION
      SUMC=0.0
      SUMAA=0.0
      DO 1829 IR=1,NRAN
C***ZERO-OUT ADAPTIVE WEIGHTS INITIALLY
      DO 57 I=1,NMAX
      WAN(I,1)=DCMPLX(0.0D0,0.0D0)
57    CONTINUE
C***COMPUTE ADAPTIVE ARRAY WEIGHTS
      IF(ISLC.EQ.1) CALL CMMULT(COVNFI,WQSLC,NMAX,NMAX,1,WAN)
      IF(ISLC.EQ.0) CALL CMMULT(COVNFI,CWTA,NMAX,NMAX,1,WAN)
C***QUANTIZE AND RANDOMIZE ADAPTIVE WEIGHT SETTINGS
      IF(IQUAN.EQ.1.AND.NBADWT.LT.20)
     2CALL ADQUAN(NMAX,WAN,NBADWT,IRNERR,INITRN,AWSGDB,AWSGDG)
C***NORMALIZE FULLY ADAPTIVE WEIGHTS
      IF(ISLC.EQ.0) THEN
         SAVE=0.0D0
         DO 33345 I=1,NEL
         SAVE=SAVE+CDABS(WAN(I,1))**2
33345    CONTINUE
         SAVESR=DSQRT(SAVE)
         DO 44456 I=1,NEL
         WAN(I,1)=WAN(I,1)/SAVESR
         WANDB=20.*DLOG10(CDABS(WAN(I,1)))
         IF(IR.EQ.1) WRITE(6,3599)I,WANDB
         IF(IR.EQ.1) WRITE(8,3599)I,WANDB
3599     FORMAT(1X,'I=',I4,2X,'WANDB=',1X,F12.3)
44456    CONTINUE
      ENDIF
C****TO PRINT NORMALIZED WEIGHTS
      BIGWDB=-299.0
      DO 9102 I=1,NMAX
      IF(IR.EQ.1) WRITE(6,6191)I,WAN(I,1)
```

```
      IF(IR.EQ.1) WRITE(8,6191)I,WAN(I,1)
6191  FORMAT(1X,'I,WAN(I,1)=',I4,2X,2E12.5)
      WANDBM=20.*DLOG10(CDABS(WAN(I,1)))
      IF(WANDBM.GT.BIGWDB) BIGWDB=WANDBM
9102  CONTINUE
      DO 9112 I=1,NMAX
      WANDB=20.*DLOG10(CDABS(WAN(I,1)))-BIGWDB
      WANDG=DATAN2(DIMAG(WAN(I,1)),DREAL(WAN(I,1)))/DCR
      IF(IR.EQ.1) WRITE(6,35991)I,WANDB,WANDG
      IF(IR.EQ.1) WRITE(8,35991)I,WANDB,WANDG
35991 FORMAT(1X,'I=',I4,2X,'WANDB,WANDG=',1X,2F14.5)
9112  CONTINUE
C***COMPUTE ADAPTED INR
      CALL INRTIO(WAN,COVNF,NMAX,WTCTR,CMPROD,AINRDB)
C***COMPUTE CANCELLATION
      CANCDB=AINRDB-QINRDB
      WRITE(6,3007)QINRDB,AINRDB,CANCDB
      WRITE(8,3007)QINRDB,AINRDB,CANCDB
3007  FORMAT(1X,'INR= QUI,ADAP ,CANCEL=',2X,3F10.3,2X,' DB')
      SUMC=SUMC+CANCDB
C***COMPUTE ADAPTED INR CH. A
      DO 2255 I=1,NMAX
      WANDMA(I,1)=WAN(I,1)
      IF(I.GT.NMAX) WANDMA(I,1)=(0.0D0,0.0D0)
2255  CONTINUE
      CALL INRTIO(WANDMA,COVNF,NMAX,WTCTR,CMPROD,AINRAA)
C***CANCELLATION CH. A
      CNCLNA=AINRAA-QINRAA
      WRITE(6,3738)QINRAA,AINRAA,CNCLNA
      WRITE(8,3738)QINRAA,AINRAA,CNCLNA
3738  FORMAT(1X,'SIDELOBE CANCELLER CH. A INR= QUI,ADAP,CAN=',2X,3F10.3)
      SUMAA=SUMAA+CNCLNA
1829  CONTINUE
      AVECAN=SUMC/NRAN
      WRITE(6,4456)CANCDB,NRAN,AVECAN
4456  FORMAT(1X,'CANCDB,NRAN,AVECAN=',F12.5,2X,I5,2X,F12.5)
      WRITE(8,4456)CANCDB,NRAN,AVECAN

AVECAA=SUMAA/NRAN
      WRITE(6,2220)AVECAA
      WRITE(8,2220)AVECAA
2220  FORMAT(1X,'AVE. CANEL, CH. A, =',2X,F12.5)
C***SECTION TO COMPUTE ADAPTIVE ARRAY RADIATION PATTERNS
CC    IF(INEAR.EQ.0.OR.IANGLP.EQ.0) GO TO 9990
      IF(INEAR.EQ.0) GO TO 9990
      BIGADB=-299.
      IC=0
      DO 8919 IZ=1,NCOLZN
      DO 8919 IY=1,NROWYN
      DO 8919 IX=1,NCOLXN
      IC=IC+1
      CSUMA=(0.,0.)
      IF(ISLC.EQ.1) CSUMA=CSUMA+DCONJG(WAN(1,1))*VXMANA(IC)
      DO 7921 IAX=1,NAUX
      IAXP1=IAX+1
      IF(ISLC.EQ.1) CSUMA=CSUMA+DCONJG(WAN(IAXP1,1))*VAXCWA(IAX,IC)
      IF(ISLC.EQ.0) CSUMA=CSUMA+DCONJG(WAN(IAX,1))*VAXCWA(IAX,IC)
7921  CONTINUE
      IF(CABS(CSUMA).EQ.0.) CSUMA=(1.E-10,0.)
      PCHADB(IC)=20.*ALOG10(CABS(CSUMA))
      IF(PCHADB(IC).GT.BIGADB) BIGADB=PCHADB(IC)
CC    WRITE(6,4999)IC,PCHADB(IC)
8919  CONTINUE
C***NORMALIZE ADAPTIVE PATTERNS
      IF(IXZ.EQ.1) WRITE(31,18889)
      IF(IXZ.EQ.1) WRITE(31,18888)XN,NCOLXN,DXN,ZN,NCOLZN,DZN
      IF(IXZ.EQ.1) WRITE(31,4546)
      IC=0
      DO 3459 IZ=1,NCOLZN
      DO 3459 IY=1,NROWYN
      DO 3459 IX=1,NCOLXN
      IC=IC+1
      PCHADB(IC)=PCHADB(IC)-BIGADB
      IF(IPCONN.EQ.0) WRITE(31,*)IZ,IX,PCHADB(IC)
      IF(IPCONN.EQ.0) GO TO 3459
```

```
            IF(IXY.EQ.1) FM(IY,IX)=PCHADB(IC)
            IF(IXZ.EQ.1) FM(IZ,IX)=PCHADB(IC)
            IF(IXZ.EQ.1.AND.IPCONN.EQ.1) WRITE(31,*) IZ,IX,FM(IZ,IX)
 3459    CONTINUE
            WRITE(25,*)NCOLXN
            DO 1879 IDDD=1,NCOLXN
            WRITE(25,*)PCHADB(IDDD)
 1879    CONTINUE
            IF((NCOLXN.GT.1.OR.NROWYN.GT.1).AND.IPLOTN.EQ.1.AND.IANGLP.EQ.0)
           2CALL PLOTTR(NCOLXN,NROWYN,NCOLZN,XC,YC,ZC,NPTSN,PCHADB,PCHADB,
           3PCHADB,PCHADB)
            IF(IPCONN.EQ.1.AND.IXY.EQ.1)
           2CALL PLCONT(NCOLXN,NROWYN,NCLXN2,NRWYN2,RX,RY,
           3FM,DMF,-50.,10.,5,1)
            IF(IPCONN.EQ.1.AND.IXZ.EQ.1)
           2CALL PLCONT(NCOLXN,NCOLZN,NCLXN2,NCLZN2,RX,RZ,
           3FM,DMF,-50.,10.,5,1)
 9990    CONTINUE
 9999    CONTINUE
            CALL DONEPL
            CALL GETCP2(CPUL)
            CPUTOT=CPUL-CPU1
            WRITE(6,2006)CPUTOT
 2006    FORMAT(1X,'TOTAL CPU TIME=',F15.2)
            STOP
            END
C***SUBROUTINE TO COMPUTE IMPEDANCE MATRIX
            SUBROUTINE ZMATRX(CTDP,STDP,IBLTSL,ICC1,ICC,CZ,Z)
            COMPLEX Z(ICC1,ICC),CZ(1)
            COMMON/A/DX,DY,NCOLX,NROWY,NEL,HZ,HL,ARAD,ZLOAD,ZCHAR
            COMMON /GROUND/ IGRNDP
            COMMON /CIRCLE/ ICIRC,RADIUS,HLS
            NB=NCOLX
            IDMB=NROWY
C***COMPUTE MUTUAL IMPEDANCES Z(1,1),Z(1,2),Z(1,3),...,Z(1,NEL).
CC       CALL RGDZMN(IGRNDP,ICC1,ICC,Z)
CC       CALL RGDZAB(CTDP,STDP,IGRNDP,ICC1,ICC,Z)
            IF(ICIRC.EQ.0) CALL RGDZA2(CTDP,STDP,IGRNDP,ICC1,ICC,Z)
            IF(ICIRC.EQ.1) CALL CADZA2(CTDP,STDP,IGRNDP,ICC1,ICC,Z)
            WRITE(8,10) NEL,NCOLX,NROWY
 10      FORMAT(1X,'NEL,NCOLX,NROWY=',3I5)
            ICOUNT=0
            DO 20 I=1,NCOLX
            DO 20 J=1,NROWY
            ICOUNT=ICOUNT+1
            WRITE(6,80) I,J,Z(1,ICOUNT)
 80      FORMAT(1X,'I,J,Z(1,ICOUNT)=',2I4,2X,2E12.5)
 20      CONTINUE
            IDM=NEL
            ICC=NEL
C***FILL THE IMPEDANCE MATRIX
            IF(NCOLX.LE.1) GO TO 70
            IBLT=IBLTSL
            IDM1=IDMB
            IF(IBLT.EQ.0) IDM1=NEL
            IF(NROWY.GT.1) GO TO 40
C***FILL TOEPLITZ MATRIX
            DO 30 I=2,NEL
            DO 30 J=I,NEL
            K=1+J-I
            Z(I,J)=Z(1,K)
 30      CONTINUE
            GO TO 50
 40      CALL BTOEPL(IBLT,NB,IDMB,IDM1,IDM,Z)
 50      CONTINUE
            IF(IBLT.EQ.0) GO TO 70
            DO 60 I=1,IDMB
            DO 60 J=1,IDM
              IC=(J-1)*IDMB+I
              CZ(IC)=Z(I,J)
CC       WRITE(8,7878)I,J,Z(I,J)
 7878    FORMAT(1X,'I,J,Z(I,J)=',2I4,2X,2E12.5)
 60      CONTINUE
```

```
      70    CONTINUE
            RETURN
            END
C***SUBROUTINE TO COMPUTE RECEIVE BEAMFORMER WEIGHTS
            SUBROUTINE VRCVWT(NACOLX,NAROWY,NXDUM,NYDUM,EDGTDB,WA,WB)
            DIMENSION WA(1),WB(1)
            DIMENSION WT(180)
            COMMON/A/DX,DY,NCOLX,NROWY,NEL,HZ,HL,ARAD,ZLOAD,ZCHAR
            COMMON /CHEBY/ ICHEB,SLLDB
            PI=3.141592654
            TPI=2.*PI
            DCR=PI/180.
      CC    SLLDB=40.
            TAP=10.**(EDGTDB/20.)
            WRITE(6,*)TAP
            AMP=(1.-TAP)/2.
            NPDX=NCOLX-NACOLX-2*NXDUM
            AXL=DX*(NACOLX-1)
            AYL=DY*(NAROWY-1)
            IF(TAP.NE.1.0)FX=AXL/2.*PI/ACOS(TAP)
            IF(TAP.NE.1.0)FY=AYL/2.*PI/ACOS(TAP)
            WRITE(6,20)
      20    FORMAT(1X,'BEFORE CALL CHEBWT')
            WRITE(6,30)SLLDB
      30    FORMAT(1X,'SLLDB=',2X,F10.2)
            IF(ICHEB.EQ.1)CALL CHEBWT(NACOLX,SLLDB,WT,RLOSS)
            WRITE(6,40)
      40    FORMAT(1X,'AFTER CHEBWT')
            DO 1000 IC=1,NEL
            WA(IC)=0.0
            WB(IC)=0.0
      1000  CONTINUE
C***COMPUTE EFFECTIVE DIPOLE CENTER COORDS. FOR BOTH PHASE CENTERS
            X0=-AXL/2.
            Y0=-AYL/2.
            IC=0
            DO 80 I=1,NACOLX
            DO 80 J=1,NAROWY
            IC=IC+1
            X=X0+DX*(I-1)
            Y=Y0+DY*(J-1)
            TAPERX=1.0
            TAPERY=1.0
            IF(ICHEB.EQ.1) GO TO 70
            IF(TAP.NE.1.0)TAPERX=COS(PI*X/FX)
            IF(TAP.NE.1.0.AND.FY.NE.0.0)TAPERY=COS(PI*Y/FY)
      60    TAPER=TAPERX*TAPERY
            WT(IC)=TAPER
      70    CONTINUE
      80    CONTINUE
C***TRANSFORM FROM SUB-APERTURES TO FULL ARRAY
            IBGNA=NXDUM*NROWY+NYDUM
            IBGNB=IBGNA+NPDX*NROWY
            IC=0
            DO 1010 IX=1,NACOLX
            DO 1010 IY=1,NAROWY
            IC=IC+1
            IA=IBGNA+(IX-1)*NROWY+IY
            IB=IBGNB+(IX-1)*NROWY+IY
            WA(IA)=WT(IC)
            WB(IB)=WT(IC)
      1010  CONTINUE
            RETURN
            END
C***SUBROUTINE TO COVARIANCE MATRIX BASED ON NUMERICAL INTEGRATION
C***IN THE FREQUENCY DOMAIN ACCORDING TO SIMPSON'S RULE
            SUBROUTINE COVSWC(VA,VB,NCHAN,NFREQ,BWFHZ,COVAB)
            COMPLEX *16 VA(NCHAN,NFREQ),VB(NCHAN,NFREQ)
            COMPLEX *16 COVAB(NCHAN,NCHAN),CSUM,DCABF
            REAL *8 SWC(101)
            DELTAF=BWFHZ/(NFREQ-1)
            CALL SIMWC(NFREQ,SWC)
            DO 10 ICH=1,NCHAN
            DO 10 JCH=1,NCHAN
```

```
      CSUM=(0.0D0,0.0D0)
      DO 20 IFR=1,NFREQ
      DCABF=VA(ICH,IFR)*DCONJG(VB(JCH,IFR))
      CSUM=CSUM+DCABF*SWC(IFR)
CC    WRITE(6,6767)IFR,CSUM
6767  FORMAT(1X,'IFR,CSUM=',I4,2X,2E12.5)
20    CONTINUE
      COVAB(ICH,JCH)=DELTAF/2.*CSUM
C***NEW LINE TO NORMALIZE COVAB
      COVAB(ICH,JCH)=COVAB(ICH,JCH)/BWFHZ
CC    WRITE(6,4567)ICH,JCH,COVAB(ICH,JCH)
4567  FORMAT(1X,'ICH,JCH,COVAB(ICH,JCH)=',2I4,2X,2E12.5)
10    CONTINUE
      RETURN
      END
C***SUBROUTINE TO GENERATE SIMPSON'S 1/3 RULE WEIGHTING COEF.
C***INTGERAL F(X)DX=(DELTAX/3.)*(F(1)+4*F(2)+2*F(3)+4*F(4)+...+F(OOD))
C*** THE SERIES 1 4 2 4 2 4 .....1 ARE SIMPSON'S COEF.
      SUBROUTINE SIMWC(NCOEF,SWC)
      REAL *8 SWC(NCOEF)
      DO 10 N=1,NCOEF
      XNN=FLOAT(N)
      NN=N/2
      TT=XNN/2.
      DIF=TT-FLOAT(NN)
      NC=2
      IF(DIF.EQ.0.) NC=4
      IF(N.EQ.1.OR.N.EQ.NCOEF) NC=1
      SWC(N)=NC
10    CONTINUE
      RETURN
      END
C***SUBROUTINE TO COMPUTE RECEIVED VOLTAGES DUE TO JAMMER SOURCES
      SUBROUTINE VJAMMR(NJM,NEL,PWRJDB,ICC1,ICC,PS,CZ,Z,CWTA
     1,NB,IDMB,NAUX,IAUXA,ZLOAD,XJAMIN,YJAMIN,ZJAMIN,
     2IFR,NFR,CTPR,STPR,CTDP,STDP,VMAINA,VAUXA)
      COMPLEX *16 CWTA(NEL,1)
      COMPLEX PS(1),CZ(1),Z(ICC1,ICC)
      COMPLEX VJM(180),VREFJM
      COMPLEX CJ,CSUMA
      COMPLEX *16 VMAINA(NJM,NFR)
      COMPLEX *16 VAUXA(NAUX,NJM,NFR)
      DIMENSION PWRJDB(1),PWRJ(10)
      DIMENSION XJAMIN(1),YJAMIN(1),ZJAMIN(1)
      INTEGER IAUXA(1)
      COMMON/PCENTR/PCDXIN
      COMMON /B/ NGEN,IGEN,THETAS,PHIS,IMUT,IBLTSL,IPATRN
      COMMON /D/ FGHZ,RLAMDA,IWL,IS,NSCANS
      COMMON /WRITE/ IWR
      COMMON /CIRCLE/ ICIRC,RADIUS,HLS
      PI=3.141592654
      DCR=PI/180.
      CJ=(0.,1.)
      CINMTR=0.0254
      ISYM=0
C***CONVERT DB TO POWER (RELATIVE TO NOISE)
      DO 10 II=1,NJM
      PWRJ(II)=10.**(PWRJDB(II)/10.)
      WRITE(6,66)II,PWRJ(II)
      WRITE(8,66)II,PWRJ(II)
66    FORMAT(1X,'II,PWRJ IN POWER=',I4,2X,E12.5)
10    CONTINUE
      IF(IFR.GT.1) GO TO 55
      WRITE(6,20)IWL
      DO 5544 IJAM=1,NJM
      WRITE(6,40)
      WRITE(6,50)XJAMIN(IJAM),YJAMIN(IJAM),ZJAMIN(IJAM)
5544  CONTINUE
20    FORMAT(1X,'IWL=',I4)
      WRITE(6,30)
30    FORMAT(1X,'CHANGE NEAR FIELD JAMMER POSITIONS (INCHES)?, ICH=1')
      READ(5,*)ICH
      IF(ICH.EQ.0) GO TO 55
```

```
          DO 8887 IJAM=1,NJM
          WRITE(6,40)
40        FORMAT(1X,'XJAMIN,YJAMIN,ZJAMIN,=')
          READ(5,*,END=55)XJAMIN(IJAM),YJAMIN(IJAM),ZJAMIN(IJAM)
          WRITE(6,50)XJAMIN(IJAM),YJAMIN(IJAM),ZJAMIN(IJAM)
50        FORMAT(1X,5F10.3,2X,2I5)
8887      CONTINUE
55        CONTINUE
          PCDX=PCDXIN*CINMTR
          WRITE(6,4757)IFR
4757      FORMAT(1X,'FREQ. INDEX, IFR=',I4)
60        CONTINUE
C**ALL DIMENSIONS IN METERS
          DO 180 IPHACN=1,1
          WRITE(6,2223)IPHACN
2223      FORMAT(1X,'IPHACN=',I4)
          XREFDP=-PCDX/2.+(IPHACN-1)*PCDX
C***PERFORM JAMMER SOURCE SCAN
          DO 180 IJAM=1,NJM
          X=XJAMIN(IJAM)*CINMTR+PCDX*(IPHACN-1)
          Y=YJAMIN(IJAM)*CINMTR
          ZPOS=ZJAMIN(IJAM)*CINMTR
          WRITE(6,6688)X,Y,ZPOS,XREFDP
6688      FORMAT(1X,'X,Y,ZPOS,XREFDP (METERS)=',4F12.4)
          IF(ICIRC.EQ.0)
         2CALL NFDPX2(CTPR,STPR,CTDP,STDP,X,Y,ZPOS,XREFDP,1,VJM,VREFJM)
          IF(ICIRC.EQ.1)
         2CALL NFDPC2(X,Y,ZPOS,XREFDP,1,VJM,VREFJM)
C***NORMALIZE INCIDENT JAMMER POWER
          DO 70 INORM=1,NEL
          VJM(INORM)=VJM(INORM)/VREFJM*SQRT(PWRJ(IJAM))
          WRITE(6,77)INORM,VJM(INORM)
77        FORMAT(1X,'INORM,VJM(INORM) VOLTAGE=',I4,2X,2E12.5)
70        CONTINUE
          IF(IMUT.EQ.0) GO TO 90
C***SOLVE EACH SYSTEM OF EQUATIONS FOR THE UNKNOWN CURRENTS
          IF(IBLTSL.EQ.1) GO TO 80
          I12=1
          IF(IJAM.GT.1.OR.IPHACN.GT.1) I12=2
          WRITE(6,6110)
6110      FORMAT(1X,'CALL CROUT IN VJAMMER')
          CALL CROUT(Z,VJM,ICC1,ICC,ISYM,IWR,I12,NEL)
          GO TO 90
80        IENTRY=4
          IF(IJAM.GT.1.OR.IPHACN.GT.1) IENTRY=3
          CALL BLTSOL(CZ,VJM,PS,NB,IDMB,IENTRY)
          IF(NEL.LT.40) CALL CNORM(VJM,NEL)
90        CONTINUE
C***COMPUTE RECEIVED VOLTAGES FOR PRESENT SOURCE POSITION
          DO 100 IEL=1,NEL
          VJM(IEL)=VJM(IEL)*ZLOAD
CC        WRITE(6,4456)IEL,VJM(IEL)
4456      FORMAT(1X,'IEL,VJM(IEL) RECEIVED VOLT.=',I4,2X,2E12.5)
100       CONTINUE
C***PERFORM BEAM FORMATION FOR MAIN A
C***PHASE CENTER A
          CSUMA=(0.0D0,0.0D0)
          DO 110 KC=1,NEL
          CSUMA=CSUMA+VJM(KC)*CWTA(KC,1)
110       CONTINUE
          VMAINA(IJAM,IFR)=CSUMA
          WRITE(6,2222)IJAM,IFR,VMAINA(IJAM,IFR)
2222      FORMAT(1X,'IJAM,IFR,VMAINA= (AFTER B.F.)',2I4,2X,2E12.5)
C***COMPUTE AUXILIARY CHANNEL VOLTAGES
          DO 7000 IAUX=1,NAUX
          VAUXA(IAUX,IJAM,IFR)=VJM(IAUXA(IAUX))
7000      CONTINUE
180       CONTINUE
          DO 9000 IJAM=1,NJAMS
CCC       WRITE(6,4433)IJAM,IFR,VMAINA(IJAM,IFR)
4433      FORMAT(1X,'VJAMMR:IJAM,IFR,VMAINA=',2I4,2X,2E12.5)
          DO 9001 IAUX=1,NAUX
          WRITE(6,3333)IAUX,IJAM,IFR,VAUXA(IAUX,IJAM,IFR)
```

```
3333    FORMAT(1X,'VJAMMR:IAUX,IJAM,IFR,VAUXA=',3I4,2X,2E12.5)
9001    CONTINUE
9000    CONTINUE
        RETURN
        END
C***SUBROUTINE TO COMPUTE INTERFERENCE TO NOISE RATIO
        SUBROUTINE INRTIO(WT,COV,NEL,WTCTR,CMPROD,DBINR)
        IMPLICIT REAL *8 (A-H,O-Z)
        COMPLEX *16 WT(NEL,1),COV(NEL,NEL),WTCTR(1,NEL)
        COMPLEX *16 CMPROD(1,NEL),CPROD1(1,1),CPROD2(1,1),CINR
        COMMON /NORMAL/ INRNOR
        WRITE(12,2222)
2222    FORMAT(1X,'INSIDE INRTIO SUBROUTINE')
        DO 110 I=1,NEL
CC      WRITE(12,445)I,WT(I,1)
445     FORMAT(1X,'I,WT(I,1)=',2X,I4,2X,2E12.5)
110     CONTINUE
        CALL CONJTR(WT,NEL,1,WTCTR)
        DO 111 I=1,NEL
CC      WRITE(12,666)I,WT(I,1),WTCTR(1,I)
666     FORMAT(1X,'I,WT,WTCTR=',2X,I4,2X,4E12.5)
111     CONTINUE
        CALL CMMULT(WTCTR,COV,1,NEL,NEL,CMPROD)
        CALL CMMULT(CMPROD,WT,1,NEL,1,CPROD1)
        CALL CMMULT(WTCTR,WT,1,NEL,1,CPROD2)
        WRITE(6,333)CPROD1(1,1),CPROD2(1,1)
        WRITE(8,333)CPROD1(1,1),CPROD2(1,1)
333     FORMAT(1X,'CPROD1,CPROD2=',4E12.5)
C***INR NORMALIZED
CC      INRNOR=0
        WRITE(6,7739)INRNOR
        WRITE(8,7739)INRNOR
7739    FORMAT(1X,'INR NORMALIZATION PARAMETER, INRNOR=',I4)
        IF(INRNOR.EQ.1) CINR=CPROD1(1,1)/CPROD2(1,1)
C***INR NOT NORMALIZED FOR INRNOR=0
        IF(INRNOR.EQ.0) CINR=CPROD1(1,1)
        DBINR=10.*DLOG10(CDABS(CINR))
        RETURN
        END
        SUBROUTINE CMMULT(A,B,L,M,N,C)
        COMPLEX *16 A(L,M),B(M,N),C(L,N)
        DO 20 I=1,L
        DO 20 J=1,N
        C(I,J)=DCMPLX(0.0D0,0.0D0)
        DO 20 K=1,M
        C(I,J)=C(I,J)+(A(I,K)*B(K,J))
20      CONTINUE
        RETURN
        END
C***SUBROUTINE TO COMPUTE CONJUGATE TRANSPOSE OF A MATRIX
        SUBROUTINE CONJTR(A,L,M,ACTR)
        COMPLEX *16 A(L,M),ACTR(M,L)
        DO 10 I=1,M
        DO 10 J=1,L
        ACTR(I,J)=DCONJG(A(J,I))
CC      WRITE(12,7766)I,J,A(J,I),ACTR(I,J)
7766    FORMAT(1X,'I,J,A(J,I),ACTR(I,J)=',2X,2I4,2X,4E12.5)
10      CONTINUE
        RETURN
        END
        SUBROUTINE DCMINV(A,L,M,IDM,NEQ)
        COMPLEX *16 A(IDM,IDM),BIGA,HOLD,DET
        INTEGER L(IDM),M(IDM)
        N=NEQ
        DET=DCMPLX(1.0D0,0.0D0)
        DO 80 K=1,N
        L(K)=K
        M(K)=K
        BIGA=A(K,K)
        DO 20 J=K,N
        DO 20 I=K,N
10      IF(CDABS(BIGA)-CDABS(A(I,J)))15,19,19
15      BIGA=A(I,J)
```

```
            L(K)=I
            M(K)=J
19     CONTINUE
20     CONTINUE
            J=L(K)
            IF(J-K)35,35,25
25     CONTINUE
            DO 30 I=1,N
            HOLD=-A(K,I)
            A(K,I)=A(J,I)
30     A(J,I)=HOLD
35     I=M(K)
            IF(I-K) 45,45,38
38     CONTINUE
            DO 40 J=1,N
            HOLD=-A(J,K)
            A(J,K)=A(J,I)
40     A(J,I)=HOLD
45     CONTINUE
            DO 55 I=1,N
            IF(I-K)50,55,50
50     A(I,K)=A(I,K)/(-BIGA)
55     CONTINUE
            DO 65 I=1,N
            DO 65 J=1,N
            IF(I-K)60,64,60
60     IF(J-K)62,64,62
62     A(I,J)=A(I,K)*A(K,J)+A(I,J)
64     CONTINUE
65     CONTINUE
            DO 75 J=1,N
            IF(J-K)70,75,70
70     A(K,J)=A(K,J)/BIGA
75     CONTINUE
            DET=DET*BIGA
            A(K,K)=1.0D0/BIGA
80     CONTINUE
            K=N
100    K=K-1
            IF(K)150,150,105
105    I=L(K)
            IF(I-K)120,120,108
108    CONTINUE
            DO 110 J=1,N
            HOLD=A(J,K)
            A(J,K)=-A(J,I)
110    A(J,I)=HOLD
120    J=M(K)
            IF(J-K)100,100,125
125    CONTINUE
            DO 130 I=1,N
            HOLD=A(K,I)
            A(K,I)=-A(J,I)
130    A(J,I)=HOLD
            GO TO 100
150    RETURN
            END
C***SUBROUTINE CNORM
C***COMPUTES A NORMALIZED COMPLEX COLUMN VECTOR SUCH THAT THE
C***MAXIMUM ELEMENT HAS UNITY MAGNITUDE.
C
C***PRINTS MAGNITUDE AND PHASE OF NORMALIZED VECTOR
C
            SUBROUTINE CNORM(V,N)
C***     V IS THE INPUT COMPLEX COLUMN VECTOR
```

```
C***      N IS THE LENGTH OF V
          COMPLEX V(1),SS
          CNOR=0.0
          DO 10 K=1,N
          SA=CABS(V(K))
          IF(SA.GT.CNOR) CNOR=SA
10        CONTINUE
          IF(CNOR.LE.0.) CNOR=1.0
          DO 30 K=1,N
          SS=V(K)
          SA=CABS(SS)
          SNOR=SA/CNOR
          PHR=0.
          IF(SA.GT.0.) PHR=ATAN2(AIMAG(SS),REAL(SS))
          PH=57.29578*PHR
          WRITE(8,20) K,SNOR,SA,PH
20        FORMAT(1X,I5,F10.6,3X,E15.3,F10.0)
30        CONTINUE
          RETURN
          END
          SUBROUTINE GETCP2(RCPU)
          REAL ETIME,TARRAY(2),RCPU
          TIME=ETIME(TARRAY)
          RCPU=TARRAY(1)
          RETURN
          END
C***SUBROUTINE TO COMPUTE INDUCED VOLTAGE BETWEEN PROBE AND
C***DIPOLE ARRAY ELEMENTS
C***RING ARRAY
          SUBROUTINE NFDPC2(XP,YP,ZP,XREF,IREF,V,VREF)
C***DISTANCES ARE IN METERS
          COMPLEX V(1),VD,VR1,VREF
          COMPLEX *16 DZABG
          COMMON/A/DX,DY,NCOLX,NROWY,NEL,HZ,HL,ARAD,ZLOAD,ZCHAR
          COMMON /CIRCLE/ ICIRC,RADIUS,HLS
C***NOTE: AA,BB,... FOR PROBE    11,22,... FOR DIPOLE
          PI=3.1415926535
          DCR=PI/180.
C***PROBE DIMENSIONS
          XAA=XP
          XBB=XP
          XCC=XP
          YAA=YP-HLS
          YBB=YP
          YCC=YP+HLS
785       ZAA=ZP
          ZBB=ZP
          ZCC=ZP
          IC=0
C****CIRCULAR DIPOLE ARRAY ELEMENTS
          DELPHI=360./NEL
          DO 10 IX=1,NEL
          PHI=DELPHI*(IX-1)
          XD=RADIUS*COS(PHI*DCR)
          ZD=RADIUS*SIN(PHI*DCR)
          DIST=SQRT((XP-XD)**2+(ZP-ZD)**2)
          IF(DIST.LT.ARAD) XD=XD+ARAD
          X11=XD
          X22=XD
          X33=XD
          Y11=YP-HL
          Y22=YP
          Y33=YP+HL
          Z11=ZD
          Z22=ZD
          Z33=ZD
9446      IC=IC+1
CC        WRITE(6,2233)IX,IY,XD,YD
2233      FORMAT(1X,'IX,IY,XD,YD=',2X,2I4,2X,2F12.5)
CC        WRITE(6,7854)XAA,XBB,XCC,YAA,YBB,YCC,ZAA,ZBB,ZCC
7854      FORMAT(1X,'XYZABC=',9E12.5)
CC        WRITE(6,7855)X11,X22,X33,Y11,Y22,Y33,Z11,Z22,Z33
7855      FORMAT(1X,'XYZ123=',9E12.5)
```

```
        CALL DSZABG(XAA,XBB,XCC,YAA,YBB,YCC,ZAA,ZBB,ZCC,X11,X22,X33,
       2Y11,Y22,Y33,Z11,Z22,Z33,DZABG)
        VD=DZABG
CC      WRITE(6,33)IC,VD
33      FORMAT(1X,'IC,VD=',2X,I5,2E12.5)
        V(IC)=VD
        VAMPDB=20.*ALOG10(CABS(V(IC)))
        VPHASE=ATAN2(AIMAG(V(IC)),REAL(V(IC)))*180./3.141592654
CC      WRITE(6,4455)IC,VAMPDB,VPHASE
4455    FORMAT(1X,'IC,VAMDB,VPHASE=',2X,I4,2X,2F12.2)
10      CONTINUE
C***COMPUTE REFERENCE VOLTAGE (FICTITIOUS ELEMENT AT XREF, Y=0)
C***SET XREF=RADIUS, THIS MAKES ELEMENT 1 THE REFERENCE
        XREF=RADIUS
C***SET XREF=ARAD, (REF. CLOSE TO THE ORIGIN)
        XREF=ARAD
        X11=XREF
        X22=XREF
        X33=XREF
        Y11=-HL
        Y22=0.0
        Y33=HL
        Z11=0.0
        Z22=0.0
        Z33=0.0
9267    CALL DSZABG(XAA,XBB,XCC,YAA,YBB,YCC,ZAA,ZBB,ZCC,X11,X22,X33,
       2Y11,Y22,Y33,Z11,Z22,Z33,DZABG)
        VR1=DZABG
        VREF=VR1
99      RETURN
        END
C***SUBROUTINE TO COMPUTE MUT. IMPED. BETWEEN STRAIGHT DIPOLES
C***ARRANGED IN A RING ARRAY (CIRCLE)
        SUBROUTINE CADZA2(CTDP,STDP,IGRNDP,ICC1,ICC,Z)
        COMPLEX ZMA,ZABG,Z(ICC1,ICC)
        COMMON /A/ DX,DY,NCOLX,NROWY,NEL,HZ,HL,ARAD,ZLOAD,ZCHAR
        COMMON /CIRCLE/ ICIRC,RADIUS,HLS
C***ALL DIMENSIONS IN METERS
        PI=3.1415926535
        DCR=PI/180.
C***FIXED POSITION FOR ELEMENT 1
        XAA=RADIUS
        XBB=RADIUS
        XCC=RADIUS
        YAA=-HL
        YBB=0.0
        YCC=HL
        ZAA=0.0
        ZBB=0.0
        ZCC=0.0
        Y11=YAA
        Y22=YBB
        Y33=YCC
C***VARIABLE POSITION FOR RING ARRAY ELEMENTS
        DELPHI=360./NEL
        IC=0
        DO 20 I=1,NEL
        IC=IC+1
        PHI=DELPHI*(I-1)*DCR
        XD=RADIUS*COS(PHI)
        ZD=RADIUS*SIN(PHI)
        X11=XD
        X22=XD
        X33=XD
        IF(I.EQ.1) X11=X11+ARAD
        IF(I.EQ.1) X22=X22+ARAD
        IF(I.EQ.1) X33=X33+ARAD
        Z11=ZD
        Z22=ZD
        Z33=ZD
CC      WRITE(6,87)IC
87      FORMAT(1X,'IC=',I5)
CC      WRITE(6,88)XAA,XBB,XCC,YAA,YBB,YCC,ZAA,ZBB,ZCC
```

```
88      FORMAT(1X,'XYZABC=',9E12.4)
CC      WRITE(6,89)X11,X22,X33,Y11,Y22,Y33,Z11,Z22,Z33
89      FORMAT(1X,'XYZ123=',9E12.4)
        ZMA=ZABG(XAA,XBB,XCC,YAA,YBB,YCC,ZAA,ZBB,ZCC,X11,X22,X33,
       2Y11,Y22,Y33,Z11,Z22,Z33)
        Z(1,IC)=ZMA
        IF(IC.EQ.1) Z(1,1)=Z(1,1)+ZLOAD
20      CONTINUE
        DO 40 I=1,NEL
        IF(I.LT.9)WRITE(6,30)I,Z(1,I)
        WRITE(8,30)I,Z(1,I)
30      FORMAT(1X,'Z(1,',I4,')=',2E12.5)
40      CONTINUE
        RETURN
        END
**********file zabgenloss.f********************
C***PROGRAM TO CALCULATE MUTUAL IMPEDANCE BETWEEN TWO DIPOLES
C***WITH ARBITRARY LENGTH AND ORIENTATION. A PIECEWISE-
C***SINUSOIDAL CURRENT DISTRIBUTION IS ASSUMED.
                    C O M P L E X     F U N C T I O N
        ZABG(X1,X2,X3,Y1,Y2,Y3,Z1,Z2,Z3,XA,XB,XC,YA,YB,YCZAB00040
       2,ZA,ZB,ZC)
        COMPLEX P11,P12,P21,P22,Q11,Q12,Q21,Q22,R11,R12,R21,R22
        COMPLEX S11,S12,S21,S22,JCOM,GAM,CGDS,SGDS,SGDT,ETA,EP3
        COMPLEX EGDS,EGDT
        COMMON /F/ FHZ,ER3,SIG3,TD3
C***ALL DIMENSIONS IN METERS
        PI=3.141592654
        TPI=2.*PI
        B=TPI
        JCOM=(0.,1.)
        E0=8.854E-12
        U0=1.2566E-6
        OMEGA=TPI*FHZ
        IF(SIG3.LT.0.)EP3=ER3*E0*CMPLX(1.,-TD3)
        IF(TD3.LT.0.)EP3=CMPLX(ER3*E0,-SIG3/OMEGA)
        ETA=CSQRT(U0/EP3)
        GAM=OMEGA*CSQRT(-U0*EP3)
        AM=0.0001
        IF(CABS(GAM*AM).GT.0.06) WRITE(6,7923)AM
7923    FORMAT(1X,'CABS(GAM*AM) IS GREATER THAN 0.06, AM=',E14.5)
        INT=0
        XBA=XB-XA
        YBA=YB-YA
        ZBA=ZB-ZA
        X21=X2-X1
        Y21=Y2-Y1
        Z21=Z2-Z1
        DS=SQRT(XBA*XBA+YBA*YBA+ZBA*ZBA)
        DT=SQRT(X21*X21+Y21*Y21+Z21*Z21)
CC      DSK=B*DS
CC      DTK=B*DT
CC      CGDS=CMPLX(COS(DSK),0.0)
CC      SGDS=CMPLX(0.0,SIN(DSK))
CC      SGDT=CMPLX(0.0,SIN(DTK))
C***FOR LOSSY MEDIUM THE NEXT LINES ARE APPROPRIATE
        EGDS=CEXP(GAM*DS)
        EGDT=CEXP(GAM*DT)
        CGDS=(EGDS+1./EGDS)/2.
        SGDS=(EGDS-1./EGDS)/2.
        SGDT=(EGDT-1./EGDT)/2.
CC      WRITE(6,1345)XA,XB,YA,YB,ZA,ZB
1345    FORMAT(1X,'XYZAB=',6E14.5)
CC      WRITE(6,1346)X1,X2,Y1,Y2,Z1,Z2
1346    FORMAT(1X,'XYZ12=',6E14.5)
        CALL GGS(XA,YA,ZA,XB,YB,ZB,X1,Y1,Z1,X2,Y2,Z2,AM,
       2DS,CGDS,SGDS,DT,SGDT,INT,ETA,GAM,P11,P12,P21,P22)
        CALL GGS(XA,YA,ZA,XB,YB,ZB,X2,Y2,Z2,X3,Y3,Z3,AM,
       2DS,CGDS,SGDS,DT,SGDT,INT,ETA,GAM,Q11,Q12,Q21,Q22)
        CALL GGS(XB,YB,ZB,XC,YC,ZC,X1,Y1,Z1,X2,Y2,Z2,AM,
       2DS,CGDS,SGDS,DT,SGDT,INT,ETA,GAM,R11,R12,R21,R22)
        CALL GGS(XB,YB,ZB,XC,YC,ZC,X2,Y2,Z2,X3,Y3,Z3,AM,
       2DS,CGDS,SGDS,DT,SGDT,INT,ETA,GAM,S11,S12,S21,S22)
```

```
          ZABG=P22+Q21+R12+S11
    CC    WRITE(6,7898)ZABG
    7898  FORMAT(1X,'EXITING ZABG WITH ZABG=',2E14.5)
          RETURN
          END
**********file dzabgnloss.f*******
C***DOUBLE PRECISION VERSION
C***PROGRAM TO CALCULATE MUTUAL IMPEDANCE BETWEEN TWO DIPOLES
C***WITH ARBITRARY LENGTH AND ORIENTATION.  A PIECEWISE-
C***SINUSOIDAL CURRENT DISTRIBUTION IS ASSUMED.
          SUBROUTINE DSZABG(SX1,SX2,SX3,SY1,SY2,SY3,SZ1,SZ2,SZ3,
         2SXA,SXB,SXC,SYA,SYB,SYC,SZA,SZB,SZC,DZABG)
          IMPLICIT REAL*8 (A-H,O-Z)
          COMPLEX*16 P11,P12,P21,P22,Q11,Q12,Q21,Q22,R11,R12,R21,R22
          COMPLEX*16 S11,S12,S21,S22,JCOM,GAM,CGDS,SGDS,SGDT,ETA
          COMPLEX*16 DZABG,EP3,EGDS,EGDT
          REAL*4 SX1,SX2,SX3,SY1,SY2,SY3,SZ1,SZ2,SZ3
          REAL*4 SXA,SXB,SXC,SYA,SYB,SYC,SZA,SZB,SZC
          REAL*4 FHZ,ER3,SIG3,TD3
          COMMON /F/ FHZ,ER3,SIG3,TD3
          JCOM=(0.D0,1.D0)
          PI=3.1415926535898D0
          TPI=2.0D0*PI
          B=TPI
          E0=8.854D-12
          U0=1.2566D-6
          OMEGA=TPI*FHZ
    CC    WRITE(6,2843)OMEGA
    2843  FORMAT(1X,'OMEGA=',E12.5)
          IF(SIG3.LT.0.0D0)EP3=ER3*E0*DCMPLX(1.0D0,-TD3)
          IF(TD3.LT.0.0D0)EP3=DCMPLX(ER3*E0,-SIG3/OMEGA)
    CC    WRITE(6,7755)ER3,E0,EP3
    7755  FORMAT(1X,'ER3,E0,EP3=',4E12.5)
          ETA=CDSQRT(U0/EP3)
          GAM=OMEGA*CDSQRT(-U0*EP3)
C**COMPUTE GAMMA BY EQUATION IN HAYT PAGE 333
    CC    GAM=JCOM*OMEGA*CDSQRT(U0*EP3)*CDSQRT(1.D0-JCOM*SIG3/(OMEGA*EP3))
    CC    WRITE(6,8888)GAM
    8888  FORMAT(1X,'HYAT GAM=',2E12.5)
          AM=0.0001D0
          INT=0
          X1=SX1
          X2=SX2
          X3=SX3
          Y1=SY1
          Y2=SY2
          Y3=SY3
          Z1=SZ1
          Z2=SZ2
          Z3=SZ3
          XA=SXA
          XB=SXB
          XC=SXC
          YA=SYA
          YB=SYB
          YC=SYC
          ZA=SZA
          ZB=SZB
          ZC=SZC
          XBA=XB-XA
          YBA=YB-YA
          ZBA=ZB-ZA
          X21=X2-X1
          Y21=Y2-Y1
          Z21=Z2-Z1
          DS=DSQRT(XBA*XBA+YBA*YBA+ZBA*ZBA)
          DT=DSQRT(X21*X21+Y21*Y21+Z21*Z21)
    CC    DSK=B*DS
    CC    DTK=B*DT
    CC    CGDS=DCMPLX(DCOS(DSK),0.0D0)
    CC    SGDS=DCMPLX(0.0D0,DSIN(DSK))
    CC    SGDT=DCMPLX(0.0D0,DSIN(DTK))
          EGDS=CDEXP(GAM*DS)
          EGDT=CDEXP(GAM*DT)
          CGDS=(EGDS+1.0D0/EGDS)/2.0D0
```

```
       SGDS=(EGDS-1.0D0/EGDS)/2.0D0
       SGDT=(EGDT-1.0D0/EGDT)/2.0D0
       CALL DGGS(XA,YA,ZA,XB,YB,ZB,X1,Y1,Z1,X2,Y2,Z2,AM,
      2DS,CGDS,SGDS,DT,SGDT,INT,ETA,GAM,P11,P12,P21,P22)
       CALL DGGS(XA,YA,ZA,XB,YB,ZB,X2,Y2,Z2,X3,Y3,Z3,AM,
      2DS,CGDS,SGDS,DT,SGDT,INT,ETA,GAM,Q11,Q12,Q21,Q22)
       CALL DGGS(XB,YB,ZB,XC,YC,ZC,X1,Y1,Z1,X2,Y2,Z2,AM,
      2DS,CGDS,SGDS,DT,SGDT,INT,ETA,GAM,R11,R12,R21,R22)
       CALL DGGS(XB,YB,ZB,XC,YC,ZC,X2,Y2,Z2,X3,Y3,Z3,AM,
      2DS,CGDS,SGDS,DT,SGDT,INT,ETA,GAM,S11,S12,S21,S22)
       DZABG=P22+Q21+R12+S11
CC     WRITE(6,8899)DZABG
8899   FORMAT(1X,'EXITING DZABG, DZABG=',2E14.5)
       RETURN
       END
```

APPENDIX B

```
*** Copyright MIT Lincoln Laboratory 1991
***Input data file for adaptive nulling with four auxiliary probes.
***sdipjamhyper data file, filename sdipjamhyper.datacirconicrr4
 &DIPOLE NCOLX=8,NROWY=1,HZIN=0.001,HLIN=2.6,
  DXIN=6.888,DYIN=6.888,ARADIN=0.0039,
  ICIRC=1,CRADIN=11.81,HLSIN=0.25,
  IWL=0,FCHZ=120.0E6,BWFHZ=1.0E0,NFREQ=5,IWR=0,
  NPDX=0,NXDUM=0,NYDUM=0,ER3=73.5,SIG3=0.5,TD3=-1.0,
  ZLOAD=50.0,ZCHAR=0.0,NGEN=8,IGEN=0,

NSCANS=1,
 THSINC=5.0,

IMUT=1,IBLTSL=0,

IENORM=1,ICHEB=0,SLLDB=20.,EDGTDB=0.,

IPATRN=1,IPRCOM=1,IANGLP=0,
 NPHCT=0,NTHPT=499,
 THDR=180.,THDMIN=-90.,

NCOLXN=121,NROWYN=1,NCOLZN=1,
 RLSYIN=0.0,RLSZIN=0.0,

NCOLXN=117,NROWYN=1,NCOLZN=1,

INEAR=1,

IPOL=2,IGRNDP=0,

ITLTPR=0,ITLTDP=0,

NFCOLX=1,NFROWY=1,

IANTX=1,IANTY=0,NPOWER=0,

IPCONN=1,IPCONF=0,IPCUTF=0,IPCFX=0,IPCFY=0,IPCFZ=0,

ITEK=0,

IQUAN=0,IRNERR=0,ELERDB=0.02,ELERDG=0.2,NBMOD=12,

NRAN=1,NBADWT=32,AWERDB=0.0,AWERDG=0.0,

NAUX=7,IAUXA(1)=1,2,3,4,5,6,7,

IATTEN=1,
 NJAMS=7,ISLC=0,AUXADB(1)=8*0.0,
 PWRJDB(1)=40.,40.,15.,15.,3*-99.0,
```

```
YJAMIN(1)=7*0.0,
XFOCIN=0.0,ZFOCIN=0.0,
XJAMIN(1)=5.9,-5.9,2*0.0,3*-0.0,
ZJAMIN(1)=0.0,0.0,4.0,-4.0,3*0.0
YNIN=0.0,
NCOLXN=101,NTHPT=101,
XNIN=-15.,ZNIN=-15.,RLSXIN=30.,RLSZIN=30.,NCOLXN=41,NCOLZN=41,
&END

***Output data file for adaptive nulling with four auxiliary probes.
***sdipjamhyper data file, filename sdipjamhyper.datacirconicrr4
   XJAMIN(1),YJAMIN(1),ZJAMIN(1)=        5.900        0.000        0.000
   FGHZ=       0.1200000
   DX,DY,HL,ARAD=           0.17496        0.17496        0.06604        0.00010
   IV,VTA=    1    0.5916E-02  0.2211E-02
   IV,VTA=    2    0.5916E-02  0.2211E-02
   IV,VTA=    3    0.5916E-02  0.2211E-02
   IV,VTA=    4    0.5916E-02  0.2211E-02
   IV,VTA=    5    0.5916E-02  0.2211E-02
   IV,VTA=    6    0.5916E-02  0.2211E-02
   IV,VTA=    7    0.5916E-02  0.2211E-02
   IV,VTA=    8    0.5916E-02  0.2211E-02
**********array mutual impedance matrix (first row)*******
   Z(1,   1)= 0.91705E+02  0.12403E+02
   Z(1,   2)=-0.33552E-01  0.19136E+00
   Z(1,   3)=-0.14488E-01 -0.54125E-02
   Z(1,   4)= 0.29420E-02  0.13780E-02
   Z(1,   5)= 0.15283E-02 -0.11371E-02
   Z(1,   6)= 0.29420E-02  0.13780E-02
   Z(1,   7)=-0.14488E-01 -0.54125E-02
   Z(1,   8)=-0.33552E-01  0.19136E+00
   NEL,NCOLX,NROWY=     8    8    1
   CURRENTS
         1   1.000000         0.683E-04       13.
         2   1.000000         0.683E-04       13.
         3   1.000000         0.683E-04       13.
         4   1.000000         0.683E-04       13.
         5   1.000000         0.683E-04       13.
         6   1.000000         0.683E-04       13.
         7   1.000000         0.683E-04       13.
         8   1.000000         0.683E-04       13.
   IC,RWTA=    1    0.35355E+00
   IC,RWTA=    2    0.35355E+00
   IC,RWTA=    3    0.35355E+00
   IC,RWTA=    4    0.35355E+00
   IC,RWTA=    5    0.35355E+00
   IC,RWTA=    6    0.35355E+00
   IC,RWTA=    7    0.35355E+00
   IC,RWTA=    8    0.35355E+00
   I,CWTA(I,1)=   1   0.34510E+00 -0.76830E-01
   I,CWTA(I,1)=   2   0.34510E+00 -0.76830E-01
   I,CWTA(I,1)=   3   0.34510E+00 -0.76830E-01
   I,CWTA(I,1)=   4   0.34510E+00 -0.76830E-01
   I,CWTA(I,1)=   5   0.34510E+00 -0.76830E-01
   I,CWTA(I,1)=   6   0.34510E+00 -0.76830E-01
   I,CWTA(I,1)=   7   0.34510E+00 -0.76830E-01
   I,CWTA(I,1)=   8   0.34510E+00 -0.76830E-01
******ring array weights before nulling (amp,phase)*************
   I=   1   CWTADB,CWTADG=       0.00000        -12.55098
   I=   2   CWTADB,CWTADG=       0.00000        -12.55099
   I=   3   CWTADB,CWTADG=       0.00000        -12.55097
   I=   4   CWTADB,CWTADG=       0.00000        -12.55098
   I=   5   CWTADB,CWTADG=       0.00000        -12.55098
   I=   6   CWTADB,CWTADG=       0.00000        -12.55097
   I=   7   CWTADB,CWTADG=       0.00000        -12.55098
   I=   8   CWTADB,CWTADG=       0.00000        -12.55097
   Z(1,   1)= 0.91705E+02  0.12403E+02
   Z(1,   2)=-0.33552E-01  0.19136E+00
   Z(1,   3)=-0.14488E-01 -0.54125E-02
   Z(1,   4)= 0.29420E-02  0.13780E-02
   Z(1,   5)= 0.15283E-02 -0.11371E-02
   Z(1,   6)= 0.29420E-02  0.13780E-02
   Z(1,   7)=-0.14488E-01 -0.54125E-02
```

```
Z(1,   8)=-0.33552E-01  0.19136E+00
NEL,NCOLX,NROWY=      8      8      1
II,PWRJ IN POWER=     1   0.10000E+05
II,PWRJ IN POWER=     2   0.10000E+05
II,PWRJ IN POWER=     3   0.31623E+02
II,PWRJ IN POWER=     4   0.31623E+02
II,PWRJ IN POWER=     5   0.12589E-09
II,PWRJ IN POWER=     6   0.12589E-09
II,PWRJ IN POWER=     7   0.12589E-09
*****covariance matrix*************************
I,J,CNDB,PHASEN=      1      1         36.35        0.00
I,J,CNDB,PHASEN=      1      2         31.68       91.33
I,J,CNDB,PHASEN=      1      3         24.99     -117.95
I,J,CNDB,PHASEN=      1      4         20.88        6.26
I,J,CNDB,PHASEN=      1      5         20.72       -0.14
I,J,CNDB,PHASEN=      1      6         20.88        6.26
I,J,CNDB,PHASEN=      1      7         24.99     -117.95
I,J,CNDB,PHASEN=      1      8         31.68       91.33
I,J,CNDB,PHASEN=      2      1         31.68      -91.33
I,J,CNDB,PHASEN=      2      2         27.05        0.00
I,J,CNDB,PHASEN=      2      3         20.23      155.55
I,J,CNDB,PHASEN=      2      4          8.12      177.91
I,J,CNDB,PHASEN=      2      5         20.90       -6.14
I,J,CNDB,PHASEN=      2      6          8.28      177.98
I,J,CNDB,PHASEN=      2      7         20.24      155.46
I,J,CNDB,PHASEN=      2      8         27.04        0.00
I,J,CNDB,PHASEN=      3      1         24.99      117.95
I,J,CNDB,PHASEN=      3      2         20.23     -155.55
I,J,CNDB,PHASEN=      3      3         16.67        0.00
I,J,CNDB,PHASEN=      3      4         20.26     -155.49
I,J,CNDB,PHASEN=      3      5         25.01      117.95
I,J,CNDB,PHASEN=      3      6         20.27     -155.41
I,J,CNDB,PHASEN=      3      7         16.52        0.00
I,J,CNDB,PHASEN=      3      8         20.24     -155.46
I,J,CNDB,PHASEN=      4      1         20.88       -6.26
I,J,CNDB,PHASEN=      4      2          8.12     -177.91
I,J,CNDB,PHASEN=      4      3         20.26      155.49
I,J,CNDB,PHASEN=      4      4         27.08        0.00
I,J,CNDB,PHASEN=      4      5         31.71      -91.33
I,J,CNDB,PHASEN=      4      6         27.07        0.00
I,J,CNDB,PHASEN=      4      7         20.27      155.41
I,J,CNDB,PHASEN=      4      8          8.28     -177.98
I,J,CNDB,PHASEN=      5      1         20.72        0.14
I,J,CNDB,PHASEN=      5      2         20.90        6.14
I,J,CNDB,PHASEN=      5      3         25.01     -117.95
I,J,CNDB,PHASEN=      5      4         31.71       91.33
I,J,CNDB,PHASEN=      5      5         36.38        0.00
I,J,CNDB,PHASEN=      5      6         31.71       91.33
I,J,CNDB,PHASEN=      5      7         25.01     -117.95
I,J,CNDB,PHASEN=      5      8         20.90        6.14
I,J,CNDB,PHASEN=      6      1         20.88       -6.26
I,J,CNDB,PHASEN=      6      2          8.28     -177.98
I,J,CNDB,PHASEN=      6      3         20.27      155.41
I,J,CNDB,PHASEN=      6      4         27.07        0.00
I,J,CNDB,PHASEN=      6      5         31.71      -91.33
I,J,CNDB,PHASEN=      6      6         27.08        0.00
I,J,CNDB,PHASEN=      6      7         20.26      155.49
I,J,CNDB,PHASEN=      6      8          8.12     -177.91
I,J,CNDB,PHASEN=      7      1         24.99      117.95
I,J,CNDB,PHASEN=      7      2         20.24     -155.46
I,J,CNDB,PHASEN=      7      3         16.52        0.00
I,J,CNDB,PHASEN=      7      4         20.27     -155.41
I,J,CNDB,PHASEN=      7      5         25.01      117.95
I,J,CNDB,PHASEN=      7      6         20.26     -155.49
I,J,CNDB,PHASEN=      7      7         16.67        0.00
I,J,CNDB,PHASEN=      7      8         20.23     -155.55
I,J,CNDB,PHASEN=      8      1         31.68      -91.33
I,J,CNDB,PHASEN=      8      2         27.04        0.00
I,J,CNDB,PHASEN=      8      3         20.24      155.46
I,J,CNDB,PHASEN=      8      4          8.28      177.98
I,J,CNDB,PHASEN=      8      5         20.90       -6.14
I,J,CNDB,PHASEN=      8      6          8.12      177.91
I,J,CNDB,PHASEN=      8      7         20.23      155.55
```

```
I,J,CNDB,PHASEN=      8     8        27.05           0.00
*********eigenvalues*********************
I,EVLDBN=    1          37.437
I,EVLDBN=    2          37.195
I,EVLDBN=    3           2.771
I,EVLDBN=    4           3.103
I,EVLDBN=    5           0.000
I,EVLDBN=    6           0.000
I,EVLDBN=    7           0.000
I,EVLDBN=    8           0.000
CPROD1,CPROD2= 0.13839E+04-0.85265E-13 0.10000E+01 0.00000E+00
INR NORMALIZATION PARAMETER, INRNOR=    1
I=   1   WANDB=        -12.318
I=   2   WANDB=         -8.734
I=   3   WANDB=         -7.602
I=   4   WANDB=         -8.734
I=   5   WANDB=        -12.318
I=   6   WANDB=         -8.734
I=   7   WANDB=         -7.602
I=   8   WANDB=         -8.734
I,WAN(I,1)=    1    0.11307E+00-0.21414E+00
I,WAN(I,1)=    2    0.34937E+00 0.10851E+00
I,WAN(I,1)=    3    0.32832E+00-0.25671E+00
I,WAN(I,1)=    4    0.34937E+00 0.10851E+00
I,WAN(I,1)=    5    0.11307E+00-0.21414E+00
I,WAN(I,1)=    6    0.34937E+00 0.10851E+00
I,WAN(I,1)=    7    0.32832E+00-0.25671E+00
I,WAN(I,1)=    8    0.34937E+00 0.10851E+00
*********adaptive array weights (amp.,phase)*********
I=   1   WANDB,WANDG=      -4.71576    -62.16515
I=   2   WANDB,WANDG=      -1.13211     17.25469
I=   3   WANDB,WANDG=       0.00000    -38.02192
I=   4   WANDB,WANDG=      -1.13210     17.25474
I=   5   WANDB,WANDG=      -4.71576    -62.16529
I=   6   WANDB,WANDG=      -1.13210     17.25474
I=   7   WANDB,WANDG=       0.00000    -38.02193
I=   8   WANDB,WANDG=      -1.13210     17.25469
*********cancellation*******************
CPROD1,CPROD2= 0.12271E+01 0.12185E-13 0.10000E+01 0.00000E+00
INR NORMALIZATION PARAMETER, INRNOR=    1
INR= QUI,ADAP ,CANCEL=     31.411      0.889    -30.522  DB
CANCDB,NRAN,AVECAN=     -30.52207         1      -30.52207
***Input data file for adaptive nulling with two auxiliary probes.
***sdipjamhyper data file, filename sdipjamhyper.datacirconicrr3
 &DIPOLE NCOLX=8,NROWY=1,HZIN=0.001,HLIN=2.6,
  DXIN=6.888,DYIN=6.888,ARADIN=0.0039,
  ICIRC=1,CRADIN=11.81,HLSIN=0.25,
  IWL=0,FCHZ=120.0E6,BWFHZ=1.0E0,NFREQ=5,IWR=0,
  NPDX=0,NXDUM=0,NYDUM=0,ER3=73.5,SIG3=0.5,TD3=-1.0,
  ZLOAD=50.0,ZCHAR=0.0,NGEN=8,IGEN=0,

NSCANS=1,
  THSINC=5.0,

IMUT=1,IBLTSL=0,

IENORM=1,ICHEB=0,SLLDB=20.,EDGTDB=0.,

IPATRN=1,IPRCOM=1,IANGLP=0,
  NPHCT=0,NTHPT=499,
  THDR=180.,THDMIN=-90.,

RLSYIN=0.0,RLSZIN=0.0,

NCOLXN=117,NROWYN=1,NCOLZN=1,

INEAR=1,

IPOL=2,IGRNDP=0,
  ITLTPR=0,ITLTDP=0,

NFCOLX=1,NFROWY=1,
```

```
IANTX=1,IANTY=0,NPOWER=0,

IPCONN=1,IPCONF=0,IPCUTF=0,IPCFX=0,IPCFY=0,IPCFZ=0,

ITEK=0,

IQUAN=0,IRNERR=0,ELERDB=0.02,ELERDG=0.2,NBMOD=12,

NRAN=1,NBADWT=32,AWERDB=0.0,AWERDG=0.0,

NAUX=7,IAUXA(1)=1,2,3,4,5,6,7,

IATTEN=1,
INRNOR=1,
NJAMS=7,ISLC=0,AUXADB(1)=8*0.0,
PWRJDB(1)=40.,40.,5*-99.0,
YJAMIN(1)=7*0.0,
XFOCIN=0.0,ZFOCIN=0.0,
XJAMIN(1)=5.9,-5.9,2*0.0,2*-4.0,1*0.0,
ZJAMIN(1)=0.0,0.0,4.0,-4.0,3.0,-3.0,1*0.0
YNIN=0.0,
NCOLXN=101,NTHPT=101,
 XNIN=-15.,ZNIN=-15.,RLSXIN=30.,RLSZIN=30.,NCOLXN=41,NCOLZN=41,
&END

***Output data file for adadptive nulling with two auxiliary probes.
***sdipjamhyper data file, filename sdipjamhyper.datacirconicrr3
  XJAMIN(1),YJAMIN(1),ZJAMIN(1)=        5.900         0.000         0.000

FGHZ=        0.1200000
DX,DY,HL,ARAD=           0.17496        0.17496       0.06604       0.00010
IV,VTA=    1     0.5916E-02   0.2211E-02
IV,VTA=    2     0.5916E-02   0.2211E-02
IV,VTA=    3     0.5916E-02   0.2211E-02
IV,VTA=    4     0.5916E-02   0.2211E-02
IV,VTA=    5     0.5916E-02   0.2211E-02
IV,VTA=    6     0.5916E-02   0.2211E-02
IV,VTA=    7     0.5916E-02   0.2211E-02
IV,VTA=    8     0.5916E-02   0.2211E-02
*********array mutual impedance matrix (first row)*******
 Z(1,    1)= 0.91705E+02 0.12403E+02
 Z(1,    2)=-0.33552E-01 0.19136E+00
 Z(1,    3)=-0.14488E-01-0.54125E-02
 Z(1,    4)= 0.29420E-02 0.13780E-02
 Z(1,    5)= 0.15283E-02-0.11371E-02
 Z(1,    6)= 0.29420E-02 0.13780E-02
 Z(1,    7)=-0.14488E-01-0.54125E-02
 Z(1,    8)=-0.33552E-01 0.19136E+00
NEL,NCOLX,NROWY=     8       8       1
CURRENTS
     1   1.000000           0.683E-04        13.
     2   1.000000           0.683E-04        13.
     3   1.000000           0.683E-04        13.
     4   1.000000           0.683E-04        13.
     5   1.000000           0.683E-04        13.
     6   1.000000           0.683E-04        13.
     7   1.000000           0.683E-04        13.
     8   1.000000           0.683E-04        13.
IC,RWTA=    1    0.35355E+00
IC,RWTA=    2    0.35355E+00
IC,RWTA=    3    0.35355E+00
IC,RWTA=    4    0.35355E+00
IC,RWTA=    5    0.35355E+00
IC,RWTA=    6    0.35355E+00
IC,RWTA=    7    0.35355E+00
IC,RWTA=    8    0.35355E+00
I,CWTA(I,1)=    1    0.34510E+00-0.76830E-01
I,CWTA(I,1)=    2    0.34510E+00-0.76830E-01
I,CWTA(I,1)=    3    0.34510E+00-0.76830E-01
I,CWTA(I,1)=    4    0.34510E+00-0.76830E-01
I,CWTA(I,1)=    5    0.34510E+00-0.76830E-01
I,CWTA(I,1)=    6    0.34510E+00-0.76830E-01
I,CWTA(I,1)=    7    0.34510E+00-0.76830E-01
```

```
I,CWTA(I,1)=    8   0.34510E+00-0.76830E-01
******ring array weights before nulling (amp,phase)*************
I=   1   CWTADB,CWTADG=            0.00000      -12.55098
I=   2   CWTADB,CWTADG=            0.00000      -12.55099
I=   3   CWTADB,CWTADG=            0.00000      -12.55098
I=   4   CWTADB,CWTADG=            0.00000      -12.55097
I=   5   CWTADB,CWTADG=            0.00000      -12.55098
I=   6   CWTADB,CWTADG=            0.00000      -12.55097
I=   7   CWTADB,CWTADG=            0.00000      -12.55098
I=   8   CWTADB,CWTADG=            0.00000      -12.55097
Z(1,  1)= 0.91705E+02 0.12403E+02
Z(1,  2)=-0.33552E-01 0.19136E+00
Z(1,  3)=-0.14488E-01-0.54125E-02
Z(1,  4)= 0.29420E-02 0.13780E-02
Z(1,  5)= 0.15283E-02-0.11371E-02
Z(1,  6)= 0.29420E-02 0.13780E-02
Z(1,  7)=-0.14488E-01-0.54125E-02
Z(1,  8)=-0.33552E-01 0.19136E+00
NEL,NCOLX,NROWY=       8       8       1
II,PWRJ IN POWER=      1   0.10000E+05
II,PWRJ IN POWER=      2   0.10000E+05
II,PWRJ IN POWER=      3   0.12589E-09
II,PWRJ IN POWER=      4   0.12589E-09
II,PWRJ IN POWER=      5   0.12589E-09
II,PWRJ IN POWER=      6   0.12589E-09
II,PWRJ IN POWER=      7   0.12589E-09
******covariance matrix*************************
  I,J,CNDB,PHASEN=    1   1       36.35         0.00
  I,J,CNDB,PHASEN=    1   2       31.68        91.33
  I,J,CNDB,PHASEN=    1   3       24.98      -117.94
  I,J,CNDB,PHASEN=    1   4       20.88         6.28
  I,J,CNDB,PHASEN=    1   5       20.72        -0.14
  I,J,CNDB,PHASEN=    1   6       20.88         6.28
  I,J,CNDB,PHASEN=    1   7       24.98      -117.94
  I,J,CNDB,PHASEN=    1   8       31.68        91.33
  I,J,CNDB,PHASEN=    2   1       31.68       -91.33
  I,J,CNDB,PHASEN=    2   2       27.05         0.00
  I,J,CNDB,PHASEN=    2   3       20.24       155.47
  I,J,CNDB,PHASEN=    2   4        8.24       177.97
  I,J,CNDB,PHASEN=    2   5       20.90        -6.17
  I,J,CNDB,PHASEN=    2   6        8.24       177.97
  I,J,CNDB,PHASEN=    2   7       20.24       155.47
  I,J,CNDB,PHASEN=    2   8       27.04         0.00
  I,J,CNDB,PHASEN=    3   1       24.98       117.94
  I,J,CNDB,PHASEN=    3   2       20.24      -155.47
  I,J,CNDB,PHASEN=    3   3       16.62         0.00
  I,J,CNDB,PHASEN=    3   4       20.27      -155.41
  I,J,CNDB,PHASEN=    3   5       25.01       117.93
  I,J,CNDB,PHASEN=    3   6       20.27      -155.41
  I,J,CNDB,PHASEN=    3   7       16.52         0.00
  I,J,CNDB,PHASEN=    3   8       20.24      -155.47
  I,J,CNDB,PHASEN=    4   1       20.88        -6.28
  I,J,CNDB,PHASEN=    4   2        8.24      -177.97
  I,J,CNDB,PHASEN=    4   3       20.27       155.41
  I,J,CNDB,PHASEN=    4   4       27.08         0.00
  I,J,CNDB,PHASEN=    4   5       31.71       -91.33
  I,J,CNDB,PHASEN=    4   6       27.07         0.00
  I,J,CNDB,PHASEN=    4   7       20.27       155.41
  I,J,CNDB,PHASEN=    4   8        8.24      -177.97
  I,J,CNDB,PHASEN=    5   1       20.72         0.14
  I,J,CNDB,PHASEN=    5   2       20.90         6.17
  I,J,CNDB,PHASEN=    5   3       25.01      -117.93
  I,J,CNDB,PHASEN=    5   4       31.71        91.33
  I,J,CNDB,PHASEN=    5   5       36.38         0.00
  I,J,CNDB,PHASEN=    5   6       31.71        91.33
  I,J,CNDB,PHASEN=    5   7       25.01      -117.93
  I,J,CNDB,PHASEN=    5   8       20.90         6.17
  I,J,CNDB,PHASEN=    6   1       20.88        -6.28
  I,J,CNDB,PHASEN=    6   2        8.24      -177.97
  I,J,CNDB,PHASEN=    6   3       20.27       155.41
  I,J,CNDB,PHASEN=    6   4       27.07         0.00
  I,J,CNDB,PHASEN=    6   5       31.71       -91.33
  I,J,CNDB,PHASEN=    6   6       27.08         0.00
```

```
I,J,CNDB,PHASEN=      6   7        20.27       155.41
I,J,CNDB,PHASEN=      6   8         8.24      -177.97
I,J,CNDB,PHASEN=      7   1        24.98       117.94
I,J,CNDB,PHASEN=      7   2        20.24      -155.47
I,J,CNDB,PHASEN=      7   3        16.52         0.00
I,J,CNDB,PHASEN=      7   4        20.27      -155.41
I,J,CNDB,PHASEN=      7   5        25.01       117.93
I,J,CNDB,PHASEN=      7   6        20.27      -155.41
I,J,CNDB,PHASEN=      7   7        16.62         0.00
I,J,CNDB,PHASEN=      7   8        20.24      -155.47
I,J,CNDB,PHASEN=      8   1        31.68       -91.33
I,J,CNDB,PHASEN=      8   2        27.04         0.00
I,J,CNDB,PHASEN=      8   3        20.24       155.47
I,J,CNDB,PHASEN=      8   4         8.24       177.97
I,J,CNDB,PHASEN=      8   5        20.90        -6.17
I,J,CNDB,PHASEN=      8   6         8.24       177.97
I,J,CNDB,PHASEN=      8   7        20.24       155.47
I,J,CNDB,PHASEN=      8   8        27.05         0.00
*********eigenvalues********************
I,EVLDBN=    1         37.195
I,EVLDBN=    2         37.437
I,EVLDBN=    3          0.000
I,EVLDBN=    4          0.000
I,EVLDBN=    5          0.000
I,EVLDBN=    6          0.000
I,EVLDBN=    7          0.000
I,EVLDBN=    8          0.000
CPROD1,CPROD2= 0.13835E+04-0.56843E-13 0.10000E+01 0.00000E+00
INR NORMALIZATION PARAMETER, INRNOR=   1
I=    1   WANDB=       -14.003
I=    2   WANDB=        -8.939
I=    3   WANDB=        -6.886
I=    4   WANDB=        -8.939
I=    5   WANDB=       -14.003
I=    6   WANDB=        -8.939
I=    7   WANDB=        -6.886
I=    8   WANDB=        -8.939
I,WAN(I,1)=   1   0.48427E-01-0.19349E+00
I,WAN(I,1)=   2   0.35635E+00 0.26440E-01
I,WAN(I,1)=   3   0.43481E+00-0.12564E+00
I,WAN(I,1)=   4   0.35635E+00 0.26441E-01
I,WAN(I,1)=   5   0.48427E-01-0.19349E+00
I,WAN(I,1)=   6   0.35635E+00 0.26441E-01
I,WAN(I,1)=   7   0.43481E+00-0.12564E+00
I,WAN(I,1)=   8   0.35635E+00 0.26441E-01
*********adaptive array weights (amp.,phase)*********
I=    1   WANDB,WANDG=     -7.11720     -75.94859
I=    2   WANDB,WANDG=     -2.05298       4.24348
I=    3   WANDB,WANDG=      0.00000     -16.11658
I=    4   WANDB,WANDG=     -2.05297       4.24352
I=    5   WANDB,WANDG=     -7.11719     -75.94872
I=    6   WANDB,WANDG=     -2.05298       4.24352
I=    7   WANDB,WANDG=      0.00000     -16.11658
I=    8   WANDB,WANDG=     -2.05297       4.24348
*********cancellation*******************
CPROD1,CPROD2= 0.10001E+01-0.63768E-14 0.10000E+01 0.00000E+00
INR NORMALIZATION PARAMETER, INRNOR=   1
INR= QUI,ADAP ,CANCEL=      31.410     0.000    -31.410    DB
CANCDB,NRAN,AVECAN=   -31.40966       1.     -31.40966
```

I claim:

1. A hyperthermia applicator for inducing a temperature rise in a target, comprising
   a plurality of electric field radiators;
   a source of electric field radiation coupled to each electric field radiator through a controllable transmit weighting network coupled to a respective electric field radiator, each weighting network controlling the phase and amplitude of electric field radiation coupled from the source to the respective electric field radiator in response to a respective feedback signal;
   at least one electric field probe for detecting electric field radiation from the plurality of radiators; and
   a controller means coupled to the electric field probes for receiving the detected electric field radiation and generating the respective feedback signals, and for adjusting the feedback signal in response to the detected electric field radiation so that the detected electric field radiation is minimized at the electric field probe.

2. The apparatus of claim 1, wherein the plurality of electric field radiators comprises a phased-array of electric field transmit elements.

3. The apparatus of claim 2, wherein the phased-array of electric field transmit elements comprises an annular array for surrounding the target.

4. The apparatus of claim 3, wherein the annular array comprises between 4 and 12 transmit elements aligned substantially parallel to each other and substantially uniformly distributed along the perimeter of a cylinder.

5. The apparatus of claim 4, wherein the diameter of the cylinder is between 40 and 80 cm.

6. The apparatus of claim 1, wherein the electric field probes comprise a plurality of probe elements adapted to be disposed non-invasively along the perimeter of the target.

7. The apparatus of claim 6, wherein the target approximates an ellipse and the electric field probes comprise at least one probe element adapted to be positioned at the front, back, and on each side of the target.

8. The apparatus of claim 1, further comprising
at least one secondary electric field probe for detecting electric field radiation;
wherein the controller means adjusts the feedback signals in response to the electric field radiation detected by the secondary electric field probe so that the electric field radiation is maximized at the secondary electric field probe.

9. The apparatus of claim 8, wherein the plurality of electric field radiators comprises a phased-array of electric field transmit elements, and the secondary electric field probe is adapted to be disposed at the desired focus of the phased-array.

10. The apparatus of claim 9, wherein the phased-array of electric field transmit elements comprises an annular array for surrounding the target.

11. The apparatus of claim 10, wherein the annular array comprises between 4 and 12 transmit elements aligned substantially parallel to each other and substantially uniformly distributed along the perimeter of a cylinder.

12. The apparatus of claim 11, wherein the diameter of the cylinder is between 40 and 80 cm.

13. The apparatus of claim 12, wherein
the electric field probes comprise a plurality of probe elements adapted to be disposed non-invasively along the perimeter of the target; and
the secondary electric field probe comprises at least one probe element adapted to be disposed invasively within the target at the desired focus of the electric field energy.

14. The apparatus of claim 13, wherein the target approximates an ellipse and
the electric field probes comprise at least one probe element adapted to be positioned at the front, back, and on each side of the target.

15. The apparatus of claim 14, wherein the plurality of electric field radiators comprises an annular phased-array of electric field transmit elements for surrounding the target; and
the secondary electric field probe is adapted to be disposed at the desired focus of the phased-array.

16. The apparatus of claim 1, wherein the controller means performs a matrix inversion to generate the feedback signal.

17. The apparatus of claim 16, wherein the controller means comprises a receiver coupled to the electric field probes for receiving voltages $v_1^i, v_2^i, \ldots, v_N^i$ due to the mth and nth electric field radiator at the ith electric field probe;
means for forming a cross correlation $R_{mn}^i$ of the received voltages, the cross correlation being given by $$R_{mn}^i = E(v_m^i v_n^{i*}),$$

where * means complex conjugate and $E(.)$ means mathematical expectation;
means for forming a channel correlation matrix R given by $$R = \sum_{i=1}^{N_{aux}} R_i,$$

where $N_{aux}$ is the number of electric field probes, $R_i$ is the sample correlation matrix observed at the ith electric field probe; and
means for generating an adapted transmit weight vector $w_a$ given by $$w_a = R^{-1} w_q,$$

where generally the transmit weight vector $w = (w_1, w_2, \ldots, w_N)^T$ represents the transmit weights of each of N controllable weighting networks, and $w_q$ represents the quiescent transmit weight vector;
wherein the controller means adjusts the feedback signal in response to the adapted transmit weight vector $w_a$.

18. The apparatus of claim 1, wherein the controller means performs a gradient search algorithm to generate the feedback signal.

19. The apparatus of claim 18, wherein the controller means comprises
a receiver coupled to the electric field probes for receiving voltage amplitudes $|v_1^j|, |v_2^j|, \ldots, |v_N^j|$ due to the mth and nth electric field radiator at the ith electric field probe for the jth configuration of the transmit weights $w_{nj}$;
means for calculating a figure of merit $F_{nj}$ from the received voltage amplitudes given by $$F_{nj} = \sum_{i=1}^{N_{aux}} |v_{nj}^j|^2$$

where $N_{aux}$ is the number of electric field probes,
means for dithering the transmit weights $w_{nj}$ by a small amount in amplitude, $\Delta A_{nj}$, and phase, $\Delta \Phi_{nj}$;
means for determining the figure of merit differences $\Delta F_{Anj}$ and $\Delta F_{\Phi nj}$ caused by dithering the amplitude and phase, respectively,
means for determining gradient search directions search directions $r_{Anj}$ and $r_{\Phi nj}$ given by $$r_{Anj} = -\frac{\frac{\Delta F_{Anj}}{\Delta A}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}$$

and $$r_{\Phi nj} = -\frac{\frac{\Delta F_{\Phi nj}}{\Delta \Phi}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}.$$

respectively, and means for generating the new transmit weight $w_{n(j+1)}$ for the (j+1)th configuration where the amplitude component of the new weight is given by $$A_{n,j+1} = A_{nj} + \Delta A r_{Anj}$$

and the phase component of the new weight is given by $$\Phi_{n,j+1} = \Phi_{nj} + \Delta \Phi r_{\Phi nj}.$$

20. A hyperthermia applicator for inducing a temperature rise in a target, comprising
an annular phased array of electric field radiators for surrounding a target;
a source of electric field radiation coupled to each electric field radiator through a controllable transmit weighting network coupled to a respective electric field radiator, each weighting network controlling the phase and amplitude of electric field radiation coupled from the source to the respective electric field radiator in response to a respective feedback signal;
a plurality of electric field probe elements adapted to be disposed non-invasively along the perimeter of the target for detecting electric field radiation from the annular phased array of radiators; and
a controller means coupled to the electric field probes for receiving the detected electric field radiation and generating the respective feedback signals, and for adjusting the feedback signal in response to the detected electric field radiation so that the detected electric field radiation is minimized at the electric field probe elements.

21. The apparatus of claim 20, wherein the annular array comprises between 4 and 12 transmit elements aligned substantially parallel to each other and substantially uniformly distributed along the perimeter of a cylinder.

22. The apparatus of claim 21, wherein the diameter of the cylinder is between 40 and 80 cm.

23. The apparatus of claim 20, wherein the target approximates an ellipse and the electric field probes comprise at least one probe element adapted to be positioned at the front, back, and on each side of the target.

24. The apparatus of claim 20, further comprising at least one secondary electric field probe adapted to be disposed at the desired focus of the phased-array for detecting electric field radiation;
wherein the controller means adjusts the feedback signals in response to the electric field radiation detected by the secondary electric field probe so that the electric field radiation is maximized at the secondary electric field probe.

25. The apparatus of claim 24, wherein the secondary electric field probe comprises at least one probe element adapted to be disposed invasively within the target.

26. The apparatus of claim 20, wherein the controller means performs a matrix inversion to generate the feedback signal.

27. The apparatus of claim 26, wherein the controller means comprises
a receiver coupled to the electric field probes for receiving voltages $v_1^i, v_2^i, \ldots, v_N^i$ due to the mth and nth electric field radiator at the ith electric field probe;
means for forming a cross correlation $R_{mn}^i$ of the received voltages, the cross correlation being given by $$R_{mn}^i = E(v_m^i v_n^{i*}),$$

where * means complex conjugate and E(.) means mathematical expectation;
means for forming a channel correlation matrix R given by $$R = \sum_{i=1}^{N_{aux}} R_i,$$

where $N_{aux}$ is the number of electric field probes, $R_i$ is the sample correlation matrix observed at the ith electric field probe; and
means for generating an adapted transmit weight vector $w_a$ given by $$w_a = R^{-1} w_q,$$

where generally the transmit weight vector $w = (w_1, w_2, \ldots, w_N)^T$ represents the transmit weights of each of N controllable weighting networks, and $w_q$ represents the quiescent transmit weight vector;
wherein the controller means adjusts the feedback signal in response to the adapted transmit weight vector $w_a$.

28. The apparatus of claim 20, wherein the controller means performs a gradient search algorithm to generate the feedback signal.

29. The apparatus of claim 28, wherein the controller means comprises
a receiver coupled to the electric field probes for receiving voltage amplitudes $|v_1^j|, |v_2^j|, \ldots, |v_N^j|$ due to the mth and nth electric field radiator at the ith electric field probe for the jth configuration of the transmit weights $w_{nj}$;
means for calculating a figure of merit $F_{nj}$ from the received voltage amplitudes given by $$F_{nj} = \sum_{i=1}^{N_{aux}} |v_{nj}^i|^2$$

where $N_{aux}$ is the number of electric field probes, means for dithering the transmit weights $w_{nj}$ by a small amount in amplitude, $\Delta A_{nj}$, and phase, $\Delta \Phi_{nj}$;
means for determining the figure of merit differences $\Delta F_{Anj}$ and $\Delta F_{\Phi nj}$ caused by dithering the amplitude and phase, respectively, means for determining gradient search directions search directions $r_{Anj}$ and $r_{\Phi nj}$ given by $$r_{Anj} = - \frac{\frac{\Delta F_{Anj}}{\Delta A}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}$$

and $$r_{\Phi nj} = - \frac{\frac{\Delta F_{\Phi nj}}{\Delta \Phi}}{\sqrt{\sum_{n=1}^{N}\left[\left(\frac{\Delta F_{Anj}}{\Delta A}\right)^2 + \left(\frac{\Delta F_{\Phi nj}}{\Delta \Phi}\right)^2\right]}}.$$

respectively, and means for generating the new transmit weight $w_{n,(j+1)}$ for the (j+1)th configuration where the amplitude component of the new weight is given by $$A_{n,j+1} = A_{nj} + \Delta A r_{Anj}$$

and the phase component of the new weight is given by $$\Phi_{n,j+1} = \Phi_{nj} + \Delta \Phi r_{\Phi nj}.$$

30. A method for inducing a temperature rise in a target, comprising the steps of:

surrounding a target with an annular phased array of electric field radiators;

coupling a source of electric field radiation to each electric field radiator through a controllable transmit weighting network coupled to a respective electric field radiator;

controlling the phase and amplitude of electric field radiation coupled from the source to the respective electric field radiator with each weighting network in response to a respective feedback signal;

detecting electric field radiation from the annular phased array of radiators with a plurality of electric field probe elements disposed non-invasively along the perimeter of the target; and receiving the detected electric field radiation and generating the respective feedback signals for adjusting the controllable transmit weighting network in response to the detected electric field radiation so that the detected electric field radiation is minimized at the electric field probe elements.

* * * * *